United States Patent
Wu

(10) Patent No.: US 10,221,168 B1
(45) Date of Patent: Mar. 5, 2019

(54) SMALL-COMPOUND ENHANCERS FOR FUNCTIONAL O-MANNOSYLATION OF ALPHA-DYSTROGLYCAN, AND USES THEREOF

(71) Applicant: Xiaohua Wu, Matthews, NC (US)

(72) Inventor: Xiaohua Wu, Matthews, NC (US)

(73) Assignee: Xiao Hua Wu, Matthews, NC (US)

( * ) Notice: Subject to any disclaimer, the term of this patent is extended or adjusted under 35 U.S.C. 154(b) by 0 days.

(21) Appl. No.: 15/044,598

(22) Filed: Feb. 16, 2016

Related U.S. Application Data

(60) Provisional application No. 62/117,520, filed on Feb. 18, 2015.

(51) Int. Cl.
*C07D 413/14* (2006.01)
*C07D 495/04* (2006.01)
*C07D 409/14* (2006.01)
*C07D 417/14* (2006.01)
*C07D 513/04* (2006.01)

(52) U.S. Cl.
CPC ......... *C07D 417/14* (2013.01); *C07D 409/14* (2013.01); *C07D 413/14* (2013.01); *C07D 495/04* (2013.01); *C07D 513/04* (2013.01)

(58) Field of Classification Search
None
See application file for complete search history.

(56) References Cited

U.S. PATENT DOCUMENTS

| 8,642,660 B2 * | 2/2014 | Goldfarb | A61K 31/122 |
| | | | 514/18.9 |
| 2009/0163545 A1 * | 6/2009 | Goldfarb | A61K 31/122 |
| | | | 514/312 |

OTHER PUBLICATIONS

Lv, Fengping Bioorganic & Medicinal Chemistry (2015), 23 (24) 7661-7670. (Year: 2015).*

* cited by examiner

*Primary Examiner* — Nyeemah A Grazier

(57) ABSTRACT

The present invention provides compounds that can enhance functional O-mannosylation of proteins including alpha-dystroglycan. Also provided are methods of preparation of the compounds defined by the formula I. Also provided are the methods of using the compounds or the pharmaceutical acceptable salts or prodrugs thereof in treating and preventing subjects suffering from the diseases including muscular dystrophies and cancers.

17 Claims, 1 Drawing Sheet

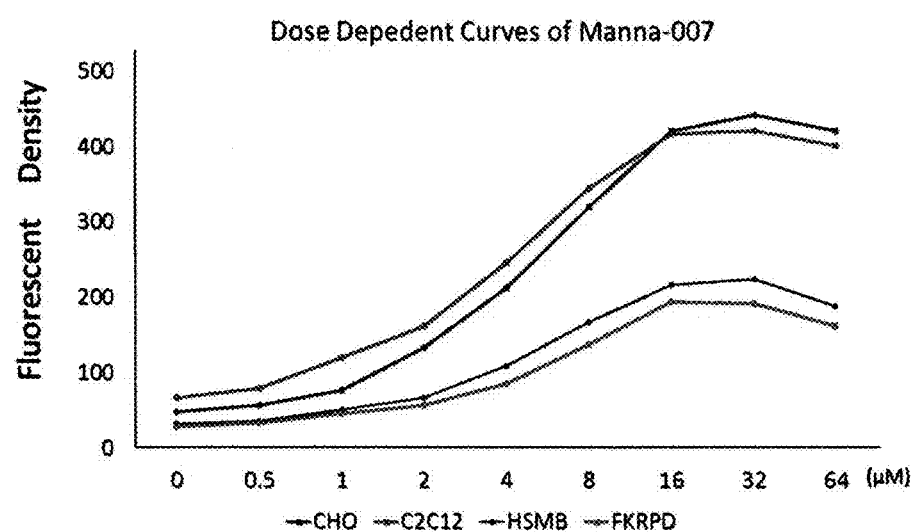

SMALL-COMPOUND ENHANCERS FOR FUNCTIONAL O-MANNOSYLATION OF ALPHA-DYSTROGLYCAN, AND USES THEREOF

FIELD OF THE INVENTION

The present invention relates to compounds that can enhance functional O-mannosylation of proteins including alpha-dystroglycan. The present invention also relates to methods for preparation of the compounds and for treatment of muscular dystrophies and cancers using the compounds.

BACKGROUND OF THE INVENTION

Protein O-mannosylation is evolutionarily conserved from bacteria to humans (Lommel and Strahl 2009). It is known that in fungi, the majority of secreted and cell wall proteins are highly O-mannosylated (Strahl-Bolsinger, Gentzsch et al. 1999). So far, in humans, there are total of 50 proteins harboring O-mannosyl glycan including dystroglycan (DG) (Endo 2003; Hu, Li et al. 2011), 37 of cadherins, 6 of plexins (Baenziger 2013), 4 of lecticans (aggrecan, brevican, neurocan, and versican) (Pacharra, Hanisch et al. 2013), CD24 (Bleckmann, Geyer et al. 2009), PTPRZ1 (Dwyer, Baker et al. 2012), and neurofascin 186 (Pacharra, Hanisch et al. 2012). Most of these proteins are either extracellular matrix (ECM) proteins, or the receptors of ECM proteins. The knowledge of protein O-mannosylation in mammalian cells are mainly from studies on DG that was originally isolated as a laminin binding protein named as Crainin from embryonic chicken brain cells (Smalheiser and Schwartz 1987). It is a ubiquitously expressed plasma membrane associated receptor and abundant in skeletal muscles and heart. In muscles, DG associates with dystrophin and other glycoproteins forming a large protein complex so called dystrophin-associated glycoproteins complex (DAGC) (Ervasti, Ohlendieck et al. 1990). Dystroglycan is encoded by DAG1 gene that produces one mRNA and is translated into a single polypeptide that is cleaved into two subunits: $\alpha$-DG and $\beta$-DG (Ibraghimov-Beskrovnaya, Ervasti et al. 1992). The two subunits remain tightly associated in a non-covalent manner as the key components of the DAGC. $\alpha$-DG is located on the cell surfaces and serves as the receptor for several ECM proteins such as agrin (Bowe, Deyst et al. 1994), laminins (Smalheiser and Schwartz 1987), and perlecan (Schneider, Khalil et al. 2006). $\beta$-DG protein contains a transmembrane domain and its cytoplasmic tail interacts with cytoskeletal proteins, such as dystrophin, plectin, dystrobrevin, and other signaling molecules (Yang, Jung et al. 1995; Rezniczek, Konieczny et al. 2007; Swiderski, Shaffer et al. 2014). Thus, through their interactions with other proteins, $\alpha$-DG and $\beta$-DG connect the ECM and the cytoskeletons, which plays an important role in muscle functions (Ervasti and Campbell 1993). $\alpha$-DG is involved in many physical and pathological processes such as development (Durbeej, Larsson et al. 1995), muscular dystrophies (Brockington, Yuva et al. 2001), cancer progression (Bao, Kobayashi et al. 2009), and viral infections (Barresi and Campbell 2006). Importantly, $\alpha$-DG is highly glycosylated with multiple forms of glycans, one of which is O-mannosyl glycan that is essential for its ligand binding activity, hereafter referred to it as the functional O-mannosyl glycan (FOG) (Alhamidi, Kjeldsen Buvang et al. 2011). Deficiency of the FOG on $\alpha$-DG also called hypoglycosylation of $\alpha$-DG impairs its ligand binding activity and results in various disorders including muscular dystrophies and cancer progression for review see the reference (Wells 2013).

Muscular Dystrophies

Muscular dystrophies (MD) are a large group of genetically heterogeneous diseases with a wide spectrum of clinical manifestations, which are characterized by progressive muscle weakness and wasting. Most MD patients eventually lose their mobility and many of them die prematurely. To date, there is no effective treatment for any type of MD. The majority of MDs are caused by genetic defects in the genes involved in the connections between ECM and cytoskeletons in muscles (Xiong, Kobayashi et al. 2006). The genetic defects underlining these MDs can be divided to the following groups. 1) The defects of the ECM proteins such as collagen VI$\alpha$1-3 subunits and laminin $\alpha$2 chain cause Bethlem myopathy and congenital muscular dystrophy (CMD), respectively (Xu, Wu et al. 1994; Camacho Vanegas, Bertini et al. 2001). 2) The defects of dystrophin (Hoffman, Brown et al. 1987) or other components of DAGC such as $\alpha$-through $\delta$-Sarcoglycans cause DMD/BMD and various limb-girdle muscular dystrophies (LGMDs), respectively (Hoffman, Brown et al. 1987; Lim and Campbell 1998; Hara, Balci-Hayta et al. 2011). 3) The defects of the proteins involved in O-mannosylation of $\alpha$-DG: such as Fukutin (Kobayashi, Nakahori et al. 1998), Fukutin relate protein (FKRP) (Esapa, Benson et al. 2002), LARGE (van Reeuwijk, Grewal et al. 2007), POMT1/2 (Beltran-Valero de Bernabe, Currier et al. 2002) (van Reeuwijk, Janssen et al. 2005), or POMGnT1 (Biancheri, Bertini et al. 2006) cause various types of MD, respectively. 4) The defects of other proteins involved in the ECM-cytoskeleton linkage such as $\alpha$7 Integrin (Mayer, Saher et al. 1997) and Plectin (Smith, Eady et al. 1996) result in MD associated with delayed motor milestones and skin blistering, respectively.

Dystroglycanopathies

Hypoglycosylation of $\alpha$-DG results in a group of muscular dystrophies with a wide spectrum of clinical manifestations from mild form of Limb-girdle muscular dystrophy 2I to Walker-Warburg syndrome that affects the development of muscles, brain, and eyes and results in death before age 3. There are 15 types of MD are due to hypoglycosylation of $\alpha$-DG so called dystroglycanopathies, which are caused by the genetic defects of genes involved in the biosynthesis of the FOG of $\alpha$-DG namely: FKTN/Fukutin (Kobayashi, Nakahori et al. 1998), FKRP (Esapa, Benson et al. 2002), LARGE (van Reeuwijk, Grewal et al. 2007), POMT1/2 (Beltran-Valero de Bernabe, Currier et al. 2002) (van Reeuwijk, Janssen et al. 2005), POMGnT1 (Biancheri, Bertini et al. 2006) POMTGnT2/GTDC2 (Manzini, Tambunan et al. 2012), B3GNT1 (Buysse, Riemersma et al. 2013), TMEM5 (Vuillaumier-Barrot, Bouchet-Seraphin et al. 2012), GMPPB (Carss, Stevens et al. 2013), PMOK/SKG196 (Yoshida-Moriguchi, Willer et al. 2013), DPM1, 2, 3, (Lefeber, Schonberger et al. 2009; Barone, Aiello et al. 2012; Yang, Ng et al. 2013) and ISPD (Ackroyd, Skordis et al. 2009). It is anticipated that more types of dystroglycanopathies will be identified in the future since a large number of genes have been identified involved in the biosynthesis of the FOG on $\alpha$-DG (Jae, Raaben et al. 2013)

Duchenne and Becker Muscular Dystrophies

The Duchenne and Becker muscular dystrophies or DMD and BMD are caused by the genetic defects at the sante gene, DMD. DMD is the most common genetic disease since DMD is the largest gene in the human genome and account for about 1% of human genome, which is located on X chromosome. Thus both of the MDs occur almost exclusively in males. Both MDs have similar signs and symptoms but differ in their severity, age of onset, and rate of progression. DMD boys show muscle weakness in early childhood and worsen rapidly. They are usually wheelchair-dependent by adolescence. The BMD boys usually have milder and more varied symptoms. In most cases, muscle weakness becomes apparent later in childhood or in adolescence and worsens at a much slower rate. Both MDs are associated with a heart condition called cardiomyopathy which typically begins in adolescence. Later, the heart muscle malfunction becomes life-threatening in many cases. The DMD boys typically live into their twenties, while BMD boys can survive into their forties or beyond. The prevalence of DMD/BMD is about 1:3500 and 1:100,000 of birth of boys, respectively.

Metastatic Cancers

According to the world health organization report, estimated 14.1 million new cancer cases and 8.2 million cancer-related deaths occurred in 2012, compared with 12.7 million and 7.6 million, respectively, in 2008. It is estimated that in 2012, there were 32.6 million people (over the age of 15 years) alive who had had a cancer diagnosed in the previous five years. It is projected that 19.3 million new cancer cases per year are expected by 2025, which is due to growth and aging of the global population. According to the cancer facts & figures 2014 by the center of disease control (CDC) of USA, about 1,665,540 new cancer cases are expected to be diagnosed in USA and about 585,720 Americans are expected to die of cancer, almost 1,600 people per day in 2014. Obviously, there is an urgent need for effective therapeutic solutions to combat the cancers.

Most cancers (>90%) are derived from epithelial cells and the cancer related death are largely associated with cancer metastasis. Several genes have been identified to be associated with epithelial derived cancer metastasis including Cadherins and Dystroglycan. Increasing evidence suggested that various type of cancers found missing or dramatically reducing the FOG of α-DG on the cancer cell surfaces (Sgambato, Migaldi et al. 2003) (Sgambato, Camerini et al. 2007; Sgambato, De Paola et al. 2007). The FOG of α-DG expression level is reversely correlated with malignancy and progression of various types of cancer (Dobson, Hempel et al. 2012). The lack of the FOG of α-DG on cancer cells is due to silence of glycosyltransferases gene involved in the biosynthesis of the FOG of α-DG, such as LARGE in the cancer cells. But the detailed mechanism by which cells silence the gene expression remains unknown (de Bernabe, Inamori et al. 2009). However, restoration of the FOG of α-DG by introducing the corresponding silenced genes in the cancer cells can inhibit cancer cells growth and metastasis in mouse models (Bao, Kobayashi et al. 2009). Thus restoring the FOG of α-DG on cancer cells becomes a potential approach to treat metastatic cancers associated with loss of the FOG on the cell surfaces.

Therapy for Muscular Dystrophies

Up-to-date, there is no effective treatment for any types of MD except palliative therapy. The current efforts in drug discovery for DMD mainly based on exon skipping. The results obtained by several clinic trials are not effective and still in debate. In addition, exon skipping drug are oligo nucleotides based, which can only treats a group of specific mutations with limited scope of patients (<10% DMD). It has been reported that increasing glycosylation of α-DG can inhibit the dystrophic phenotypes in Mdx, dyW, or Sgca$^{-/-}$ MD mouse models by overexpressing a glycosyltransferase, Galgt2 in the mice (Nguyen, Jayasinha et al. 2002; Xu, Chandrasekharan et al. 2007; Xu, DeVries et al. 2009). As a means of increasing glycosylation of α-DG, U.S. Pat. No. 8,119,766, proposes introducing the LARGE (or LARGE2) gene to muscles, which are glycosyltransferases involved in the biosynthesis of the FOG of α-DG. However, such methods are limited by lack of effective means of delivering genes to human body. The promise of gene therapy has yet to be fulfilled due to multiple hurdles including poor uptake of the delivery vehicles and human immunological response to the gene therapeutic agents. Furthermore, the synthesis of the FOG of α-DG is a complicated process with more than a dozen genes direct involvement. The balance of the expression levels of the genes is critical for the concert biosynthesis. Simply overexpressing one of these genes may even has adverse impacts on the biosynthesis of the FOG of α-DG. In fact, independent reports suggested that overexpressing of the Large alone exacerbate the dystrophic phenotypes rather than benefit the MD mice with FKRP deficiency (Saito, Kanagawa et al. 2014) (Whitmore, Fernandez-Fuente et al. 2014). Thus new strategy to treat these diseases is much needed. Our strategy is to enhance the FOG of α-DG to strength the linkage between ECM to cytoskeleton and sarcolemma to treat various types of MD.

In mammalian, there are several linker proteins bridges DAGC to cytoskeleton such as dystrophin, utrophin, and plectins. In mdx mice, utrophin is up-regulated, which compensates the lack of dystrophin. Thus mdx mice have much milder dystrophic phenotypes compared to the human DMD patients and a normal life span, while in human there is no up-regulated utrophin in skeleton muscle. Double null of dystrophin and utrophin in mice closely resemble the clinic manifestations in human. Moreover, overexpressing of utrophin can inhibit dystrophic phenotype in mdx mice. These results suggested that alternative linker protein can compensate the defective linkage to a certain extent. Thus enhancing the connection between ECM to cytoskeleton in DMD with alternative linker protein is a promising avenue to treat DMD. However, it has been prove to be very difficult to do so. We discovered that enhancing the FOG of α-DG results in increasing the recruitment of a number of DAGC associated such as linker proteins dystrobrevin and plectin-1 to DAGC complex in muscle cells. It is conceivable that this recruitment would strength the linkage between ECM to the cytoskeleton and inhibit dystrophic phenotypes since DAGC play important roles in linking ECM to cytoskeletons and muscle function. Defects of this linkage is in common of various MDs, which has been illustrated that mutation of Dystrophin and Plectin-1 results in muscular dystrophies (Hoffman, Brown et al. 1987) (Smith, Eady et al. 1996; Rezniczek, Konieczny et al. 2007). Thus enhancing of FOG of α-DG may be an avenue to treat various MDs.

SUMMARY OF THE INVENTION

There is no effective treatment for any type of MD now and current cancer related death is still the major unmet medical challenge. Search for pharmaceutical compounds is the critical step to discover pharmaceutical solutions for these devastating diseases. Our strategy and approach to enhance FOG of α-DG on cell surfaces using small molecules to treat these diseases is the first of its kind and unique. The present invention provides the compounds defined by the formula (I) which can enhance the functional O-mannosylation of proteins including α-DG when administered to the cells. Also provided are the methods of preparation of the compounds. Also provided are the methods of using the compounds or the pharmaceutical acceptable salts or prodrugs thereof in treating and/or preventing subjects suffering from the diseases including muscular dystrophies and cancers.

In one aspect, the compounds that can enhance the functional O-mannosylation of proteins including α-DG are defined by the general formula-I:

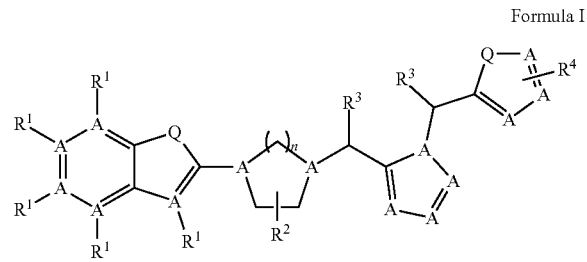

Formula I

Wherein:
1) A is independently Carbon or Nitrogen.
2) Q is independently O, S, NH, NW, $CH_2$, CHW, or $C(W)_2$, wherein: W is halogen (F, CI, Br. I), OH, NO2.
3) n is independently 1, 2, 3, 4, 5, 6, 7 or 8.
4) $R^1$ independently, are H, Cl, Br, F, I, OH, $NO_2$, COOH, NW, $C_{1-6}H_nW_m$, wherein: W is halogen (F, CI, Br. I), n=0-8, m=1-5, $C_{1-5}$acyl, $C_{1-5}$alkyl, $C_{1-5}$alkenyl, $C_{1-5}$alkynyl, $N_3$, CN, C(O)NH2, C(O)NH($C_{1-5}$acyl), C(O)NH($C_{1-5}$alkyl), C(O)O($C_{1-5}$alkyl), C(O)O($C_{1-5}$alkenyl), C(O)O($C_{1-5}$alkynyl), O($C_{1-5}$alkyl), O($C_{1-5}$alkenyl), O($C_{1-5}$alkynyl), S($C_{1-5}$alkyl), S($C_{1-5}$alkenyl), S($C_{1-5}$alkynyl), SO($C_{1-5}$alkyl), SO($C_{1-5}$alkenyl), SO($C_{1-5}$alkynyl), $SO_2$($C_{1-5}$alkyl), $SO_2$($C_{1-5}$alkenyl), $SO_2$($C_{1-5}$alkynyl), $O_3$S($C_{1-5}$acyl), $O_3$S($C_{1-5}$alkyl), $O_3$S($C_{1-5}$alkenyl), $O_3$S(alkynyl), $NH_2$, NH($C_{1-5}$alkyl), NH($C_{1-5}$alkenyl), NH($C_{1-4}$alkynyl), NH($C_{1-4}$acyl), amino acids, or biotin.
5) $R^2$ and $R^4$ independently, are H, OH, COOH, $SO_2$, $SO_3$, $SO_4$, $PO_3$, $PO_4$, CN, Cl, Br, F, I, $NO_2$, $NH_2$, NH($C_{1-8}$alkyl), NH($C_{1-8}$alkenyl), NH($C_{1-8}$alkynyl), NH($C_{1-8}$acyl), N($C_{1-8}$alkyl)$_2$, N($C_{1-8}$acyl)$_2$, O($C_{1-8}$acyl), O($C_{1-8}$alkyl), O($C_{1-8}$alkenyl), O($C_{1-8}$alkynyl), $OC_{1-4}H_nW_m$, wherein: W is halogen (F, CI, Br. I), n=0-8, m=1-5, S($C_{1-8}$acyl), S($C_{1-8}$alkyl), S($C_{1-8}$alkenyl), S($C_{1-4}$alkynyl), $C_{1-8}$alkyl, $C_{1-8}$acyl, $C_{1-8}$alkenyl, $C_{1-8}$alkynyl, $C_{1-6}H_nW_m$, wherein: W is halogen (F, CI, Br. I), n=0-8, m=1-5.
6) $R^3$, independently, are H, $N_3$, OH, $SO_2$, $SO_3$, $SO_4$, $PO_3$, $PO_4$, CN, Cl, Br, F, I, $NO_2$, $C_{1-4}$alkyl, $C_{1-4}$acyl, $C_{1-4}$alkenyl, $C_{1-4}$alkynyl, $NH_2$, NH($C_{1-4}$alkyl), NH($C_{1-4}$alkenyl), NH($C_{1-4}$alkynyl), NH($C_{1-4}$acyl), N($C_{1-4}$alkyl)$_2$, N($C_{1-4}$acyl)$_2$, O($C_{1-4}$acyl), O($C_{1-4}$alkyl), O($C_{1-4}$alkenyl), O($C_{1-4}$alkynyl), S($C_{1-4}$acyl), S($C_{1-4}$alkyl), S($C_{1-4}$alkenyl), S($C_{1-4}$alkynyl), or $C_{1-4}H_nW_m$, wherein W is halogen (F, CI, Br. I), n=1-8, m=1-5, or $OC_{1-4}H_nW_m$, wherein: W is halogen (F, CI, Br. I), n=1-8, m=1-5.

In one aspect, the present invention provides a method of enhancing the functional O-mannosylation of at least one protein includes α-DG in a cell. In certain embodiments, the method comprises contacting a cell with a compound of the invention, e.g., a compound selected from the group of compounds defined by the formula (I), or its pharmaceutically acceptable salts, or prodrugs. In certain embodiments, the cell is contacted in vitro. In other embodiments, the cell is contacted in vivo.

In another aspect, the invention provides the methods of treating a disease in a subject. In certain embodiments, the methods comprise administering to a subject a compound selected from the group of compounds defined by the formula (I), or its pharmaceutically acceptable salts or prodrugs. In preferred embodiments, the compound is administered with a pharmaceutically acceptable carrier. In certain embodiments, the disease is associated with muscular dystrophies including but not limited to dystroglycanopathies, DMD, BMD, LGMD, and CMD. In other embodiments, the disease is a certain type of cancer, which are associated with hypoglycosylation of α-DG as well.

BRIEF DESCRIPTION OF THE DRAWINGS

FIG. 1 is a graphical depiction of the dose-dependent enhancement of the functional O-mannosylation of α-DG on cell surfaces based on the treatment with the compound: 5-amino-7-fluoro-2-(4-(1-(1-(thiophen-2-ylmethyl)-1H-tetrazol-5-yl)propyl)piperazin-1-yl)benzothiazole (Mannan-007). The Chinese hamster ovary (CHO), mouse myoblasts (C2C12), normal human myoblasts (HSMB), human FKRP deficient myoblasts (FKRPD) were grown in 96 well-plates and treated with the compound at a series concentrations for 48 hours. The cells were examined with immuno-fluorescent staining using the IIH6 antibody that recognize the FOG of α-DG as the primary antibody followed by an appropriate secondary antibody conjugated with fluorophore. The detailed protocol is described in experiment section below.

DETAILED DESCRIPTION OF THE INVENTION

Various aspects and embodiments of the invention are now described in detail. As used throughout the description herein and claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. The terms used in this specification generally have their ordinary meanings in the art, within the context of the invention, and in the specific context where each term is used. Certain terms that are used to describe the invention are defined below, or elsewhere in the specification, to provide a clear guidance to the practitioner in describing the compositions and methods of the invention and how to make and use them. It will be appreciated that the same thing can be expressed in multiple ways. Consequently, alternative expressions may be used for any one or more of the terms discussed herein, nor is any special significance to be placed upon whether or not a term is elaborated or discussed herein. The use of examples anywhere in this description, including examples of any terms discussed herein, is illustrative only, and in no way limits the scope and meaning of the invention or of any exemplified term. Likewise, the invention is not limited to various embodiments given in this specification.

Definitions

The following definitions are provided to facilitate an understanding of the present invention:

As used herein, "about" or "approximately" shall generally mean within 10 percent, and preferably within 5 percent of a given value or range. Numerical quantities given herein are approximate, meaning that the term "about" or "approximately" can be inferred if not expressly stated.

As used herein, the term "functional glycosylation or functional O-mannosylation" refers to glycosylation or O-mannosylation modifications that facilitate the proper function of a protein.

As used herein, the term "independently" indicates that the variable, which is independently applied, varies independently from application to application. Thus, in a compound such as RXR, wherein R is "independently" carbon or nitrogen, both R can be carbon, both R can be nitrogen, or one R can be carbon and the other R1 nitrogen.

As used herein, the term "alkyl," unless otherwise specified, refers to a saturated straight, branched, or cyclic, primary, secondary, or tertiary hydrocarbon of typically $C_1$ to $C_{10}$, and specifically includes methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term includes both substituted and unsubstituted alkyl groups. Alkyl groups can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, or any other viable functional group that does not inhibit the pharmacological activity of this compound, either unprotected, or protected, as necessary, as known to those skilled in the art, for example, as taught in T. W. Greene and P. G. M. Wuts, "Protective Groups in Organic Synthesis," 3rd ed., John Wiley & Sons, 1999, hereby incorporated by reference.

The term "halogen" as used herein, includes chloro, bromo, iodo and fluoro.

The term "acyl" refers to a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen (F, Cl, Br, I), $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group.

The term "amino acids" includes naturally occurring and synthetic α, β γ or δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In a preferred embodiment, the amino acid is in the L-configuration. Alternatively, the amino acid can be a derivative of alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-leucinyl, β-isoleucinyl, β-prolinyl, β-phenylalaninyl, β-tryptophanyl, β-methioninyl, β-glycinyl, β-serinyl, β-threoninyl, β-cysteinyl, β-asparaginyl, β-glutaminyl, β-aspartoyl, β-glutaroyl, β-lysinyl, β-argininyl or β-histidinyl. When the term amino acid is used, it is considered to be a specific and independent disclosure of each of the esters of α, β γ or δ glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine in the D and L-configurations.

The term "biotin" includes naturally occurring and synthetic, and includes but is not limited to, biotins with linkers for conjugation to other molecules, which include but not limited to sulfo-NHS, sulfo-NHS—S—S, and NHS-LC.

The term "pharmaceutically acceptable salt or prodrug" is used throughout the specification to describe any pharmaceutically acceptable form (such as an ester, phosphate ester, salt of an ester or a related group) of a compound which, upon administration to a patient, provides the active compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

As used herein, the terms "therapeutic agent," "drug," "pharmaceutical agent" or any other similar term means any chemical or biological material or compound suitable for administration by methods known in the art, which induces a desired biological or pharmacological effect. Such effect may include but is not limited to (1) having a prophylactic effect on an subject, such as preventing a condition, disease, or infection, (2) alleviating a condition, disease, or infection, or a symptom thereof, including, for example, reducing muscle dystrophy, and/or (3) completely eliminating a condition, disease, or infection from the subject. The effects may be local, such as alleviating the dystrophic manifestation of MD on particular muscles, or it may be systemic.

As used herein, an "effective amount" means the amount of a therapeutic agent, bioactive agent, or drug that is sufficient to provide the desired local or systemic effect and performance at a reasonable risk/benefit ratio as would attend any medical treatment.

Compounds of the invention (e.g., compounds defined by the formula I or their pharmaceutically acceptable salts, prodrugs) can be mixed with a pharmaceutically acceptable carrier so as to produce a pharmaceutical composition. Pharmaceutical compositions are typically formulated for administration by a particular route (e.g., intramuscular, intravenous, intraperitoneal or, subcutaneous injection, transdermal, oral delivery; nasal administration; or topical application). Thus, an appropriate pharmaceutically acceptable carrier will depend upon the intended route of administration. Suitable methods for selecting pharmaceutically acceptable carriers and formulating pharmaceutical compositions, particularly compositions comprising small compounds as the active pharmaceutical ingredient, are well-known in the art.

The following examples will enable those skilled in the art to more clearly understand how to practice the present invention. It is to be understood that, while the invention has been described in conjunction with the preferred specific embodiments thereof, that which follows is intended to illustrate and not limit the scope of the invention. Other aspects of the invention will be apparent to those skilled in the art to which the invention pertains.

EXPERIMENTS

Cell-based HTS/HCS Assay System:

Protein glycosylation is a multiple-step process that requires a large number of proteins in the secretory pathway of the cells. Thus we chose cell-based assay because our goal is to identify enhancer the FOG of α-DG on the cell surfaces. The assay system is HTS/HCS friendly and can adapt to various cell lines including myotubes as well as various readout methods including AlphaScreen, fluorescence density and HCS/fluorescence imaging. The standard operation protocol (SOP) for adhesion cells is described below and the FIG. 1 illustrates the assay process using myoblasts as the controls and screening cells and the IIH6 antibody as the probe. Other adhesion cells such CHO (Chinese hamster ovary) cell line can be implemented into this assay by simply removing the differentiation step.

Cell cultures: All cells are cultured at 37° C., 5% CO2, in appropriate media (F-12 for epithelial cells and DMEM for myoblasts) supplement with 10-20% fetal calf serum (FCS) and 1% antibiotics. Two days before the experiments, cells will be seeded into 175 flask at a density of 10 million cells/flask respectively and incubate for 24 hours to reach 90% confluence. The cells will be detached with trypsin EDTA and suspended in the cell culture media. The cells will be counted and seeded into the multiple-well plates as desired. Myotubes formation: When the myoblasts reach confluence, change the growth media to differential media (DEME with 2% horse serum) and incubate for 4-5 days.

Laminin Binding Assay with Cells

The cells were seeded in 96- or 384-wells plates for overnight incubation. Then the cells were fixed and permeablized in 0.2% Triton X-100 in the laminin overlay buffer (LBB, 10 mM ethanolamine, 140 mM NaCl, 1 mM $MgCl_2$ and 1 mM $CaCl_2$, pH 7.4) for 8 min and blocked with 10% BSA for 1 hour at 37° C. Then 50 μl of 5 μg/ml laminins-DyLight-488 labeled in the LLB was incubated with the cells for 2 hours at 37° C. The plates were washed for 4 times and read with microplate reader for staining the LARGE-MYC, an immuno-staining experiment was conducted with the anti-MYC polyclonal antibody.

Laminin Clustering Assay

The cells were seeded in 96 well plates for overnight incubation. Then the cells were incubated with 50 μl of 5 μg/ml laminins-DyLight-488 labeled in LBB for 6 hours at 37° C. in cell culture incubator. The cells were washed with LLB twice and fixed. The cells were washed twice again and 50 μl LLB per well were added, and plates will be ready for microplate reading or capturing images with fluorescent microscopy.

Laminin Overlay Assay

The cell lysates were separated by SDS-PAGE gels and transferred to Nitrocellulose membranes. The membranes were blocked in 10% non-fat milk in LLB for 1 hour, and then incubated with 2.5 μg/ml laminin at 4° C. overnight. After washing with LLB 5×5 min the laminin binding to α-DG was detected by standard Immunoblotting as describe above with a laminin polyclonal antibody (Sigma) followed by a goat anti-mouse IgG-HRP secondary antibody.

Immuno-fluorescent Microscopy

The cells were fixed, permeablized, and then blocked with 10% BSA in PBS for 1 hour. The primary antibodies in PBS with 10% BSA were incubated with the cells for 1 hour at room temperature (22° C.) followed by addition of secondary antibodies conjugated with Alexa-488/594. After washing the cells with PBS for 2 times, the DAPI was used to stain the cells for 15 mins and wash 3 times with PBS. The images were captured with an inverted Olympus fluorescent microscope. For small compound localization experiment, the cells are incubated with the biotin conjugated compounds and then the cells were washed and incubated with streptavidin-Dye and then images will be captured to see the location of the compound-target-protein.

Synthesis Procedures

The following working examples of synthesis procedures provide a further understanding of the structures of the compounds presented in the present invention and the methods for synthesizing of the compounds. These examples are of illustrative purposes, and are not meant to limit the scope of the invention. Equivalent, similar or suitable solvents, reagents or reaction conditions may be substituted for those particular solvents, reagents or reaction conditions described without departing from the general scope of the method.

Synthesis of Triazole

Scheme for Triazole Synthesis

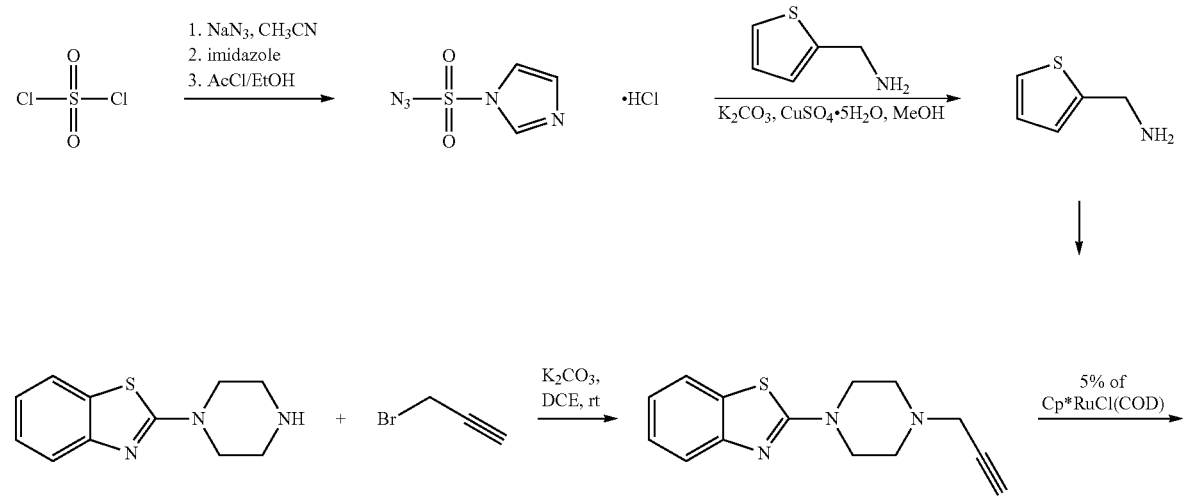

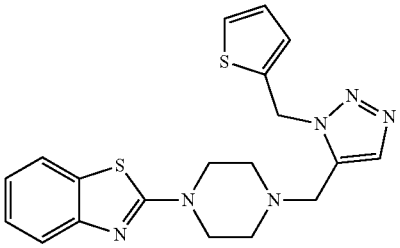 [SMILES: c1csc(Cn2nncc2CN2CCN(c3nc4ccccc4s3)CC2)c1]

2-(4-((1-(thiophen-2-ylmethyl)-1H-1,2,3-triazol-5-yl)methyl)piperazin-1-yl)benzothiazole

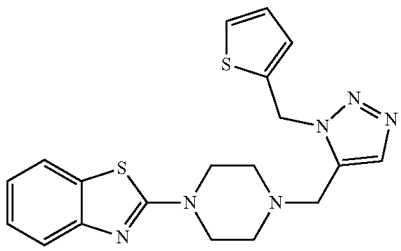

Cp*RuCl(COD) (30 mg, 10 mol %) was added to a flask with septum cap. The tube was sealed then evacuated and flushed with $N_2$ three times. 2.5 mL of toluene (degassed by vacuum for 5 min) as added, followed by 2-(4-(prop-2-yn-1-yl)piperazin-1-yl) benzothiazole (200 mg, 0.78 mmol) and 2-(azidomethyl) thiophene (108 mg, 0.78 mmol). The reaction was stirred at room temperature for 12 h, and TLC analysis indicated incomplete consumption of the starting materials. The crude was chromatographed with preparative TLC (DCM/Acetonitrile=5/1) to afford the product as a white solid. (24 mg, 8% yield)

LC-MS (ESI): $[M+1]^+$=397.15, $t_R$=3.90 min, 92% purity.

$^1$H NMR (400 MHz, CDCl$_3$) δ 7.61-7.55 (m, 3H), 7.32-7.27 (m, 2H), 7.09 (t, J=7.5 Hz, 1H), 7.02 (s, 1H), 6.98 (t, J=3.8 Hz, 1H), 5.86 (s, 2H), 3.62 (t, J=4.0 Hz, 4H), 3.55 (s, 1H), 2.53 (t, J=4.2 Hz, 4H).

$^{13}$C NMR (101 MHz, CDCl$_3$) δ 168.57, 152.59, 136.96, 134.91, 132.41, 130.75, 127.20, 126.30, 126.12, 121.66, 120.77, 119.23, 52.23, 50.54, 48.09, 47.11.

1. IV Synthesis of Isonitriles

General Scheme for Isonitrile Synthesis

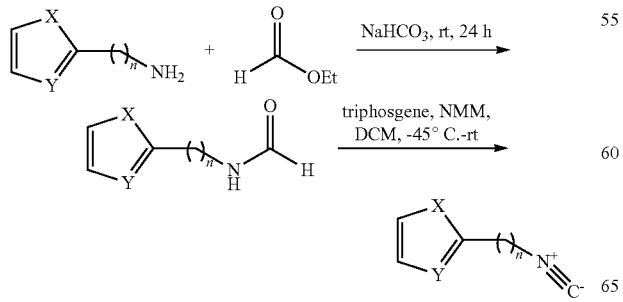

X=O or S
Y=C or N

General Procedure for Synthesis of Isonitrile (GP1) {Bondock, 2009 #820; Gupta, 2010 #737}

GP1-1: To amine (1.0 eq) at rt was added ethyl formate (2.5 volume), followed by addition of NaHCO$_3$. The mixture was stirred at rt for 24 h. After that, the solid was filtered off and the solvent was removed under reduced pressure to get the crude.

GP1-2: Substituted formamide (1.0 eq) in 3 volume of anhydrous DCM and NMM (2.3 eq) was added dropwise by thiphosgene (0.35 eq) in 6 volume of anhydrous DCM under $N_2$ and −45° C. condition over 20 min. Then the temperature was slowly warmed up to rt over 1 h. The mixture was quenched carefully by adding it to 2 M of Na$_2$CO$_3$ under 0° C. and organic layer was collected and concentrated to dryness with characteristic odor, which was used directly without further purification. It should be noted that the isonitrile is highly unstable under acidic condition.

N-(furan-2-ylmethyl)formamide

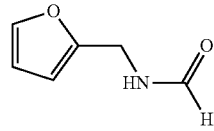

The title compound was prepared according to GP1-1. To furan-2-ylmethylamine (9.7 g, 0.1 mol) at rt was added ethyl formate (25 mL), followed by addition of NaHCO$_3$ (4 g). The mixture was stirred at rt for 24 h. After that, the solid was filtered off and the solvent was removed under reduced pressure to get light yellow oil (9.3 g, yield: 74%).

LC-MS (ESI): $[M+1]^+$=125.90, $t_R$=1.06 min.

$^1$H NMR (400 MHz, CDCl$_3$) δ minor isomer was observed and only the major was recorded herein, 8.13 (s, 1H), 7.33 (s, 1H), 7.04 (brs, 1H), 6.30 (s, 1H), 6.21 (s, 1H), 4.4 (d, J=5.6 Hz, 1H).

$^{13}$C NMR (100 MHz, CDCl$_3$) δ minor isomer was observed and only the major was recorded herein, 161.4, 150.8, 142.2, 110.5, 107.5, 34.95.

N-(thiophen-2-ylmethyl)formamide

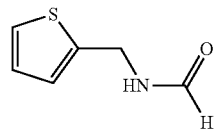

The title compound was prepared according to GP1-1. To 2-thiophene methylamine (10.0 g, 88.4 mmol) at rt was added ethyl formate (25 mL), followed by addition of NaHCO₃ (4 g). The mixture was stirred at rt for 24 h. After that, the solid was filtered off and the solvent was removed under reduced pressure to get oily product, which was triturated by PE/Et₂O (5/1) to get light yellow needle-like solid (10.5 g, 84% yield).

LC-MS (ESI): [M+1]⁺=141.90, $t_R$=2.09 min.

¹H NMR (400 MHz, CDCl₃) δ minor isomer was observed and only the major was recorded herein, 8.15 (s, 1H), 7.21 (d, J=4.8 Hz, 1H), 6.95-6.93 (m, 2H), 6.57 (brs, 1H), 4.60 (d, J=5.6 Hz, 1H).

¹³C NMR (100 MHz, CDCl₃) δ minor isomer was observed and only the major was recorded herein, 161.0, 140.3, 127.0, 126.2, 125.3, 36.8.

N-(2-(thiophen-2-yl)ethyl)formamide

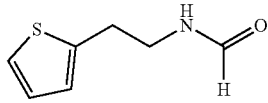

The title compound was prepared according to GP1-1. To 2-thiophene ethylamine (2.5 g, 20 mmol) were added ethyl formate (10 mL) and NaHCO₃ (1 g). The mixture was stirred at rt for overnight. Water was added, extracted by EA (2×25 mL), dried over Na₂SO₄, and concentrated under reduced pressure to get brown oil (3.0 g, 97% yield).

LC-MS (ESI): [M+1]⁺=156.20, $t_R$=0.43 min.

¹H NMR (400 MHz, CDCl₃) δ minor isomer was observed and only the major was recorded herein, 8.07 (s, 1H), 7.14 (d, J=5.1 Hz, 1H), 6.92 (dd, J=4.9, 3.6 Hz, 1H), 6.83 (d, J=2.5 Hz, 1H), 6.49 (brs, 1H), 3.53 (q, J=6.6 Hz, 2H), 3.03 (t, J=6.9 Hz, 2H)

¹³C NMR (100 MHz, CDCl₃) δ minor isomer was observed and only the major was recorded herein, 161.5, 141.0, 127.1, 125.4, 124.0, 39.5, 29.8.

2-(isocyanomethyl)furan

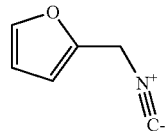

The title compound was prepared according to GP1-2. N-(furan-2-ylmethyl)formamide (2.5 g, 20 mmol) in 10 mL of anhydrous DCM and NMM (5.1 mL, 46 mmol) was added dropwise by thiphosgene (2.1 g, 7 mmol) in 15 mL of anhydrous DCM under N₂ and −45° C. condition over 20 min. Then the temperature was slowly warmed up to rt over 1 h. The mixture was quenched carefully by adding it to 2 M of Na₂CO₃ under 0° C. The organic layer was collected and dried to get yellow oil (2.0 g, 100% yield) with characteristic odor, which was used directly without further purification.

2-(isocyanomethyl)thiophene

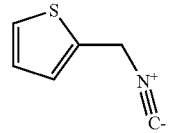

The title compound was prepared according to GP1-2. N-(thiophen-2-ylmethyl)formamide (10.5 g, 74.37 mmol) in 30 mL of anhydrous DCM and NMM (18.8 mL, 171.05 mmol) was added dropwise by thiphosgene (7.9 g, 26.77 mmol) in 60 mL of anhydrous DCM under nitrogen and −45° C. condition over 20 min. Then the temperature was slowly warmed up to rt over 1 h. The mixture was quenched carefully by adding it to 2 M of Na₂CO₃ under 0° C. The organic layer was collected, dried and purified by silica gel chromatography (PE/DCM=1/1) to give red oil (8.0 g, 88% yield).

¹H NMR (400 MHz, CDCl₃) δ 7.21 (d, J=5.2 Hz, 1H) 6.97 (s, 1H), 6.90 (dd, J=4.0 Hz, 1H), 4.66 (s, 1H).

¹³C NMR (100 MHz, CDCl₃) δ 156.9 (t, $^1J_{C-N}$=4.7 Hz), 133.4, 126.1, 125.9, 125.3, 39.5 (t, $^1J_{C-N}$=7.3 Hz).

2-(2-isocyanoethyl)thiophene

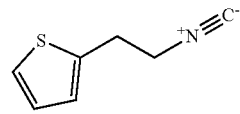

The title compound was prepared according to GP1-2. N-(2-(thiophen-2-yl)ethyl)formamide (3.0 g, 19.1 mmol) in 10 mL of anhydrous DCM and NMM (5 mL, 45.8 mmol) was added dropwise by thiphosgene (2.0 g, 6.9 mmol) in 20 mL of anhydrous DCM under nitrogen and −45° C. condition over 20 min. Then the temperature was slowly warmed up to rt over 1 h. The mixture was quenched carefully by adding it to 2 M of Na₂CO₃ under 0° C. The organic layer was collected, dried and purified by silica gel chromatography (PE/DCM=1/1) to give the product as red oil (2.5 g, 95% yield).

¹H NMR (400 MHz, CDCl₃) δ 7.17 (dd, J=5.0, 1.0 Hz, 1H), 6.94 (dd, J=4.8, 4.8 Hz, 1H), 6.90 (d, J=2.6 Hz, 1H), 3.58 (t, J=6.8 Hz, 2H), 3.15 (t, J=6.3 Hz, 2H).

¹³C NMR (100 MHz, CDCl₃) δ 157.3 (t, $^1J_{C-N}$=5.4 Hz), 138.56, 127.24, 126.24, 124.66, 43.2 (t, $^1J_{C-N}$=6.7 Hz), 29.96.

2-(isocyanomethyl)thiazole

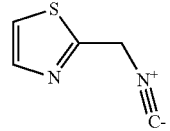

To 2-thiazole methylamine dihydrochloride (1.0 g, 5.4 mmol) were added ethyl formate (5 mL) and Et₃N (1.7 mL, 11.2 mmol). The mixture was stirred at rt for overnight. The mixture was diluted by EA, washed by 10% citric acid, extracted by EA (5×25 mL), dried over Na₂SO₄, and concentrated under reduced pressure to get 2-(isocyanomethyl)thiazole as dark oil (180 mg, 1.3 mmol, 24% yield), which was used directly for next step.

2-(isocyanomethyl)thiazole (180 mg, 1.3 mmol) in 2 mL of anhydrous DCM was added by NMM (343 μL, 3.1 mmol). When the mixture was cooled to −45° C., triphosgene (140 mg, 0.47 mmol) in 2 mL of anhydrous DCM was added dropwise. Then the temperature was slowly warmed up to rt over 1 h. The mixture was quenched carefully by adding it to 2 M of Na₂CO₃ under 0° C. and organic layer was collected, dried and purified by silica gel chromatography (PE/DCM=1/1) to give the product as reddish oil (100 mg, 62% yield).

2. V Synthesis of 2-chlorobenzothiazoles: Method A

General Scheme for 2-chlorobenzothiazoles Synthesis from Anilines

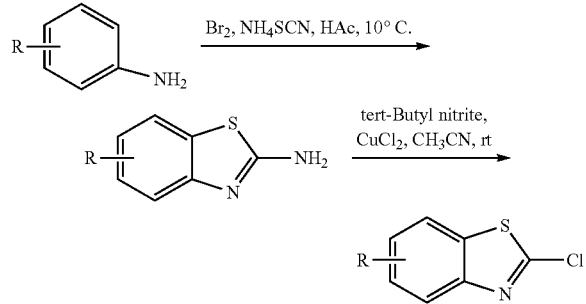

General Procedure of Method A for 2-chlorobenzothiazole Synthesis(GP2) {Bondock, 2009 #820; Gupta, 2010 #737}

GP2-1: In a flask were added by ammonium thiocyanate (2.2 eq) and HOAc (5 volume), bromine (1.1 eq) in HOAc (5 volume) was added dropwise under ice-cooled condition, which was stirred at 10° C. for 30 min. After filtering off the solid, the filtrate was collected.

In a separate flask, aniline (1.0 eq) and HOAc (5 volume) were added. Then the filtrate prepared above was added dropwise under 0° C. within 5 min. The mixture was kept stirring at rt overnight. After removal of solvent under reduced pressure, the residue was diluted with EA, neutralized with saturated Na₂CO₃ solution, separated, passed through a pad of Celite, and concentrated to dryness. The crude was purified by silica gel column.

GP2-2: To a round-bottomed flask was added 2-aminobenzothiazole (1.0 eq) and CuCl₂ (1.2 eq) in acetonitrile (10 volume), followed by slow addition of tert-butyl nitrite (1.2 eq). The gas evolved immediately. The reaction was greatly exothermic, and, if necessary, ice-water cooling was applied. The mixture was then stirred at rt for hours, which was monitored by TLC. After completion, the reaction was quenched by 1M HCl, washed by 1 M HCl twice and extracted by EA. The combined organic layer was washed by brine, dried over Na₂SO₄, concentrated and purified by flash column to give the product.

2-amino-5,6,7-trimethoxybenzothiazole

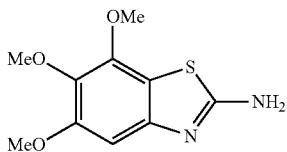 [SMILES: COc1cc2nc(N)sc2c(OC)c1OC]

The title compound was prepared according to GP2-1, and the crude was chromatographed (PE/EA=5/1 to 1/1 as eluent) to get grey solid. (690 mg, 18% yield)

LC-MS (ESI): [M+1]⁺=241.01, $t_R$=3.22 min.

¹H NMR (400 MHz, d6-DMSO) δ 7.35 (s, 2H), 6.79 (s, 1H), 3.88 (s, 3H), 3.79 (s, 3H), 3.71 (s, 3H).

¹³C NMR (101 MHz, d6-DMSO) δ 166.42, 159.82, 152.58, 148.96, 146.11, 135.88, 113.91, 97.97, 71.77, 60.80, 59.87, 55.99.

2-amino-4-nitrobenzothiazole

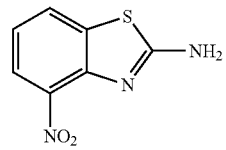 [SMILES: Nc1nc2c([N+](=O)[O-])cccc2s1]

The title compound was prepared according to GP2-1, and the crude was triturated by 10% EA in ether to get yellow solid. (4.0 g, 41% yield)

LC-MS (ESI): no mass observed, $t_R$=3.51 min.

¹H NMR (400 MHz, d6-DMSO) δ 8.27 (d, J=2.2 Hz, 1H), 7.84 (s, 2H), 7.65 (dd, J=9.0, 2.2 Hz, 1H), 7.13 (d, J=9.0 Hz, 1H).

¹³C NMR (101 MHz, DMSO) δ 147.11, 138.63, 130.61, 130.28, 121.39, 112.20, 107.44.

2-amino-4,6-difluorobenzothiazole

The title compound was prepared according to GP2-1, and the crude was triturated by ether to get light yellow powder. (1.6 g, 28% yield)

LC-MS (ESI): [M+1]⁺=187.40, $t_R$=3.19 min.

¹H NMR (400 MHz, DMSO) δ 7.71 (s, 1H), 7.54-7.43 (m, 1H), 7.18-7.05 (m, 1H).

¹³C NMR (101 MHz, DMSO) δ 166.64, 156.19 (dd, J=238.3, 10.7 Hz), 150.92 (dd, J=250.2, 13.3 Hz), 137.40 (dd, J=12.8, 2.4 Hz), 133.66 (dd, J=12.8, 6.7 Hz), 103.97 (dd, J=26.9, 4.0 Hz), 100.95 (dd, J=27.9, 22.7 Hz).

2-chloro-5,6,7-trimethoxybenzothiazole

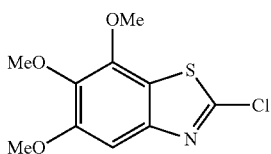 [SMILES: COc1cc2nc(Cl)sc2c(OC)c1OC]

The title compound was prepared according to GP2-2, and the crude was chromatographed (PE/EA=100/1 to 50/1 as eluent) to get the product as white powder. (377 mg, 51% yield)

LC-MS (ESI): [M+1]$^+$=259.99, $t_R$=4.12 min.

$^1$H NMR (400 MHz, CDCl$_3$) δ 7.21 (s, 1H), 4.06 (s, 3H), 3.93 (s, 3H), 3.91 (s, 3H).

$^{13}$C NMR (101 MHz, CDCl$_3$) δ 154.27, 152.50, 147.25, 146.23, 140.01, 121.21, 100.65, 61.43, 60.65, 56.32.

2-chloro-4-nitrobenzothiazole

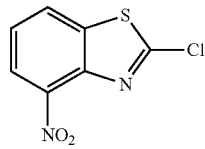

The title compound was prepared according to GP2-2 using 2-amino-4-nitrobenzothiazole (3.0 g, 15.37 mmol) and CuCl$_2$ (2.5 g, 18.44 mmol) in acetonitrile (30 mL), and tert-butyl nitrite (2.2 mL, 18.44 mmol). The crude was chromatographed (PE/EA=100/1 to 50/1 as eluent) to get the product as brown solid. (2.4 g, 73% yield)

LC-MS (ESI): no mass observed, $t_R$=3.79 min.

$^1$H NMR (400 MHz, CDCl$_3$) δ 8.05 (d, J=1.8 Hz, 1H), 7.75-7.66 (m, 2H).

$^{13}$C NMR (101 MHz, CDCl$_3$) δ 148.44, 133.71, 133.67, 128.72, 126.30, 125.32, 108.30.

2-chloro-4,6-difluorobenzothiazole

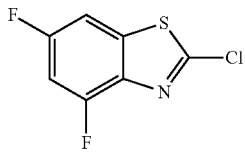 [SMILES: Fc1cc(F)c2nc(Cl)sc2c1]

The title compound was prepared according to GP2-2, and the crude was chromatographed (PE/EA=20/1 as eluent) to get the product as orange solid. (1.0 g, 57% yield)

LC-MS (ESI): no mass observed, $t_R$=4.02 min.

$^1$H NMR (400 MHz, CDCl$_3$) δ 7.30 (ddd, J=7.5, 2.3, 1.3 Hz, 1H), 7.05-6.97 (m, 1H).

$^{13}$C NMR (101 MHz, CDCl$_3$) δ 160.55 (dd, J=249.6, 10.2 Hz), 154.72 (dd, J=261.2, 13.3 Hz), 152.90 (d, J=2.8 Hz), 138.63 (dd, J=12.7, 4.6 Hz), 136.69 (dd, J=14.0, 2.7 Hz), 103.52 (dd, J=26.9, 4.9 Hz), 102.87 (dd, J=28.2, 21.6 Hz).

3. VI Synthesis of 2-chlorobenzothiazoles: Method B

General Scheme for 2-chlorobenzothiazoles Synthesis from 2-Halo substituted Anilines

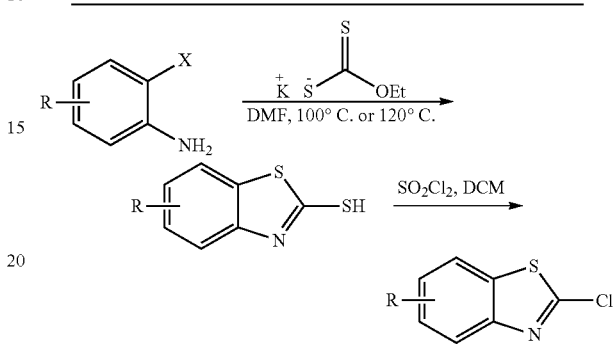

R=One or more substituted groups; X=Halo groups

General Procedure of Method B for 2-chlorobenzothiazoles Synthesis (GP3) {Zhu, 2004 #494; Zhu, 2005 #493}

GP3-1: A solution of 2-halo substituted aniline (1.0 eq), potassium ethyl xanthate (1.2 eq or 2.2 eq, typically 2.2 eq) In 10 volume of anhydrous DMF was heated at 100° C. or 120° C. for 4 hours under nitrogen. TLC monitored the progress of reaction. After completion, the reaction mixture was cooled to room temperature, diluted with water (10 volume) and neutralized by 1 M HCl solution to pH 5. The formed precipitate was collected by filtration, rinsed with water, firstly dried by rotavapor, and then dried by oil pump to afford 2-mercaptobenzothiazole.

GP3-2: 2-mercaptobenzothiazole in 10 volume of anhydrous DCM, was added by sulfuryl chloride (SO$_2$Cl$_2$, 1 volume) under ice-cooled condition. The mixture was stirred at rt for 1 hour, which was monitored by TLC. After consumption of starting material, the mixture was diluted by 30 volume of ether, following quenching carefully by adding water. Stirring was kept for 1 hour to make sure the SO$_2$Cl$_2$ was totally consumed and product was released. Organic layer was collected, neutralized by saturated NaHCO$_3$, dried over Na$_2$SO$_4$ and purified by silica gel chromatograph to give the pure product, which was finally characterized by LC-MS and NMR.

2-mercapto-7-fluorobenzothiazole

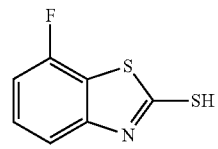 [SMILES: Fc1cccc2nc(S)sc12]

The title compound was prepared according to GP3-1 using 2,3-difluoroaniline (3.0 g, 23.5 mmol), potassium ethyl xanthate (8.2 g, 51.0 mmol) and DMF (30 mL). Water was added to precipitate the product as off-white solid. (4.3 g, 100% yield)

LC-MS (ESI): [M+1]$^+$=185.77, $t_R$=3.65 min.

¹H NMR (400 MHz, d6-DMSO) δ 14.07 (s, 1H), 7.46 (td, J=8.2, 5.6 Hz, 1H), 7.23-7.16 (m, 2H).
¹³C NMR (101 MHz, d6-DMSO) δ 189.34, 154.34 (d, J=244.5 Hz), 143.52 (d, J=6.6 Hz), 129.13 (d, J=7.8 Hz), 115.67 (d, J=22.9 Hz), 110.14 (d, J=18.7 Hz), 108.94 (d, J=3.4 Hz).

2-mercaptothiazolo[5,4-b]pyridine

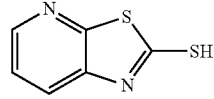

The title compound was prepared according to GP3-1 using 2-chloro-3-aminopyridine (5.0 g, 38.9 mmol), potassium ethyl xanthate (13.7 g, 85.6 mmol) and DMF (30 mL). Water was added to precipitate the product as off-white solid (6.2 g, 95% yield)
LC-MS (ESI): [M+1]⁺=168.85, $t_R$=2.98 min.
¹H NMR (400 MHz, DMSO) δ 13.96 (s, 1H), 8.42 (d, J=4.4 Hz, 1H), 7.64 (d, J=8.0 Hz, 1H), 7.44 (dd, J=7.9, 4.9 Hz, 1H).
¹³C NMR (101 MHz, DMSO) δ 188.70, 151.30, 145.59, 136.15, 122.21, 119.31.

2-mercapto-5-fluorobenzothiazole

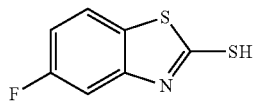

The title compound was prepared according to GP3-1 using 2,5-difluoroaniline (3.0 g, 23.2 mmol), potassium ethyl xanthate (8.2 g, 51.0 mmol) and DMF (30 mL). Water was added to precipitate the product as off-white solid (1.7 g, 40% yield)
LC-MS (ESI): [M+1]⁺=185.84, $t_R$=3.49 min.
¹H NMR (400 MHz, DMSO) δ 13.85 (s, 1H), 7.74 (dd, J=8.8, 5.2 Hz, 1H), 7.19 (td, J=9.1, 2.5 Hz, 1H), 7.09 (dd, J=9.1, 2.5 Hz, 1H).
¹³C NMR (101 MHz, DMSO) δ 191.43, 161.44 (d, J=242.8 Hz), 142.06 (d, J=12.1 Hz), 124.93, 123.24 (d, J=9.8 Hz), 111.72 (d, J=23.9 Hz), 99.66 (d, J=27.2 Hz).

2-mercapto-5-nitrobenzothiazole

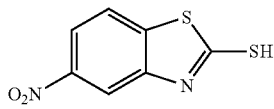 [SMILES: O=[N+]([O-])c1ccc2sc(S)nc2c1]

The title compound was prepared according to GP3-1 using 2-chloro-5-nitroaniline (3.5 g, 20.0 mmol), potassium ethyl xanthate (3.9 g, 24.0 mmol) and DMF (30 mL), heating at 100° C. for 4 h. Water was added to precipitate the product as yellow solid. (2.6 g, 62% yield)
LC-MS (ESI): no mass observed, $t_R$=3.55 min.

¹H NMR (400 MHz, d6-DMSO) δ 14.09 (brs, 1H), 8.14-8.11 (m, 1H), 7.95-7.94 (m, 2H).
¹³C NMR (101 MHz, d6-DMSO) δ 191.5, 146.4, 141.5, 137.1, 122.6, 118.7, 106.7.

2-mercapto-4-fluorobenzothiazole

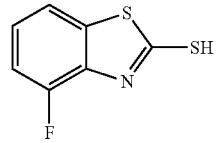 [SMILES: Fc1cccc2sc(S)nc12]

The title compound was prepared according to GP3-1 using 2,6-difluoroaniline (2.0 g, 15.5 mmol), potassium ethyl xanthate (5.5 g, 34.1 mmol) and DMF (20 mL), heating at 120° C. for 3.5 h. Water was added to precipitate the product as off-white powder. (2.8 g, 98% yield)
LC-MS (ESI): [M+1]⁺=185.94, $t_R$=3.50 min.
¹H NMR (400 MHz, DMSO) δ 14.22 (s, 1H), 7.52 (d, J=6.3 Hz, 1H), 7.36-7.24 (m, 2H).
¹³C NMR (101 MHz, DMSO) δ 190.66, 146.83 (d, J=249.0 Hz), 131.68 (d, J=3.3 Hz), 129.55 (d, J=15.0 Hz), 124.95 (d, J=6.4 Hz), 117.65 (d, J=3.7 Hz), 113.13 (d, J=16.6 Hz).

Scheme for Synthesis of 2-fluoro-3-bromoaniline

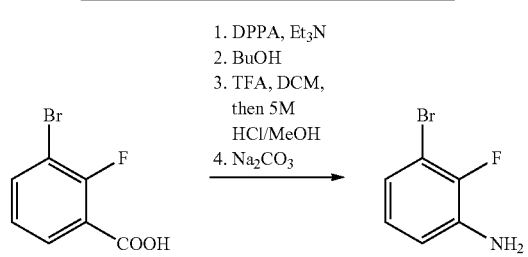

3-bromo-2-fluoroaniline

To 3-bromo-2-fluorobenzoic acid (10.0 g, 45.7 mmol) in 100 mL of toluene, were added by Et₃N (7.7 mL, 54.8 mmol) and DPPA (15.0 g, 54.8 mmol). The mixture was heated to 100° C. When gas evolved, t-BuOH (10 mL) was added and stirring was kept for additional 2 hours. The mixture was cooled down and washed successively by saturated Na₂CO₃ solution, 10% citric acid and brine. The organic layer was collected, dried over Na₂SO₄ and concentrated to get the N-Boc protected intermediate, which was used directly for next step.

The crude suspended in 30 mL of DCM, was added by TFA (15 mL). The mixture was then stirred at rt for 2 hours. The resulting solid was filtered off and 5 M of HCl/MeOH was added to the filtrate, forming the yellow solid, which was collected and neutralized by saturated $Na_2CO_3$ solution to get free base as brown oil. (6.5 g, 71% yield)

LC-MS (ESI): $[M+1]^+$=189.91, $t_R$=3.67 min.

$^1$H NMR (400 MHz, $CDCl_3$) δ 6.83-6.75 (m, 1H), 6.70 (t, J=8.0 Hz, 1H), 6.60 (t, J=7.9 Hz, 1H), 3.72 (s, 1H).

$^{13}$C NMR (101 MHz, $CDCl_3$) δ 148.18 (d, J=238.9 Hz), 135.76 (d, J=13.6 Hz), 125.12 (d, J=4.4 Hz), 122.05, 115.82 (d, J=3.4 Hz), 109.05 (d, J=18.1 Hz).

2-mercapto-7-bromobenzothiazole

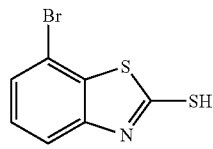

The title compound was prepared according to GP3-1 using 3-bromo-2-fluoroaniline (3.8 g, 20.0 mmol), potassium ethyl xanthate (7.1 g, 44.0 mmol) and DMF (40 mL), heating at 120° C. for 3 h. Water was added to precipitate the product as off-white powder. (4.9 g, 100% yield)

$^1$H NMR (400 MHz, DMSO) δ 14.03 (s, 1H), 7.50 (d, J=7.6 Hz, 1H), 7.36 (t, J=7.8 Hz, 1H), 7.31 (d, J=8.0 Hz, 1H).

$^{13}$C NMR (101 MHz, DMSO) δ 188.70, 141.66, 130.72, 128.96, 126.53, 112.74, 111.59.

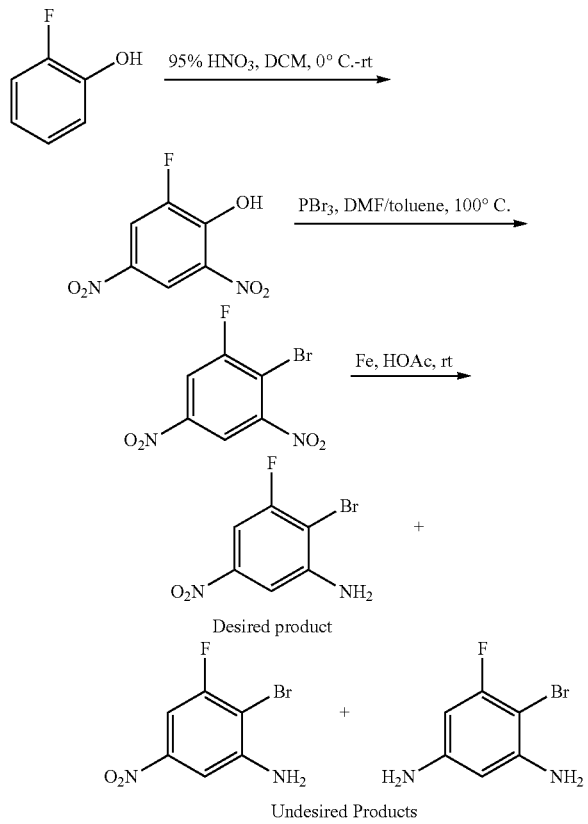

2-bromo-3-fluoro-5-nitroaniline

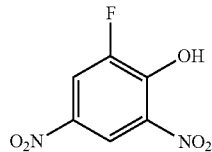

To 2 fluorophenol (11.2 g, 100 mmol) in DCM (100 mL) at 0° C. was added 95% $HNO_3$ (10 mL, 250 mmol) dropwise within 15 min. After 2 h, water was added, organic layer was separated, and aqueous layer was extracted by DCM (2×50 mL). The collected organic layer was washed by saturated brine, dried over anhydrous $Na_2SO_4$ and concentrated to give the product (15.4 g, 76%) as light orange solid.

LC-MS (ESI): $[M-1]^-$=200.8, $t_R$=3.28 min.

$^1$H NMR (400 MHz, $CDCl_3$) δ 10.96 (s, 1H), 8.91 (dd, J=9.2, 2.4, 2.0 Hz, 1H), 8.32 (dd, J=9.2, 2.8 Hz, 1H).

$^{13}$C NMR (101 MHz, $CDCl_3$) δ 152.0 (d, J=257.9 Hz), 149.7 (d, J=15.1 Hz), 138.5, 133.6, 117.9 (d, J=22.4 Hz), 116.7 (d, J=3.7 Hz).

2-bromo-1-fluoro-3,5-dinitrobenzene

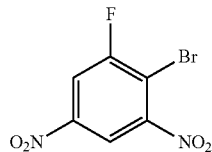

To a solution of 4,6-difluorophenol (10.1 g, 50 mmol) in DMF (20 mL) and toluene (150 mmol), $PBr_3$ (5.7 mL, 60 mmol) was added at rt. Then the reaction was heated at 100° C. for 1 hour. After cooling to rt, the supernatant was collected and the residue was extracted by toluene. Combined organic lays were washed by 1 M NaOH, dried over $Na_2SO_4$, and evaporated to dryness to give the product (12.9 g, 97%) as light yellow solid.

LC-MS (ESI): $[M-Br+OH-1]^-$=200.8, $t_R$=3.86 min.

$^1$H NMR (400 MHz, $CDCl_3$) δ 8.57 (dd, J=2.4, 1.6 Hz, 1H), 8.24 (dd, J=7.2, 2.5 Hz, 1H).

$^{13}$C NMR (101 MHz, $CDCl_3$) δ 159.9 (d, J=256.5 Hz), 150.8, 147.2, 116.1 (d, J=3.9 Hz), 114.7 (d, J=28.4 Hz), 111.8 (d, J=25.7 Hz).

2-bromo-3-fluoro-5-nitroaniline

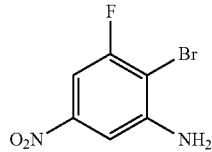 [SMILES: O=[N+]([O-])c1cc(F)c(Br)c([N+](=O)[O-])c1]

A mixture of 2-bromo-1,5-dinitro-3-fluorobenzlene (12.9 g, 48.7 mmol) and iron powder (8.2 g, 146.1 mmol) in 100 mL HOAc was stirred at rt. The resulting solid was filtered off and the filtrate was concentrated under reduced pressure.

The residue was diluted with EA, neutralized by 1 M NaOH and extracted with EA (2×100 mL). Collected organic layer was dried over Na$_2$SO$_4$, evaporated and purified by silica gel (eluent: PE/EA=5/1), collecting the first fraction as the product (4.2 g, 37%), the yellow solid.

LC-MS (ESI): [M−1]$^−$=232.8, t$_R$=3.76 min.

$^1$H NMR (400 MHz, MeOD) δ 7.46 (dd, J=2.5, 1.5 Hz, 1H), 7.21 (dd, J=8.5, 2.6 Hz, 1H).

$^{13}$C NMR (101 MHz, MeOD) δ 160.9 (d, J=244.8 Hz), 149.8 (d, J=3.9 Hz), 149.6 (d, J=11.0 Hz), 105.6 (d, J=2.2 Hz), 102.0 (d, J=23.5 Hz), 99.0 (d, J=29.0 Hz).

2-mercapto-7-fluoro-5-nitrobenzothiazole

The title compound was prepared according to GP3-1 using 2-bromo-3-fluoro-5-nitroaniline (3.7 g, 15.7 mmol), potassium ethyl xanthate (5.6 g, 34.6 mmol) and DMF (40 mL). Water was added to precipitate the product as yellow solid (3.6 g, 99% yield).

LC-MS (ESI): [M−1]$^−$=228.9, t$_R$=3.87 min.

$^1$H NMR (400 MHz, d6-DMSO) δ 8.02 (dd, J=9.2, 1.8 Hz, 1H), 7.72 (d, J=1.6 Hz, 1H).

$^{13}$C NMR (101 MHz, d6-DMSO) δ 190.13, 153.15 (d, J=248.4 Hz), 147.35 (d, J=8.8 Hz), 143.17 (d, J=7.4 Hz), 123.52 (d, J=23.0 Hz), 105.78 (d, J=24.8 Hz), 103.60 (d, J=3.1 Hz).

2-chloro-6-nitrobenzothiazole

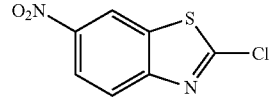 [SMILES: O=[N+]([O-])c1ccc2nc(Cl)sc2c1]

2-chlorobenzothiazole (8.0 g, 47.16 mmol) placed in a 100 mL of three-necked flask was added by concentrated H$_2$SO$_4$ (40 mL) carefully under 0° C. At 0° C. KNO$_3$ (5.0 g, 49.52 mmol) was added portionwise and kept stirring for 1 hour. The mixture was then poured into ice-water (100 mL). The precipitate was collected, washed with NaHCO$_3$ solution, dissolved into 200 mL of DCM, dried over Na$_2$SO$_4$ and triturated by EtOH (80 mL) to get the desired product as light yellow solid. (6.5 g, 64% yield)

LC-MS (ESI): no mass observed, t$_R$=3.90 min.

$^1$H NMR (400 MHz, CDCl$_3$) δ 8.75 (s, 1H), 8.38 (d, J=9.0 Hz, 1H), 8.07 (d, J=8.9 Hz, 1H).

$^{13}$C NMR (101 MHz, CDCl$_3$) δ 158.77, 154.75, 145.43, 136.47, 123.33, 122.24, 117.69.

2-chloro-7-fluorobenzothiazole

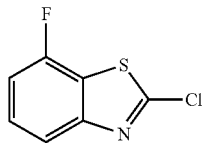 [SMILES: Fc1cccc2nc(Cl)sc12]

The title compound was prepared according to GP3-2, which was purified by flash column chromatography using PE/EA (20/1) as eluent to give the colorless oil. (420 mg, 22% yield)

$^1$H NMR (400 MHz, CDCl$_3$) δ 7.76 (d, J=8.2 Hz, 1H), 7.45 (td, J=8.1, 5.9 Hz, 1H), 7.14 (t, J=8.7 Hz, 1H).

$^{13}$C NMR (101 MHz, CDCl$_3$) δ 156.11 (d, J=250.1 Hz), 154.27, 153.45 (d, J=2.8 Hz), 127.63 (d, J=7.3 Hz), 123.25 (d, J=17.6 Hz), 118.80 (d, J=3.7 Hz), 111.41 (d, J=18.3 Hz).

2-chlorothiazolo[5,4-b]pyridine

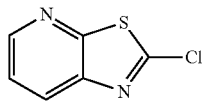

The title compound was prepared according to GP3-2, which was purified by crystallization from EtOH to give the light yellow solid. (1.8 g, 71% yield)

LC-MS (ESI): [M+1]$^+$=170.80, t$_R$=3.42 min.

$^1$H NMR (400 MHz, CDCl$_3$) δ 8.58 (dd, J=4.4, 1.2 Hz, 1H), 8.19 (dd, J=8.2, 1.3 Hz, 1H), 7.45 (dd, J=8.2, 4.7 Hz, 1H).

$^{13}$C NMR (101 MHz, CDCl$_3$) δ 158.72, 154.42, 147.54, 144.82, 129.84, 122.01.

2-chloro-5-fluorobenzothiazole

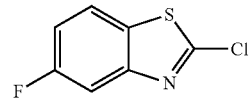 [SMILES: Fc1ccc2sc(Cl)nc2c1]

The title compound was prepared according to GP3-2, as off-white solid. (900 mg, 51% yield)

$^1$H NMR (400 MHz, CDCl$_3$) δ 7.72 (dd, J=8.9, 5.0 Hz, 1H), 7.64 (dd, J=9.1, 2.4 Hz, 1H), 7.20 (td, J=8.8, 2.5 Hz, 1H).

$^{13}$C NMR (101 MHz, CDCl$_3$) δ 161.94 (d, J=244.9 Hz), 155.49, 151.81 (d, J=12.1 Hz), 131.46 (d, J=2.3 Hz), 121.94 (d, J=9.7 Hz), 114.55 (d, J=25.0 Hz), 109.45 (d, J=24.2 Hz).

2-chloro-5-nitrobenzothiazole

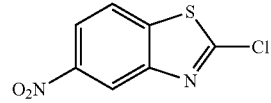 [SMILES: O=[N+]([O-])c1ccc2sc(Cl)nc2c1]

The title compound was prepared according to GP3-2, as white solid. (1.0 g, 38% yield)

LC-MS (ESI): no mass observed, $t_R$ 4.02 min.

$^1$H NMR (400 MHz, CDCl$_3$) δ 8.79 (d, J=1.7 Hz, 1H), 8.32 (dd, J=8.8, 1.9 Hz, 1H), 7.96 (d, J=8.8 Hz, 1H).

$^{13}$C NMR (101 MHz, CDCl$_3$) δ 156.82, 150.81, 147.16, 142.51, 121.76, 120.33, 118.35.

2-chloro-4-fluorobenzothiazole

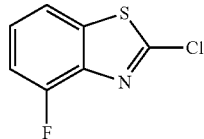 [SMILES: Fc1cccc2sc(Cl)nc12]

The title compound was prepared according to GP3-2, as white powder. (1.0 g, 67% yield)

LC-MS (ESI): no mass observed, $t_R$ 4.00 min.

$^1$H NMR (400 MHz, CDCl$_3$) δ 7.43 (d, J=8.1 Hz, 1H), 7.26 (td, J=8.0, 4.9 Hz, 1H), 7.07 (t, J=9.1 Hz, 1H).

$^{13}$C NMR (101 MHz, CDCl$_3$) δ 155.02 (d, J=257.8 Hz), 153.74, 139.79 (d, J=14.1 Hz), 138.49 (d, J=3.2 Hz), 126.74 (d, J=7.1 Hz), 116.84 (d, J=4.5 Hz), 112.55 (d, J=17.8 Hz).

7-bromo-2-chlorobenzothiazole

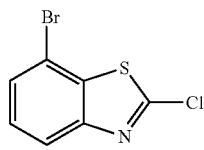 [SMILES: Clc1nc2cccc(Br)c2s1]

The title compound was prepared according to GP3-2, as white powder. (4.3 g, 86% yield)

LC-MS (ESI): no mass observed, $t_R$ 4.41 min.

$^1$H NMR (400 MHz, CDCl$_3$) δ 7.87 (d, J=8.1 Hz, 1H), 7.52 (d, J=7.8 Hz, 1H), 7.36 (t, J=8.0 Hz, 1H).

$^{13}$C NMR (101 MHz, CDCl$_3$) δ 153.42, 150.88, 138.97, 128.50, 127.84, 121.69, 113.13.

2-chloro-7-fluoro-5-nitrobenzothiazole

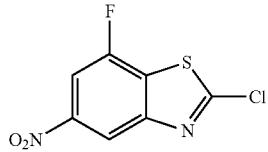 [SMILES: O=[N+]([O-])c1cc(F)c2sc(Cl)nc2c1]

The title compound was prepared according to GP3-2, which was purified by flash column chromatography using PE/EA (20/1) as eluent.

$^1$H NMR (400 MHz, CDCl$_3$) δ 8.66 (d, J=1.8 Hz, 1H), 8.06 (dd, J=8.9, 1.9 Hz, 1H).

$^{13}$C NMR (101 MHz, CDCl$_3$) δ 157.52 (d, J=2.1 Hz), 155.29 (d, J=254.9 Hz), 152.53 (d, J=3.4 Hz), 147.68 (s), 130.05 (d, J=17.6 Hz), 114.66 (d, J=3.9 Hz), 106.93 (d, J=24.0 Hz).

4. VII Synthesis of Tetrazole

Scheme for Synthesis of Tetrazole

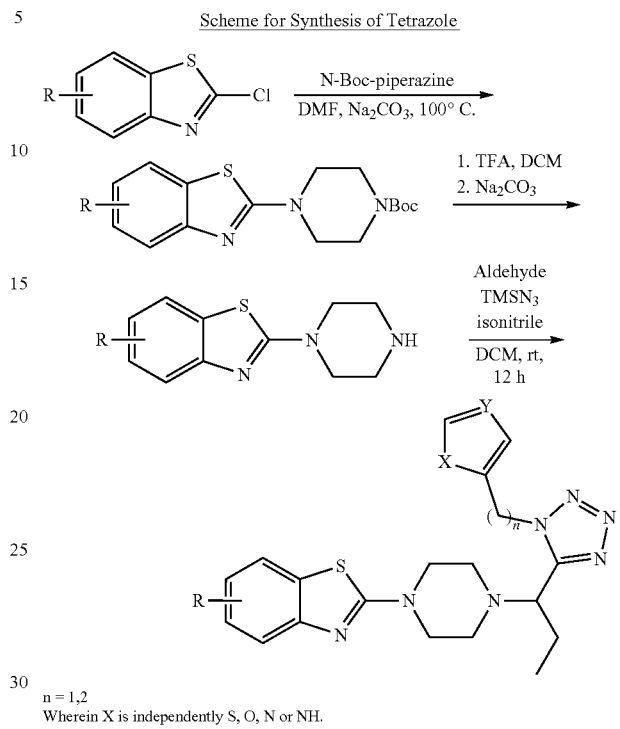

n = 1,2
Wherein X is independently S, O, N or NH.

General Procedure of Amine Synthesis (GP4)

GP4-1: A mixture of substituted 2-chlorobenzothiazole (1.0 eq), N-Boc piperazine (1.05 eq) and Na$_2$CO$_3$ (1.2 eq) in DMF (10 volume) was heated up at 100° C. for hours, the process of which was monitored by TLC. The mixture was diluted by EA and added by water. After extraction by EA (2 times), the collected organic layers were washed by 10% citric acid, and then brine, dried over Na$_2$SO$_4$ and concentrated to give crude product, which could be used directly without further purification.

GP4-2: N-Boc protected amine in DCM (5 volume) was added by TFA (2.5 volume). The mixture was stirred at rt for four hours and monitored by TLC. After consumption of starting material, volatile solvent was removed under reduced pressure and the residue was neutralized by saturated Na$_2$CO$_3$ solution to obtain the slurry, which was extracted by 10% methanol in DCM (3 times). The organic layers were collected, dried and concentrated to give the desired free amine, for direct use for next step.

GP4-3: Free amine (1.0 eq) suspended in DCM (10 volume) was added by aldehyde (1.1 eq) under N$_2$ atmosphere. The mixture was stirred at rt 15 min. Then trimethylsilyl azide (TMSN$_3$, 1.1 eq) was added, and stirring was kept for another 15 min, followed by addition of isonitrile (1.0 eq). The mixture was stirred at for 12 h. After removal of solvent, the residue was purified by preparative TLC (DCM/MeOH as eluent) to give the product, which could be re-purified by trituration with ether.

tert-butyl 4-(benzothiazol-2-yl)piperazine-1-carboxylate

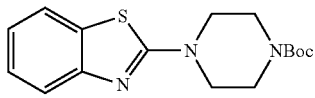

The title compound was prepared according to GP4-1 as off-white solid (11.4 g, 61% yield), which was used without further purification.

LC MS (ESI): [M+1]$^+$=320.21, $t_R$=4.24 min.

tert-butyl 4-(benzoxazol-2-yl)piperazine-1-carboxylate

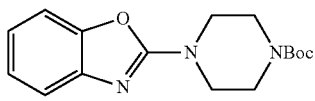 [SMILES: CC(C)(C)OC(=O)N1CCN(c2nc3ccccc3o2)CC1]

2-chlorobenzoazole (5.0 g, 32.6 mmol) was added to a suspension of N-Boc piperazine in chloroform (70 mL) at 0° C. within 15 min. The mixture then was stirred at rt overnight. After filtering off the solid, the filtrate was dried under reduced pressure to give the crude, which was used without further purification.

tert-butyl 4-(1H-benzimidazol-2-yl)piperazine-1-carboxylate

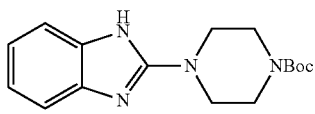 [SMILES: CC(C)(C)OC(=O)N1CCN(c2nc3ccccc3[nH]2)CC1]

A mixture of 2-chrolobenzimidazole (3.0 g, 20 mmol) and N-tert-butoxycarbonyl piperazine (3.7 g, 20 mmol) in 1-butanol (40 mL) was heated to reflux for 3 hours. The resulting solid was collected, rinsed with ether and dried over high vacuum. (5.0 g, 83% yield)

LC-MS (ESI): [M+1]$^+$=302.23, $t_R$=3.33 min.

$^1$H NMR (400 MHz, MeOD) δ 7.44-7.41 (m, 2H), 7.36-7.28 (m, 2H), 3.69 (s, 8H), 1.50 (s, 9H).

$^{13}$C NMR (101 MHz, MeOD) δ 156.01, 151.68, 131.22, 125.24, 112.55, 82.12, 47.25, 28.60.

tert-butyl 4-(6-fluorobenzothiazol-2-yl)piperazine-1-carboxylate

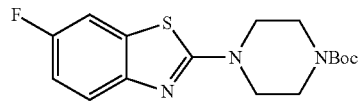

The title compound was prepared according to GP4-1, white powder. (1.8 g, 100% yield)

LC-MS (ESI): [M+1]$^+$=338.12, $t_R$=4.32 min.

$^1$H NMR (400 MHz, CDCl$_3$) δ 7.48 (dd, J=8.8, 4.7 Hz, 1H), 7.32 (dd, J=8.1, 2.6 Hz, 1H), 7.03 (td, J=9.0, 2.6 Hz, 1H), 3.59 (s, 8H), 1.49 (s, 9H).

$^{13}$C NMR (101 MHz, CDCl$_3$) δ 168.25, 158.22 (d, J=240.4 Hz), 154.55, 148.96, 131.38 (d, J=10.7 Hz), 119.72 (d, J=8.8 Hz), 113.81 (d, J=23.8 Hz), 107.52 (d, J=27.0 Hz), 80.46, 48.21, 28.39.

tert-butyl 4-(6-methoxybenzothiazol-2-yl)piperazine-1-carboxylate

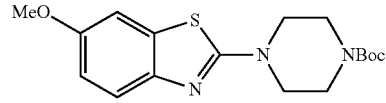

The title compound was prepared according to GP4-1, off-white solid. (2.0 g, 93% yield)

$^1$H NMR (400 MHz, CDCl$_3$) δ 7.47 (d, J=8.8 Hz, 1H), 7.15 (d, J=2.6 Hz, 1H), 6.91 (dd, J=8.8, 2.6 Hz, 1H), 3.82 (s, 3H), 3.57 (s, 8H), 1.49 (s, 9H).

$^{13}$C NMR (101 MHz, CDCl$_3$) δ 167.28, 155.22, 154.58, 146.71, 131.72, 119.74, 113.76, 105.22, 80.34, 55.87, 48.26, 28.39.

tert-butyl 4-(6-chlorobenzothiazol-2-yl)piperazine-1-carboxylate

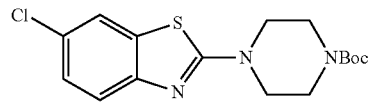

The title compound was prepared according to GP4-1, off-white solid. (1.6 g, 92% yield)

LC-MS (ESI): [M+1]$^+$=354.12, $t_R$=4.51 min.

$^1$H NMR (400 MHz, CDCl$_3$) δ 7.56 (dd, J=7.9, 1.9 Hz, 1H), 7.44 (dd, J=8.5, 6.5 Hz, 1H), 7.27-7.21 (m, 1H), 3.58 (s, 8H), 1.48 (d, J=4.5 Hz, 9H).

$^{13}$C NMR (101 MHz, CDCl$_3$) δ 168.67, 154.49, 151.22, 131.90, 126.72, 126.54, 120.41, 119.90, 80.44, 48.20, 28.38.

tert-butyl 4-(6-methylbenzothiazol-2-yl)piperazine-1-carboxylate

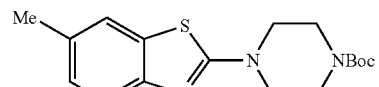

The title compound was prepared according to GP4-1, off-white solid. (2.43 g, 96% yield)

$^1$H NMR (400 MHz, CDCl$_3$) δ 7.45 (d, J=8.2 Hz, 1H), 7.41 (s, 1H), 7.11 (d, J=8.2 Hz, 1H), 3.58 (s, 8H), 2.39 (s, 3H), 1.49 (s, 9H).

$^{13}$C NMR (101 MHz, CDCl$_3$) δ 168.13, 154.58, 150.38, 131.44, 130.79, 127.28, 120.80, 118.91, 80.35, 48.23, 28.40, 21.23.

Scheme for Synthesis of tert-butyl 4-(6-phenylbenzothiazol-2-yl)piperazine-1-carboxylate

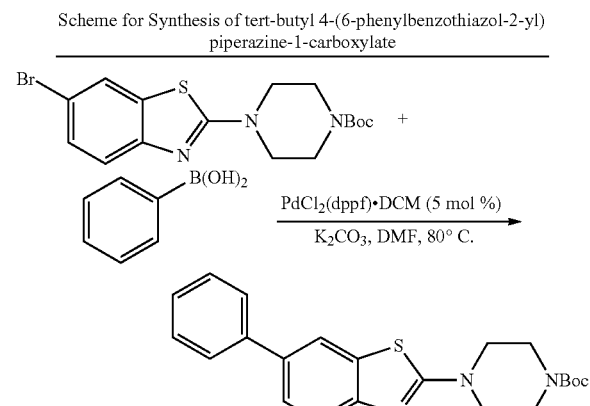

tert-butyl 4-(6-bromobenzothiazol-2-yl)piperazine-1-carboxylate

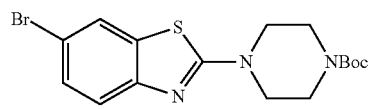 [SMILES: CC(C)(C)OC(=O)N1CCN(c2nc3ccc(Cl)cc3s2)CC1]

The title compound was prepared according to GP4-1, off-white solid. (8.0 g, 100% yield)

LC-MS (ESI): [M+1]$^+$=398.03, $t_R$=4.58 min.

$^1$H NMR (400 MHz, CDCl$_3$) δ 7.71 (s, 1H), 7.39 (d, J=0.9 Hz, 1H), 3.62-3.57 (m, 8H), 1.49 (s, 9H).

$^{13}$C NMR (101 MHz, CDCl$_3$) δ 168.70, 154.52, 151.58, 132.37, 129.34, 123.24, 120.36, 113.95, 80.51, 48.21, 28.39.

tert-butyl 4-(6-phenylbenzothiazol-2-yl)piperazine-1-carboxylate

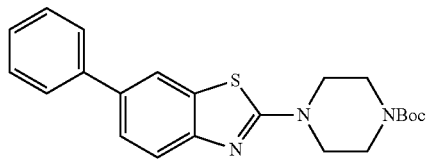 [SMILES: CC(C)(C)OC(=O)N1CCN(c2nc3ccc(-c4ccccc4)cc3s2)CC1]

tert-butyl 4-(6-bromobenzothiazol-2-yl)piperazine-1-carboxylate (1.0 g, 2.5 mmol), phenyl boronic acid (336 mg, 2.75 mmol), K$_2$CO$_3$ (691 mg, 5.0 mmol) were added into a 50 mL of flask, flushed with N$_2$, and PdCl$_2$(dppf) DCM complex (100 mg, 5 mol %) was added, followed by addition of 10 mL of DMF. The mixture was heated up to 80° C. and stirred under N$_2$ overnight. The reaction was cooled down to rt, diluted with EA, washed by water, and extracted by EA. After dryness of the organic layer, the residue was applied to silica gel chromatography (PE/EA=20/1 to 10/1) to get white solid. (320 mg, 32% yield)

$^1$H NMR (400 MHz, CDCl$_3$) δ 7.83 (d, J=1.6 Hz, 1H), 7.62-7.59 (m, 3H), 7.55 (dd, J=8.4, 1.7 Hz, 1H), 7.42 (t, J=7.6 Hz, 2H), 7.31 (t, J=7.3 Hz, 1H), 3.73-3.45 (m, 8H), 1.49 (s, 9H).

$^{13}$C NMR (101 MHz, CDCl$_3$) δ 168.80, 154.57, 152.02, 141.00, 135.12, 131.51, 128.79, 127.02, 126.89, 125.54, 119.35, 119.20, 80.43, 48.29, 28.41.

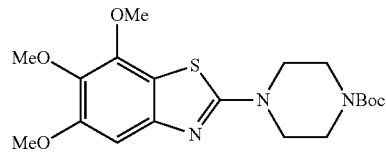 [SMILES: COc1cc2nc(N3CCN(C(=O)OC(C)(C)C)CC3)sc2c(OC)c1OC]

The title compound was prepared according to GP4-1, colorless oil. (589 mg, 99% yield)

$^1$H NMR (400 MHz, CDCl$_3$) δ 6.93 (s, 1H), 4.02 (s, 3H), 3.88 (s, 3H), 3.87 (s, 3H), 3.58 (s, 8H), 1.49 (s, 9H).

$^{13}$C NMR (101 MHz, CDCl$_3$) δ 169.17, 154.54, 153.45, 148.70, 146.68, 136.84, 114.49, 98.35, 80.40, 61.46, 60.44, 56.19, 48.19, 28.38.

tert-butyl 4-(7-fluorobenzothiazol-2-yl)piperazine-1-carboxylate

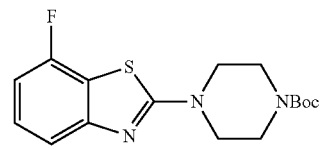

The title compound was prepared according to GP4-1. (535 mg, 73% yield)

LC-MS (ESI): [M+1]$^+$=338.19, $t_R$=4.38 min.

$^1$H NMR (400 MHz, CDCl$_3$) δ 7.34 (d, J=8.1 Hz, 1H), 7.29-7.22 (m, 1H), 3.61 (d, J=7.5 Hz, 8H), 1.49 (s, 9H).

$^{13}$C NMR (101 MHz, CDCl$_3$) δ 169.13, 156.81 (d, J=247.0 Hz), 155.43 (d, J=3.1 Hz), 154.51, 126.95 (d, J=7.8 Hz), 117.05 (d, J=16.1 Hz), 115.02 (d, J=3.1 Hz), 107.63 (d, J=18.8 Hz), 80.51, 48.32, 28.39.

tert-butyl 4-(thiazolo[5,4-b]pyridin-2-yl)piperazine-1-carboxylate

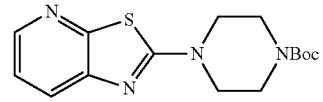 [SMILES: CC(C)(C)OC(=O)N1CCN(c2nc3cccnc3s2)CC1]

The title compound was prepared according to GP4-1, as white solid. (930 mg, 99% yield)

LC-MS (ESI): [M+1]$^+$=321.08, $t_R$=3.89 min.

$^1$H NMR (400 MHz, CDCl$_3$) δ 8.20 (dd, J=4.7, 1.1 Hz, 1H), 7.72 (dd, J=8.1, 1.2 Hz, 1H), 7.23 (dd, J=8.1, 4.8 Hz, 1H), 3.69-3.55 (m, 8H), 1.49 (s, 9H).

$^{13}$C NMR (101 MHz, CDCl$_3$) δ 167.46, 155.32, 154.49, 146.75, 142.57, 124.98, 121.36, 80.53, 47.83, 28.38.

tert-butyl 4-(5-fluorobenzothiazol-2-yl)piperazine-1-carboxylate

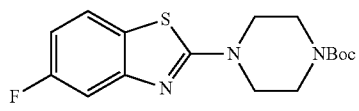 [SMILES: CC(C)(C)OC(=O)N1CCN(c2nc3cc(F)ccc3s2)CC1]

The title compound was prepared according to GP4-1, as white solid. (638 mg, 89% yield)

LC-MS (ESI): [M+1]$^+$=321.08, $t_R$=3.89 min.

$^1$H NMR (400 MHz, CDCl$_3$) δ 7.50 (dd, J=8.6, 5.3 Hz, 1H), 7.25 (dd, J=10.1, 2.5 Hz, 1H), 6.84 (td, J=8.8, 2.5 Hz, 1H), 3.64-3.55 (m, 8H), 1.49 (s, 9H).

$^{13}$C NMR (101 MHz, CDCl$_3$) δ 170.3, 162.15 (d, J=241.3 Hz), 154.53, 153.76 (d, J=12.5 Hz), 125.82 (d, J=2.2 Hz), 121.17 (d, J=10.1 Hz), 109.37 (d, J=24.5 Hz), 106.08 (d, J=24.4 Hz), 80.50, 48.16, 28.39.

tert-butyl 4-(7-(trifluoromethyl)benzothiazol-2-yl)piperazine-1-carboxylate

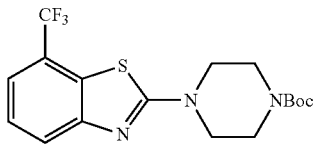 [SMILES: CC(C)(C)OC(=O)N1CCN(c2nc3cccc(C(F)(F)F)c3s2)CC1]

The title compound was prepared according to GP4-1, as white solid. (650 mg, 91% yield)

LC-MS (ESI): [M+1]$^+$=388.16, $t_R$=4.69 min.

$^1$H NMR (400 MHz, CDCl$_3$) δ 7.69 (d, J=7.4 Hz, 1H), 7.42-7.34 (m, 2H), 3.70-3.55 (m, 8H), 1.49 (s, 9H).

$^{13}$C NMR (101 MHz, CDCl$_3$) δ 169.35, 154.51, 154.05, 127.41, 126.06, 124.30 (q, J=280.9 Hz), 123.81 (q, J=33.7 Hz), 122.30, 118.83 (q, J=3.2 Hz), 80.54, 48.22, 28.38.

N$^1$-(7-fluorobenzothiazol-2-yl)ethane-1,2-diamine

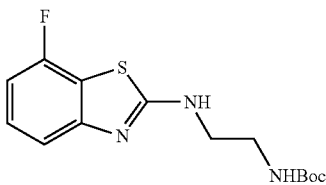 [SMILES: CC(C)(C)OC(=O)NCCNc1nc2cccc(F)c2s1]

The title compound was prepared similar to GP4-1 using 2-chloro-7-fluorobenzothiazole (500 mg, 2.7 mmol), N-Boc ethyldiamine (449 mg, 2.8 mmol) and Na$_2$CO$_3$ (339 mg, 3.2 mmol), and the crude was triturated in 10% ether in PE to get the product as off-white solid. (675 mg, 81% yield)

LC-MS (ESI): [M+1]$^+$=312.13, $t_R$=3.97 min.

$^1$H NMR (400 MHz, CDCl$_3$) δ 7.29 (d, J=8.0 Hz, 1H), 7.21 (dt, J=13.8, 6.9 Hz, 1H), 6.80 (t, J=8.6 Hz, 1H), 5.14 (brs, 1H), 3.62-3.40 (m, 4H), 1.42 (s, 9H).

$^{13}$C NMR (101 MHz, CDCl$_3$) δ 167.92, 156.89 (d, J=246.6 Hz), 156.85, 155.11 (d, J=1.5 Hz), 126.79 (d, J=7.8 Hz), 116.64 (d, J=17.0 Hz), 114.50 (d, J=3.0 Hz), 107.68 (d, J=18.9 Hz), 79.97, 46.23, 40.20, 28.35.

tert-butyl 4-(5-nitrobenzothiazol-2-yl)piperazine-1-carboxylate

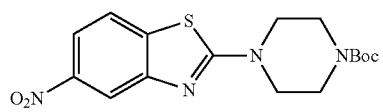 [SMILES: CC(C)(C)OC(=O)N1CCN(c2nc3cc([N+](=O)[O-])ccc3s2)CC1]

The title compound was prepared similar to GP4-1, as light yellow solid. (735 mg, 87% yield)

LC-MS (ESI): [M+1]$^+$=365.18, $t_R$=4.34 min.

$^1$H NMR (400 MHz, CDCl$_3$) δ 8.35 (d, J=2.0 Hz, 1H), 7.97 (dd, J=8.6, 2.0 Hz, 1H), 7.69 (d, J=8.6 Hz, 1H), 3.70-3.59 (m, 8H), 1.50 (s, 9H).

$^{13}$C NMR (101 MHz, CDCl$_3$) δ 169.96, 154.46, 153.04, 147.04, 137.91, 120.72, 116.35, 114.03, 80.65, 48.33, 28.38.

tert-butyl 4-(4-fluorobenzothiazol-2-yl)piperazine-1-carboxylate

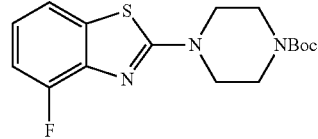 [SMILES: CC(C)(C)OC(=O)N1CCN(c2nc3c(F)cccc3s2)CC1]

The title compound was prepared similar to GP4-1, as colorless solid. (787 mg, 87% yield)

LC-MS (ESI): [M+1]$^+$=338.21, $t_R$=4.34 min.

$^1$H NMR (400 MHz, CDCl$_3$) δ 7.38-7.34 (m, 1H), 7.08-6.98 (m, 2H), 3.69-3.54 (m, 8H), 1.49 (s, 9H).

$^{13}$C NMR (101 MHz, CDCl$_3$) δ 168.57, 154.53, 153.43 (d, J=250.6 Hz), 140.98 (d, J=13.1 Hz), 133.23 (d, J=4.7 Hz), 121.94 (d, J=6.9 Hz), 116.42 (d, J=3.8 Hz), 112.21 (d, J=18.5 Hz), 80.46, 48.26, 28.38.

methyl 2-(4-(tert-butoxycarbonyl)piperazin-1-yl)benzothiazole-6-carboxylate

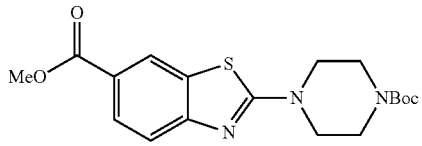 [SMILES: COC(=O)c1ccc2nc(N3CCN(C(=O)OC(C)(C)C)CC3)sc2c1]

To a mixture of tert-butyl 4-(6-bromobenzothiazol-2-yl)piperazine-1-carboxylate (1.0 g, 2.5 mmol), PdCl$_2$ (dppf)·DCM complex (204 mg, 10 mol %) and MeOH (10 mL) were added, followed by addition of Et$_3$N (1 ml, 7.5 mmol). The mixture was evacuated and backfilled with carbon monoxide three times. The reaction vessel was then pressurized at 15 psi of CO and heated at 65° C. for 48 h. After that, the crude was purified by flash column (PE/EA=20/1 to 5/1) to obtain the product as white foam. (700 mg, 74% yield)

LC-MS (ESI): [M+1]$^+$=378.16, $t_R$=4.24 min.

$^1$H NMR (400 MHz, CDCl$_3$) δ 8.32 (s, 1H), 8.00 (d, J=8.4 Hz, 1H), 7.53 (d, J=8.5 Hz, 1H), 3.91 (s, 3H), 3.71-3.57 (m, 8H), 1.49 (s, 9H).

$^{13}$C NMR (101 MHz, CDCl$_3$) δ 170.73, 166.91, 156.41, 154.49, 130.60, 128.02, 123.24, 122.82, 118.50, 80.57, 52.06, 48.23, 28.38.

tert-butyl 4-(7-bromobenzothiazol-2-yl)piperazine-1-carboxylate

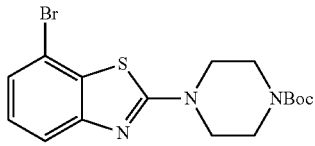

The title compound was prepared similar to GP4-1, as white solid. (5.0 g, 97% yield)

LC-MS (ESI): [M+1]$^+$=398.26, $t_R$=4.60 min.

$^1$H NMR (400 MHz, CDCl$_3$) δ 7.46 (dd, J=7.4, 1.3 Hz, 1H), 7.21-7.14 (m, 2H), 3.64-3.55 (m, 8H), 1.49 (s, 9H).

$^{13}$C NMR (101 MHz, CDCl$_3$) δ 167.73, 154.50, 152.65, 133.41, 127.29, 124.31, 117.82, 113.09, 80.49, 48.12, 28.39.

methyl 2-(4-(tert-butoxycarbonyl)piperazin-1-yl)benzothiazole-7-carboxylate

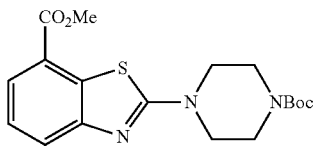 [SMILES: COC(=O)c1cccc2nc(N3CCN(C(=O)OC(C)(C)C)CC3)sc12]

To a mixture of tert-butyl 4-(7-bromobenzothiazol-2-yl)piperazine-1-carboxylate (2.0 g, 5.0 mmol), PdCl$_2$(dppf)·DCM complex (408 mg, 10 mol %) and MeOH (20 mL) were added, followed by addition of Et$_3$N (2 ml, 15.0 mmol). The mixture was evacuated and backfilled with carbon monoxide three times. The reaction vessel was then pressurized at 15 psi of CO and heated at 65° C. for 48 h. After that, the crude was purified by flash column (PE/EA=20/1 to 5/1) to obtain the product as white foam. (965 mg, 51% yield)

LC-MS (ESI): [M+1]$^+$=378.30, $t_R$=4.27 min.

$^1$H NMR (400 MHz, CDCl$_3$) δ 7.78 (d, J=7.7 Hz, 1H), 7.71 (d, J=7.2 Hz, 1H), 7.37 (t J=7.5 Hz, 1H), 3.97 (s, 3H), 3.72-3.56 (m, 8H), 1.49 (s, 9H).

$^{13}$C NMR (101 MHz, CDCl$_3$) δ 170.86, 166.63, 154.52, 153.78, 132.22, 125.79, 123.35, 123.17, 122.91, 80.37, 52.42, 47.97, 28.38.

Scheme for Synthesis of tert-butyl 4-(7-hydroxybenzothiazol-2-yl)piperazine-1-carboxylate

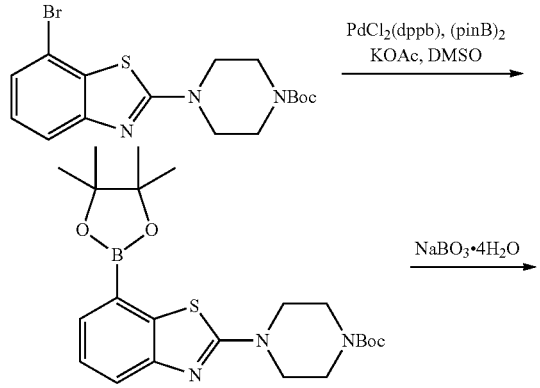

tert-butyl 4-(7-(4,4,5,5-tetramethyl-1,3,2-dioxaborolan-2-yl)benzothiazol-2-yl)piperazine-1-carboxylate

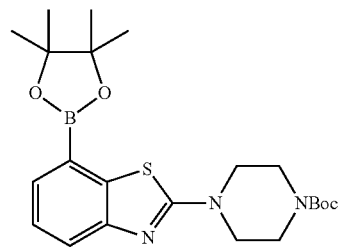 [SMILES: CC(C)(C)OC(=O)N1CCN(c2nc3cccc(B4OC(C)(C)C(C)(C)O4)c3s2)CC1]

A 100 mL of flask were charged with tert-butyl 4-(7-bromobenzothiazol-2-yl)piperazine-1-carboxylate (2.9 g, 7.28 mmol), (pinB)$_2$ (2.0 g, 8.00 mmol), KOAc (2.1 g, 21.84 mmol) and PdCl$_2$(dppb) (220 mg, 5 mol %), flushed with N$_2$. Then DMSO was added and the mixture was heated to 90° C. Aqueous workup and column chromatography purification gave the product as white solid.

LC-MS (ESI): [M+1]$^+$=446.22, $t_R$=4.75 min.

$^1$H NMR (400 MHz, CDCl$_3$) δ 7.67 (dd, J=7.9, 0.6 Hz, 1H), 7.54 (d, J=6.7 Hz, 1H), 7.31 (t, J=7.6 Hz, 1H), 3.69-3.55 (m, 8H), 1.38 (s, 12H), 1.26 (s, 9H).

$^{13}$C NMR (101 MHz, CDCl$_3$) δ 170.01, 154.63, 152.14, 137.20, 128.63, 125.51, 122.00, 84.37, 80.37, 48.06, 28.39, 24.93.

tert-butyl 4-(7-hydroxybenzothiazol-2-yl)piperazine-1-carboxylate {Hussain, 2010 #830}

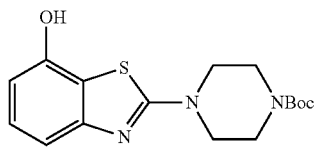 [SMILES: CC(C)(C)OC(=O)N1CCN(c2nc3cccc(O)c3s2)CC1]

A round bottom flask was charged with boronic ester synthesized above (1.58g, 3.6 mmol) and SPB (1.64 g, 10.7 mmol). THF/H$_2$O (1/1, 20 mL) was added. The reaction was stirred at rt for 2 hours. The solid was filtered off, added by water (50 mL), extracted by EA and concentrated to get the crude, which was applied to column purification (PE/EA=5/1 as eluent) to obtain the product as white foam. (754 mg, 63% yield)

LC-MS (ESI): [M+1]$^+$=336.15, $t_R$=3.73 min.

$^1$H NMR (400 MHz, CDCl$_3$) δ 7.08 (d, J=7.9 Hz, 1H), 7.03 (t, J=7.9 Hz, 1H), 6.50 (d, J=7.6 Hz, 1H), 3.57-3.45 (m, 8H), 1.41 (s, 9H).

$^{13}$C NMR (101 MHz, CDCl$_3$) δ 169.64, 154.74, 153.85, 150.91, 127.09, 117.11, 111.33, 107.77, 80.77, 48.13, 28.41.

Scheme for Synthesis of tert-butyl 4-(benzothiazol-2-ylmethyl)piperazine-1-carboxylate

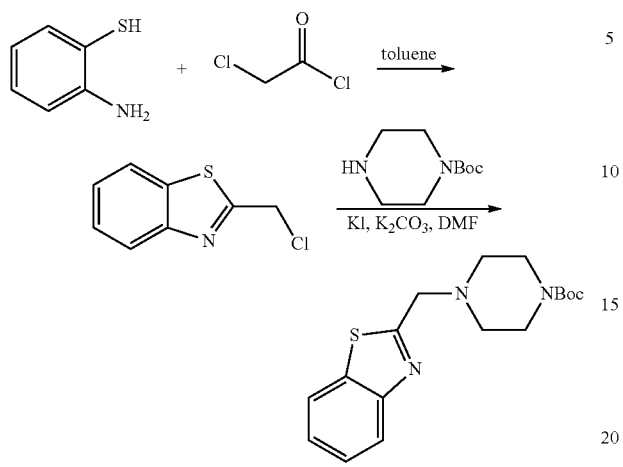

2-(chloromethyl)benzothiazole (Acsadi, Moore et al. 2012)

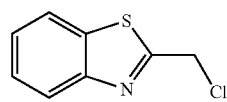 [SMILES: ClCc1nc2ccccc2s1]

A solution of 2-aminothiophenol (2.0 g, 16.0 mmol) in toluene (20 mL) and 2-chloroacetyl chloride was added dropwise with continuous stirring over 15 min. The mixture was allowed to continue stirring at rt. The mixture was portioned between water and EA. The crude was purified by silica gel (PE/EA=20/1) to give the product as colorless oil. (1.9 g, 65% yield)

$^1$H NMR (400 MHz, CDCl$_3$) δ 7.94-7.88 (m, 1H), 7.79-7.73 (m, 1H), 7.41-7.35 (m, 1H), 7.32-7.27 (m, 1H), 4.82 (s, 2H).

$^{13}$C NMR (101 MHz, CDCl$_3$) δ 166.76, 152.82, 135.83, 126.45, 125.74, 123.46, 121.77, 42.08.

tert-butyl 4-(benzothiazol-2-ylmethyl)piperazine-1-carboxylate

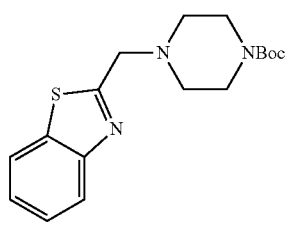 [SMILES: CC(C)(C)OC(=O)N1CCN(Cc2nc3ccccc3s2)CC1]

2-(chloromethyl)benzothiazole (500 mg, 2.7 mmol), N-Boc piperazine (540 mg, 2.9 mmol), K$_2$CO$_3$ (450 mg, 3.2 mmol) and KI (45 mg, 10 mol %) were added to a 25 mL of flask with 10 mL of DMF, which was heated to 90° C. overnight. Water was added, extracted by EA (2×25 mL) and concentrated to give the product as yellow oil. (900 mg, 100% yield)

LC-MS (ESI): [M+1]$^+$=334.42, t$_R$=6.00 min.

$^1$H NMR (400 MHz, CDCl$_3$) δ 7.97 (d, J=8.0 Hz, 1H), 7.87 (d, J=7.6 Hz, 1H), 7.49-7.43 (m, 1H), 7.41-7.34 (m, 1H), 3.97 (s, 2H), 3.50 (t, J=5.0 Hz, 41-1), 2.60 (t, J=5.0 Hz, 4H), 1.46 (s, 9H).

$^{13}$C NMR (101 MHz, CDCl$_3$) δ 171.44, 154.73, 153.25, 135.36, 125.91, 124.99, 122.86, 121.71, 79.79, 60.22, 53.17, 28.42.

tert-butyl 4-(4,6-difluorobenzothiazol-2-yl)piperazine-1-carboxylate

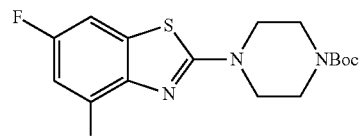

The title compound was prepared similar to GP4-1, as greenish solid. (870 mg, 100% yield)

LC-MS (ESI): [M+1]$^+$=356.44, t$_R$=4.40 min.

$^1$H NMR (400 MHz, CDCl$_3$) δ 7.16-7.11 (m, 1H), 6.89-6.81 (m, 1H), 3.64-3.55 (m, 8H), 1.49 (s, 9H).

$^{13}$C NMR (101 MHz, CDCl$_3$) δ 167.97, 157.52 (dd, J=242.6, 10.5 Hz), 154.51, 152.57 (dd, J=253.8, 12.9 Hz), 137.55 (dd, J=12.9, 2.7 Hz), 133.08 (dd, J=12.3, 6.2 Hz), 103.29 (dd, J=26.7, 4.3 Hz), 101.78 (dd, J=27.5, 22.4 Hz), 80.52, 48.26, 28.38.

Scheme for Synthesis of 2-(piperidin-4-yl)benzothiazole (Akasaka-Manya, Manya et al. 2004)

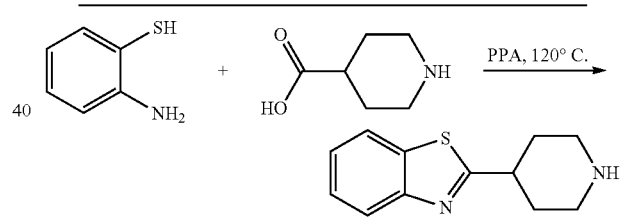

2-(piperidin-4-yl)benzothiazole

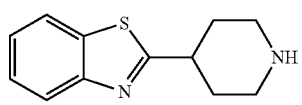 [SMILES: c1ccc2sc(C3CCNCC3)nc2c1]

To a three-necked flask was added 2-aminothiophenol (5.0 g, 40 mmol), isonipecotic acid (5.2 g, 40 mmol) and PPA (25 mL). The mixture was heated up at 120° C. for 3 h. After cooling down to rt, the dense stuff was scooped into saturated cold Na$_2$CO$_3$ solution and the resulting solid was filtered, washed with was water and dried over high vacuum to obtain off-white solid (5.8 g, 66% yield).

LC-MS (ESI): [M+1]$^+$=219.2, t$_R$=0.39 min.

$^1$H NMR (400 MHz, CH$_3$OD+D$_2$O) δ 7.93-7.89 (m, 1H), 7.52-7.49 (m, 1H), 7.43-7.39 (m, 1H), 3.30-7.27 (m, 3H), 2.88 (t, J=12.5 Hz, 2H), 2.19-2.16 (m, 2H), 1.95-1.80 (m, 2H).

$^{13}$C NMR (101 MHz, CH$_3$OH+D$_2$O) δ 178.37, 153.28, 135.24, 127.88, 126.74, 123.35, 122.95, 45.71, 41.15, 32.19.

2-(piperazin-1-yl)benzothiazole

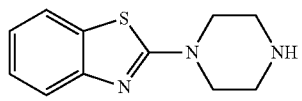 [SMILES: c1ccc2oc(N3CCNCC3)nc2c1]

The title compound was prepared according to GP4-2 as light yellow solid. (7.6 g, 97% yield)

LC-MS (ESI): [M+1]$^+$=219.9, $t_R$=3.07 min.

$^1$NMR (400 MHz, d6-DMSO) δ 7.75 (d, J=7.7 Hz, 1H), 7.45 (d, J=7.9 Hz, 1H), 7.29-7.25 (m, 1H), 7.08-7.04 (m, 1H), 2.83 (s, 4H).

$^{13}$C NMR (101 MHz, DMSO) δ 168.39, 152.48, 130.14, 125.88, 121.05, 121.02, 118.45, 49.43, 44.89.

2-(piperazin-1-yl)benzoxazole

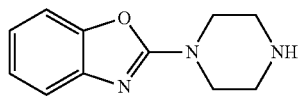

The title compound was prepared according to GP4-2 as light yellow solid using tert-butyl 4-(benzoxazol-2-yl)piperazine-1-carboxylate (9.9 g, 32.6 mmol), 50 mL of DCM and 25 mL of TFA. (4.7 g, 72% yield)

LC-MS (ESI): [M+1]$^+$=204.1, $t_R$=0.44 min.

$^1$H NMR (400 MHz, CDCl$_3$) δ 7.36 (d, J=7.7 Hz, 1H), 7.25 (d, J=7.9 Hz, 1H), 7.16 (t, J=7.6 Hz, 1H), 7.02 (t, J=7.7 Hz, 1H), 3.68 (t, J=3.6 Hz, 4H), 2.99 (t, J=3.8 Hz, 4H), 1.98 (s, 1H).

$^{13}$C NMR (101 MHz, CDCl$_3$) δ 162.29, 148.69, 143.06, 123.98, 120.64, 116.24, 108.72, 46.53, 45.41.

2-(piperazin-1 yl)-1H-benzimidazole

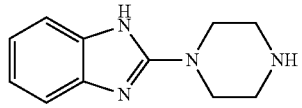

The title compound was prepared according to GP4-2 as white solid. (2.5 g, 62% yield)

6-fluoro-2-(piperazin-1-yl)benzothiazole

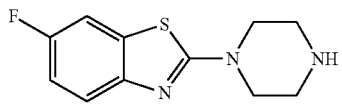

The title compound was prepared according to GP4-2 as off-white solid. (1.1 g, 87% yield)

LC-MS (ESI): [M+1]$^+$=237.8, $t_R$=2.85 min.

$^1$H NMR (400 MHz, CDCl$_3$) δ 7.46 (s, 1H), 7.31 (s, 1H), 7.01 (s, 1H), 3.57 (s, 4H), 2.99 (s, 4H), 1.87 (s, 1H).

$^{13}$C NMR (101 MHz, CDCl$_3$) δ 168.64, 158.06 (d, J=239.8 Hz), 149.12, 131.28 (d, J=10.8 Hz), 119.47 (d, J=8.6 Hz), 113.59 (d, J=23.8 Hz), 107.40 (d, J=26.9 Hz), 49.45, 45.44.

6-methoxy-2-(piperazin-1-yl)benzothiazole

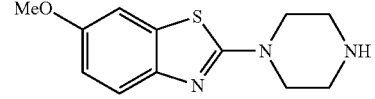 [SMILES: COc1ccc2nc(N3CCNCC3)sc2c1]

The title compound was prepared according to GP4-2 as off-white solid. (0.95 g, 67% yield)

$^1$H NMR (400 MHz, CDCl$_3$) δ 7.46 (d, J=8.8 Hz, 1H), 7.14 (d, J=2.2 Hz, 1H), 6.90 (dd, J=8.8, 2.3 Hz, 1H), 3.81 (s, 3H), 3.56 (t, J=4.8 Hz, 4H), 3.07-2.92 (t, J=5.0 Hz, 4H), 2.14 (s, 1H).

$^{13}$C NMR (101 MHz, CDCl$_3$) δ 167.73, 155.04, 146.87, 131.59, 119.54, 113.61, 105.24, 55.88, 49.41, 45.43.

6-chloro-2-(piperazin-1-yl)benzothiazole

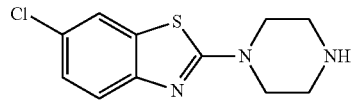 [SMILES: Clc1ccc2nc(N3CCNCC3)sc2c1]

The title compound was prepared according to GP4-2. (710 mg, 61% yield)

$^1$H NMR (400 MHz, CDCl$_3$) δ 7.55 (d, J=1.7 Hz, 1H), 7.43 (d, J=8.6 Hz, 1H), 7.23 (dd, J=8.6, 1.8 Hz, 1H), 3.60 (t, J=5.0 Hz, 4H), 2.98 (t, J=5.0 Hz, 4H), 1.85 (s, 1H).

$^{13}$C NMR (101 MHz, CDCl$_3$) δ 169.09, 151.39, 131.81, 126.42, 126.38, 120.35, 119.68, 49.48, 45.46.

6-methyl-2-(piperazin-1-yl)benzothiazole

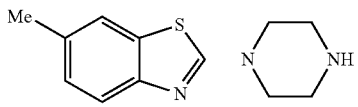

The title compound was prepared according to GP4-2. (1.67 g, 98% yield)

$^1$H NMR (400 MHz, CDCl$_3$) δ 7.44 (d, J=8.1 Hz, 1H), 7.38 (s, 1H), 7.09 (d, J=7.9 Hz, 1H), 3.56 (s, 4H), 2.96 (s, 4H), 2.37 (s, 3H), 1.87 (s, 1H).

$^{13}$C NMR (101 MHz, CDCl$_3$) δ 168.54, 150.53, 131.08, 130.66, 127.14, 120.75, 118.71, 49.47, 45.47, 21.22.

6-phenyl-2-(piperazin-1-yl)benzothiazole

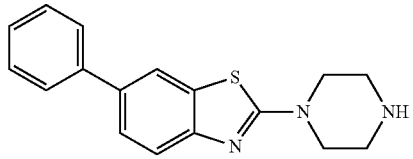 [SMILES: c1ccc(-c2ccc3nc(N4CCNCC4)sc3c2)cc1]

The title compound was prepared according to GP4-2. (230 mg, 96% yield)

$^1$H NMR (400 MHz, CDCl$_3$) δ 7.81 (s, 1H), 7.59 (d, J=4.5 Hz, 3H), 7.53 (d, J=8.0 Hz, 1H), 7.41 (t, J=7.2 Hz, 2H), 7.30 (t, J=7.0 Hz, 1H), 3.60 (s, 4H), 2.97 (s, 4H), 1.80 (s, 1H).

$^{13}$C NMR (101 MHz, CDCl$_3$) δ 169.22, 152.22, 141.08, 134.77, 131.42, 128.78, 126.99, 126.82, 125.41, 119.15, 119.13, 49.57, 45.53.

5,6,7-trimethoxy-2-(piperazin-1-yl)benzothiazole

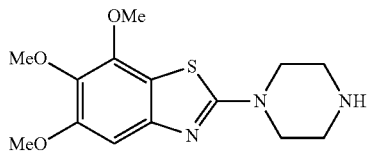 [SMILES: COc1cc2nc(N3CCNCC3)sc2c(OC)c1OC]

The title compound was prepared according to GP4-2. (252 mg, 57% yield)

LC-MS (ESI): [M+1]$^+$=309.95, t$_R$=2.87 min.

$^1$H NMR (400 MHz, CDCl$_3$) δ 6.92 (s, 1H), 4.02 (s, 3H), 3.88 (s, 3H), 3.87 (s, 3H), 3.57 (t, J=5.0 Hz, 4H), 3.02-2.97 (t, J=5.0 Hz, 4H), 1.81 (s, 1H).

$^{13}$C NMR (101 MHz, CDCl$_3$) δ 169.60, 153.32, 148.86, 146.66, 136.62, 114.29, 98.22, 61.45, 60.40, 56.17, 49.45, 45.45.

7-fluoro-2-(piperazin-1-yl)benzothiazole

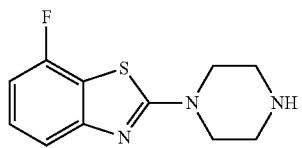 [SMILES: Fc1cccc2nc(N3CCNCC3)sc12]

The title compound was prepared according to GP4-2, as light brown solid. (344 mg, 67% yield)

LC-MS (ESI): [M+1]$^+$=238.08, t$_R$=2.94 min.

$^1$H NMR (400 MHz, CDCl$_3$) δ 7.33 (d, J=8.0 Hz, 1H), 7.24 (td, J=8.1, 5.8 Hz, 1H), 6.80 (t, J=8.7 Hz, 1H), 3.62 (t, J=5.2 Hz, 4H), 3.01 (t, J=5.2 Hz, 4H), 1.91 (s, 1H).

$^{13}$C NMR (101 MHz, CDCl$_3$) δ 169.52, 156.85 (d, J=244.4 Hz), 155.61, 126.82 (d, J=7.9 Hz), 116.90 (d, J=16.1 Hz), 114.82 (d, J=3.1 Hz), 107.36 (d, J=18.9 Hz), 49.59, 45.47.

2-(piperazin-1-yl)thiazolo[5,4-b]pyridine

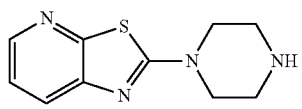 [SMILES: c1cnc2sc(N3CCNCC3)nc2c1]

The title compound was prepared according to GP4-2, as white solid. (530 mg, 83% yield)

LC-MS (ESI): [M+1]$^+$=220.97, t$_R$=0.43 min.

$^1$H NMR (400 MHz, CDCl$_3$) δ 8.19 (d, J=4.7 Hz, 1H), 7.71 (d, J=8.0 Hz, 1H), 7.22 (dd, J=7.9, 4.9 Hz, 1H), 3.69 (t, J=5.0 Hz, 4H), 3.17 (brs, 1H), 3.04 (t, J=5.0 Hz, 4H).

$^{13}$C NMR (101 MHz, CDCl$_3$) δ 167.65, 155.35, 146.85, 142.40, 124.78, 121.29, 48.73, 45.23.

5-fluoro-2-(piperazin-1-yl)benzothiazole

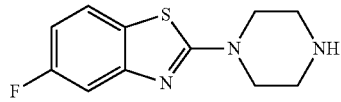

The title compound was prepared according to GP4-2, as off-white solid. (376 mg, 84% yield)

LC-MS (ESI): [M+1]$^+$=237.91, t$_R$=2.92 min.

$^1$H NMR (400 MHz, CDCl$_3$) δ 7.52-7.44 (m, 1H), 7.23 (d, J=10.2 Hz, 1H), 6.85-6.77 (m, 1H), 3.63-3.56 (t, J=4.8 Hz, 4H), 3.02-2.95 (t, J=4.8 Hz, 4H), 1.81 (s, 1H).

$^{13}$C NMR (101 MHz, CDCl$_3$) δ 170.71, 162.12 (d, J=240.9 Hz), 153.95 (d, J=12.4 Hz), 125.72 (d, J=2.0 Hz), 121.06 (d, J=10.1 Hz), 108.99 (d, J=24.5 Hz), 105.85 (d, J=24.3 Hz), 49.43, 45.49.

2-(piperazin-1-yl)-7-(trifluoromethyl)benzothiazole

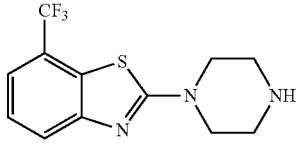 [SMILES: FC(F)(F)c1cccc2nc(N3CCNCC3)sc12]

The title compound was prepared according to GP4-2, as white solid. (440 mg, 66% yield)

LC-MS (ESI): [M+1]$^+$=287.88, t$_R$=3.29 min.

$^1$H NMR (400 MHz, CDCl$_3$) δ 7.68 (d, J=7.3 Hz, 1H), 7.40-7.30 (m, 2H), 3.64 (t, J=4.4 Hz, 4H), 3.00 (t, J=4.4 Hz, 4H), 1.85 (s, 1H).

$^{13}$C NMR (101 MHz, CDCl$_3$) δ 169.69, 154.24, 127.34, 125.92, 123.98 (q, J=273.3 Hz), 123.70 (q, J=25.4 Hz), 122.06, 118.50 (q, J=3.2 Hz), 49.50, 45.47.

N$^1$-(7-fluorobenzothiazol-2-yl)ethane-1,2-diamine

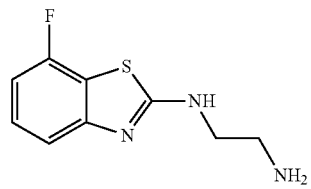 [SMILES: NCCNc1nc2cccc(F)c2s1]

The title compound was prepared according to GP4-2, as white solid. (418 mg, 91% yield)

LC-MS (ESI): [M+1]$^+$=212.15, t$_R$=0.43 min.

$^1$H NMR (400 MHz, CDCl$_3$) δ 7.30 (d, J=8.0 Hz, 1H), 7.21 (td, J=8.1, 5.7 Hz, 1H), 6.80 (t, J=8.7 Hz, 1H), 3.55-3.47 (t, J=5.6 Hz, 2H), 3.06-2.99 (t, J=5.6 Hz, 2H), 2.00 (brs, 3H).

$^{13}$C NMR (101 MHz, CDCl$_3$) δ 168.15, 156.91 (d, J=246.6 Hz), 155.32 (d, J=3.2 Hz), 126.77 (d, J=7.8 Hz), 116.65 (d, J=16.4 Hz), 114.50 (d, J=3.0 Hz), 107.57 (d, J=18.9 Hz), 47.50, 40.81.

5-nitro-2-(piperazin-1-yl)benzothiazole

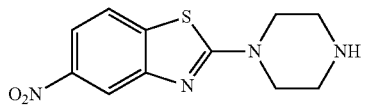 [SMILES: O=[N+]([O-])c1ccc2sc(N3CCNCC3)nc2c1]

The title compound was prepared according to GP4-2, as light yellow solid. (520 mg, 99% yield)

LC-MS (ESI): [M+1]$^+$=265.07, $t_R$=2.97 min.

$^1$H NMR (400 MHz, CDCl$_3$) δ 8.31 (s, 1H), 7.93 (d, J=8.4 Hz, 1H), 7.66 (d, J=8.5 Hz, 1H), 3.65 (s, 4H), 3.02 (s, 4H), 1.84 (s, 2H).

$^{13}$C NMR (101 MHz, CDCl$_3$) δ 170.28, 153.19, 146.91, 137.90, 120.59, 116.00, 113.67, 49.61, 45.46.

4-fluoro-2-(piperazin-1-yl)benzothiazole

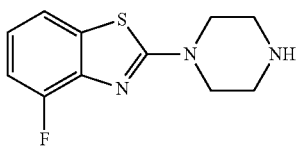 [SMILES: Fc1cccc2sc(N3CCNCC3)nc12]

The title compound was prepared according to GP4-2, as off-white solid. (484 mg, 88% yield)

LC-MS (ESI): [M+1]$^+$=238.11, $t_R$=2.89 min.

$^1$H NMR (400 MHz, CDCl$_3$) δ 7.35 (d, J=7.8 Hz, 1H), 7.07-6.95 (m, 2H), 3.63 (t, J=5.0 Hz, 4H), 2.99 (t, J=5.0 Hz, 4H), 1.98 (s, 1H).

$^{13}$C NMR (101 MHz, CDCl$_3$) δ 168.96, 153.31 (d, J=250.2 Hz), 141.09 (d, J=13.1 Hz), 133.13 (d, J=4.8 Hz), 121.60 (d, J=6.9 Hz), 116.36 (d, J=3.8 Hz), 112.09 (d, J=18.5 Hz), 49.51, 45.44.

Methyl 2-(piperazin-1-yl)benzothiazole-6-carboxylate

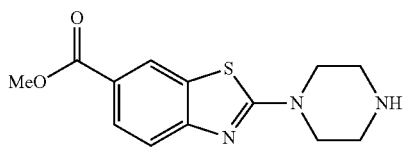 [SMILES: COC(=O)c1ccc2nc(N3CCNCC3)sc2c1]

The title compound was prepared according to GP4-2, as off-white solid. (494 mg, 96% yield)

LC-MS (ESI): [M+1]$^+$=277.98, $t_R$=4.50 min.

$^1$H NMR (400 MHz, CDCl$_3$) δ 8.31 (s, 1H), 7.99 (d, J=8.4 Hz, 1H), 7.52 (d, J=8.5 Hz, 1H), 3.91 (s, 3H), 3.66 (t, J=5.0 Hz, 4H), 3.01 (t, J=5.0 Hz, 4H), 1.74 (s, 1H).

$^{13}$C NMR (101 MHz, CDCl$_3$) δ 171.09, 167.01, 156.63, 130.49, 127.97, 122.92, 122.75, 118.27, 52.03, 49.56, 45.53.

Methyl 2-(piperazin-1-yl)benzothiazole-7-carboxylate

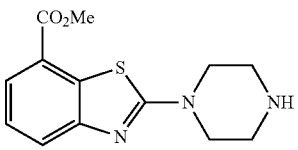 [SMILES: COC(=O)c1cccc2nc(N3CCNCC3)sc12]

The title compound was prepared according to GP4-2, as off-white solid. (494 mg, 96% yield)

LC-MS (ESI): [M+1]$^+$=278.19, $t_R$=4.50 min.

$^1$H NMR (400 MHz, CDCl$_3$) δ 7.69 (dd, J=7.7, 0.6 Hz, 1H), 7.63 (d, J=8.0 Hz, 1H), 7.28 (t, J=7.8 Hz, 1H), 3.90 (s, 3H), 3.60 (t, J=5.0 Hz, 4H), 3.26-2.79 (t, J=5.0 Hz, 4H), 1.81 (s, 1H).

$^{13}$C NMR (101 MHz, CDCl$_3$) δ 171.22, 166.74, 153.96, 132.16, 125.70, 123.14, 123.10, 122.66, 52.40, 49.29, 45.52.

7-hydroxyl-2-(piperazin-1-yl)benzothiazole

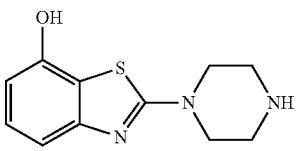 [SMILES: Oc1cccc2nc(N3CCNCC3)sc12]

The title compound was prepared according to GP4-2 using tert-butyl 4-(7-hydroxybenzothiazol-2-yl)piperazine-1-carboxylate (370 mg, 1.10 mmol), and the mixture was concentrated to dryness, which was triturated by ether to get white solid. The solid was suspended in 10% MeOH in DCM and neutralized by saturated Na$_2$CO$_3$ solution. Rotavapor treatment of the organic layer gave the desired product. (107 mg, 41% yield)

LC-MS (ESI): [M+1]$^+$=236.46, $t_R$=0.36 min.

$^1$H NMR (400 MHz, MeOD) δ 7.11 (t, J=8.0 Hz, 1H), 7.01 (d, J=8.0 Hz, 1H), 6.54 (d, J=7.9 Hz, 1H), 3.59 (t, J=5.0 Hz, 4H), 2.96 (t, J=5.0 Hz, 4H).

$^{13}$C NMR (101 MHz, MeOD) δ 171.43, 155.13, 152.92, 128.00, 117.77, 111.41, 108.31, 49.96, 45.81.

2-(piperazin-1-ylmethyl)benzothiazole

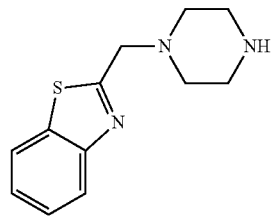 [SMILES: c1ccc2sc(CN3CCNCC3)nc2c1]

The title compound was prepared according to GP4-2 as yellow oil. (490 mg, 78% yield)

LC-MS (ESI): [M+1]$^+$=234.30, $t_R$=0.38 min.

$^1$H NMR (400 MHz, CDCl$_3$) δ 7.97 (d, J=8.0 Hz, 1H), 7.86 (dd, J=7.9, 0.5 Hz, 1H), 7.47-7.42 (m, 1H), 7.38-7.33 (m, 1H), 3.93 (s, 2H), 2.97-2.92 (m, 4H), 2.66-2.58 (m, 4H), 2.04 (brs, 1H).

$^{13}$C NMR (101 MHz, CDCl$_3$) δ 172.17, 153.30, 135.41, 125.79, 124.84, 122.78, 121.68, 60.83, 54.70, 46.02.

4,6-difluoro-2-(piperazin-1-yl)benzothiazole

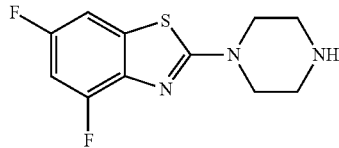 [SMILES: Fc1cc(F)c2nc(N3CCNCC3)sc2c1]

The title compound was prepared according to GP4-2 as greenish solid. (533 mg, 86% yield)

LC-MS (ESI): [M+1]$^+$=256.26, t$_R$=0.35 min.

$^1$H NMR (400 MHz, CDCl$_3$) δ 7.15-7.08 (m, 1H), 6.89-6.78 (m, 1H), 3.60 (t, J=5.2 Hz, 4H), 3.00 (t, J=5.2 Hz, 4H), 1.82 (s, 1H).

$^{13}$C NMR (101 MHz, CDCl$_3$) δ 168.36, 157.31 (dd, J=242.1, 10.4 Hz), 152.42 (dd, J=253.4, 12.8 Hz), 137.69 (dd, J=12.9, 2.5 Hz), 132.99 (dd, J=12.2, 6.2 Hz), 103.20 (dd, J=26.6, 4.3 Hz), 101.60 (dd, J=27.5, 22.5 Hz), 49.53, 45.45.

2-(4-((1-(thiophen-2-ylmethyl)-1H-tetrazol-5-yl)methyl)piperazin-1-yl)benzothiazole

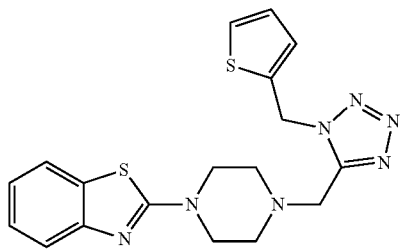 [SMILES: c1csc(Cn2nnnc2CN2CCN(c3nc4ccccc4s3)CC2)c1]

The title compound was prepared according to GP4-3 using 37% formaldehyde solution (168 μL, 2.74 mmol), 2-(piperazin-1-yl)benzothiazole (500 mg, 2.28 mmol), TMSN$_3$ (360 μL, 2.74 mmol), 2-(isocyanomethyl)thiophene (295 mg, 2.39 mmol) and DCM (5 mL) used as solvent. Silica gel chromatography (DCM/EA=20/1 to 10/1 as eluent) gave the pure product as white solid. (700 mg, 77% yield)

LC-MS (ESI): [M+1]$^+$=398.2, t$_R$=3.99 min.

$^1$H NMR (400 MHz, CDCl$_3$) δ 7.61 (d, J=7.8 Hz, 1H), 7.56 (d, J=8.1 Hz, 1H), 7.37-7.27 (m, 2H), 7.11-7.08 (m, 2H), 7.02-7.00 (m, 1H), 5.89 (s, 2H), 3.86 (s, 2H), 3.62 (t, 4H), 2.61(t, 4H).

$^{13}$C NMR (101 MHz, CDCl$_3$) δ 168.50, 152.54, 151.04, 134.94, 130.80, 128.16, 127.46, 127.04, 126.13, 121.75, 120.78, 119.32, 52.46, 50.83, 47.95, 46.11.

HPLC: 99% purity.

HRMS (ESI): calculated for C$_{18}$H$_{20}$N$_7$S$_2$ [M+1]$^+$= 398.1222; found 398.1229.

2-(4-(1-(1-(thiophen-2-ylmethyl)-1H-tetrazol-5-yl)ethyl)piperazin-1-yl)benzothiazole

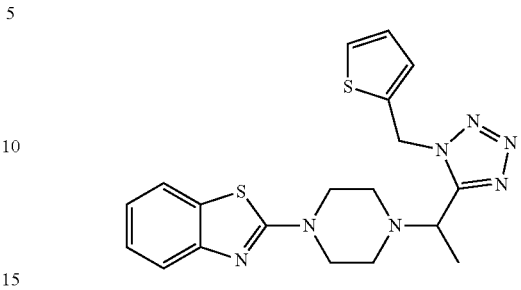

The title compound was prepared according to GP4-3 using acetaldehyde (140 μL, 2.51 mmol), 2-(piperazin-1-yl)benzothiazole (500 mg, 2.28 mmol), TMSN$_3$ (330 μL, 2.51 mmol), 2-(isocyanomethyl)thiophene (295 mg, 2.39 mmol) and DCM (5 mL) used as solvent. (174 mg, 19% yield, white solid)

LC-MS (ESI): [M+1]$^+$=412.3, t$_R$=4.09 min.

$^1$H NMR (400 MHz, CDCl$_3$) δ 7.59 (d, J=7.6 Hz, 1H), 7.55 (d, J=7.9 Hz, 1H), 7.29-7.27 (m, 3H), 7.10-6.99 (m, 3H), 5.91 (d, J=10.6 Hz, 2H), 4.13 (d, J=6.5 Hz, 1H), 3.58 (s, 4H), 2.63 (s, 4H), 1.52 (d, J=6.3 Hz, 3H).

$^{13}$C NMR (101 MHz, CDCl$_3$) δ 168.51, 154.66, 152.58, 135.32, 130.79, 127.82, 127.44, 126.79, 126.10, 121.68, 120.77, 119.26, 54.60, 48.28, 47.98, 46.24, 10.69.

HPLC: 99% purity.

HRMS (ESI): calculated for C$_{19}$H$_{22}$N$_7$S$_2$ [M+1]$^+$= 412.2566; found 412.2572.

2-(1-(1-(1-(furan-2-ylmethyl)-1H-tetrazol-5-yl)propyl)piperidin-4-yl)benzothiazole

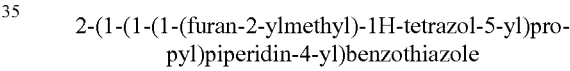

The title compound was prepared according to GP4-3 as off-white solid. (540 mg. 29% yield)

LC-MS (ESI): [M+1]$^+$=409.2, t$_R$=3.75 min.

$^1$H NMR (400 MHz, CDCl$_3$) δ 7.97 (d, J=8.1 Hz, 1H), 7.85 (d, J=7.9 Hz, 1H), 7.45 (t, J=7.6 Hz, 1H), 7.40 (s, 1H), 7.35 (t, J=7.6 Hz, 1H), 6.40 (d, J=15.8 Hz, 2H), 3.93 (dd, J=10.0, 4.2 Hz, 1H), 3.09-3.00 (m, 2H), 2.76-2.67 (m, 2H), 2.34 (t, J=10.7 Hz, 1H), 2.23 (d, J=12.5 Hz, 1H), 2.18-2.07 (m, 2H), 2.06-1.90 (m, 2H), 1.77 (qd, J=12.1, 3.6 Hz, 1H), 0.89 (t, J=7.3 Hz, 3H).

$^{13}$C NMR (101 MHz, CDCl$_3$) δ 175.32, 154.18, 153.08, 146.92, 143.41, 142.94, 134.51, 126.00, 124.79, 122.68, 121.60, 110.97, 110.15, 61.23, 50.71, 47.72, 44.20, 41.30, 32.77, 32.54, 19.84, 11.46.

HPLC: 99% purity.

HRMS (ESI): calculated for $C_{21}H_{24}N_6OSNa$ [M+Na]$^+$= 431.1808; found 431.1799.

2-(4-(1-(1-(furan-2-ylmethyl)-1H-tetrazol-5-yl)propyl)piperazin-1-yl)benzothiazole

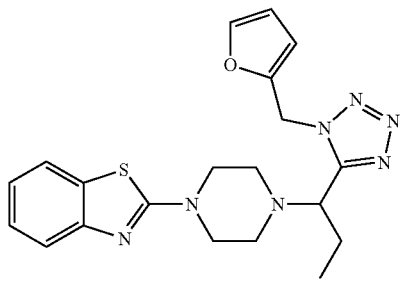

The title compound was prepared according to GP4-3 as off-white solid. (206 mg, 21% yield)

LC-MS (ESI): [M+1]$^+$=410.3, $t_R$=4.10 min.

$^1$H NMR (400 MHz, CDCl$_3$) δ 7.59 (d, J=7.8 Hz, 1H), 7.54 (d, J=8.1 Hz, 1H), 7.39 (s, 1H), 7.29 (t, J=7.2 Hz, 1H), 7.07 (t, J=7.6 Hz, 1H), 6.47-6.32 (m, 2H), 5.68 (d, J=2.7 Hz, 2H), 3.97 (dd, J=10.0, 4.4 Hz, 1H), 3.68-3.46 (m, 4H), 2.92-2.45 (m, 4H), 2.18-1.95 (m, 2H), 0.86 (t, J=7.3 Hz, 3H).

$^{13}$C NMR (101 MHz, CDCl$_3$) δ 168.54, 153.76, 152.60, 146.69, 143.43, 130.77, 126.05, 121.60, 120.74, 119.20, 111.08, 110.31, 60.88, 48.48, 48.44, 44.21, 20.14, 11.22.

HPLC: 100% purity.

HRMS (ESI): calculated for $C_{20}H_{24}N_7OS$ [M+1]$^+$= 410.1763; found 410.1746.

2-(4-(1-(1-(thiophen-2-ylmethyl)-1H-tetrazol-5-yl)propyl)piperazin-1-yl)benzothiazole

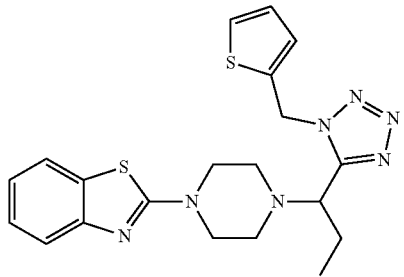 [SMILES: CCC(c1nnnn1Cc1cccs1)N1CCN(c2nc3ccccc3s2)CC1]

The title compound was prepared according to GP4-3 as off-white solid. (615 mg, 32% yield)

LC-MS (ESI): [M+1]$^+$=426.3, $t_R$=4.20 min.

$^1$H NMR (400 MHz, CDCl$_3$) δ 7.59 (d, J=7.8 Hz, 1H), 7.54 (d, J=8.0 Hz, 1H), 7.36-7.28 (m, 2H), 7.14-7.04 (m, 2H), 7.00-6.99 (m, 1H), 5.84 (d, J=4.3 Hz, 2H), 3.85 (dd, J=9.9, 3.8 Hz, 1H), 3.54 (d, J=4.0 Hz, 4H), 2.83-2.49 (m, 4H), 2.19-1.92 (m, 3H), 0.82 (t, J=7.1 Hz, 3H).

$^{13}$C NMR (101 MHz, CDCl$_3$) δ 168.54, 153.55, 152.58, 135.39, 130.76, 127.82, 127.38, 126.90, 126.06, 121.62, 120.75, 119.21, 61.18, 48.45, 48.39, 46.11, 19.87, 11.27.

HPLC: 99% purity.

HRMS (ESI): calculated for $C_{20}H_{23}N_7S_2Na$ [M+Na]$^+$= 444.1440; found 444.1442.

2-(4-(1-(1-(thiophen-2-ylmethyl)-1H-tetrazol-5-yl)propyl)piperazin-1-yl)benzoxazole

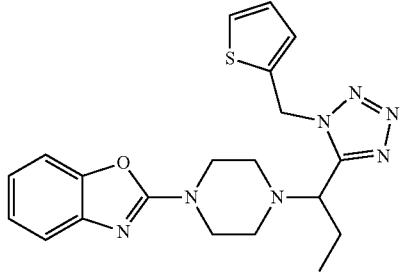 [SMILES: CCC(c1nnnn1Cc1cccs1)N1CCN(c2nc3ccccc3o2)CC1]

The title compound was prepared according to GP4-3 as white solid. (230 mg, 23% yield)

LC-MS (ESI): [M+1]$^+$=410.23, $t_R$=4.04 min.

$^1$H NMR (400 MHz, CDCl$_3$) δ 7.39-7.29 (m, 1H), 7.24 (d, J=8.0 Hz, 1H), 7.16 (t, J=7.6 Hz, 1H), 7.10-6.96 (m, 1H), 5.85 (d, J=5.1 Hz, 1H), 3.85 (dd, J=10.2, 4.3 Hz, 1H), 3.66-3.57 (m, 2H), 2.80-2.47 (m, 2H), 2.28-1.86 (m, 1H), 0.83 (t, J=7.3 Hz, 2H).

$^{13}$C NMR (101 MHz, CDCl$_3$) δ 161.91, 153.53, 148.76, 142.91, 135.37, 127.81, 127.40, 126.89, 124.06, 120.88, 116.40, 108.81, 61.29, 48.43, 46.10, 45.65, 19.82, 11.27.

HPLC: 99% purity.

HRMS (ESI): calculated for $C_{20}H_{23}N_7S$ [M+1]$^+$= 410.1763; found 410.1746.

2-(1-(1-(1-(thiophen-2-ylmethyl)-1H-tetrazol-5-yl)propyl)piperidin-4-yl)benzothiazole

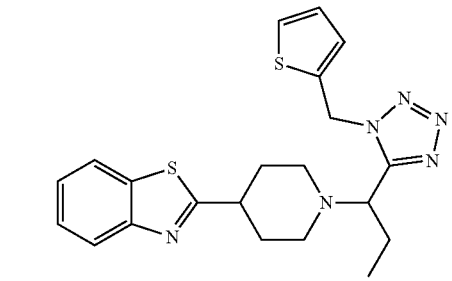

The title compound was prepared according to GP4-3, which was rinsed by ether to get white solid. (200 mg, 21% yield)

LC-MS (ESI): [M+1]$^+$=425.24, $t_R$=4.17 min.

$^1$H NMR (400 MHz, CDCl$_3$) δ 7.97 (d, J=8.1 Hz, 1H), 7.85 (d, J=7.9 Hz, 1H), 7.46 (t, J=7.6 Hz, 1H), 7.35 (t, J=7.6 Hz, 1H), 7.31 (d, J=5.0 Hz, 1H), 7.07 (s, 1H), 7.04-6.94 (m, 1H), 5.89 (s, 2H), 3.82 (dd, J=10.1, 4.1 Hz, 1H), 3.16-2.92 (m, 2H), 2.69 (dd, J=16.3, 6.9 Hz, 2H), 2.53-2.27 (m, 1H), 2.27-2.00 (m, 4H), 1.99-1.89 (m, 1H), 1.87-1.58 (m, 1H), 0.85 (t, J=7.3 Hz, 3H).

$^{13}$C NMR (101 MHz, CDCl$_3$) δ 175.29, 153.94, 153.06, 135.60, 134.51, 127.79, 127.32, 126.83, 126.01, 124.81, 122.68, 121.61, 61.54, 50.83, 47.65, 46.07, 41.27, 32.71, 32.45, 19.60, 11.50.

HPLC: 99% purity.

HRMS (ESI): calculated for $C_{21}H_{24}N_6S_2Na$ [M+Na]$^+$= 447.1402; found 447.1418.

2-(4-(1-(1-(thiophen-2-ylmethyl)-1H-tetrazol-5-yl)propyl)piperazin-1-yl)-1H-benzimidazole

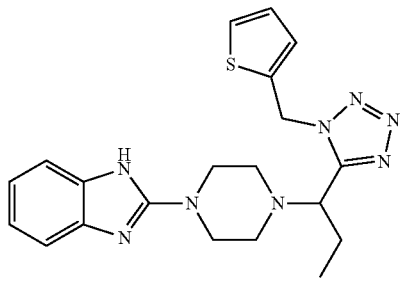 [SMILES: CCC(c1nnnn1Cc1cccs1)N1CCN(c2nc3ccccc3[nH]2)CC1]

The title compound was prepared according to GP4-3 as white solid. (73 mg, 7% yield)

LC-MS (ESI): [M+1]$^+$=409.10, $t_R$=3.48 min.

$^1$H NMR (400 MHz, MeOD) δ 7.41 (d, J=4.7 Hz, 1H), 7.24-7.22 (m, 2H), 7.18-7.17 (m, 1H), 7.01-6.99 (m, 3H), 5.96 (d, J=7.8 Hz, 2H), 4.85 (s, 2H), 4.09 (dd, J=9.0, 5.5 Hz, 1H), 3.43 (s, 4H), 2.65 (s, 4H), 2.01 (dd, J=13.2, 6.8 Hz, 2H), 0.80 (t, J=7.2 Hz, 3H).

$^{13}$C NMR (101 MHz, MeOD) δ 157.39, 155.41, 137.61, 129.21, 128.18, 128.08, 121.77, 113.24, 61.59, 49.47, 47.60, 47.10, 21.40, 11.32.

HPLC: 99% purity.

HRMS (ESI): calculated for $C_{20}H_{25}N_8S$ [M+1]$^+$= 409.1923; found 409.1909.

6-nitro-2-(4-(1-(1-(thiophen-2-ylmethyl)-1H-tetrazol-5-yl)propyl)piperazin-1-yl) benzothiazole

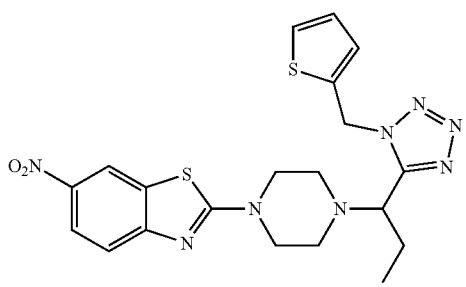 [SMILES: CCC(c1nnnn1Cc1cccs1)N1CCN(c2nc3ccc([N+](=O)[O-])cc3s2)CC1]

The title compound was prepared according to GP4-3. Product was precipitated from the reaction mixture and rinsed with ether. (2.2 g, 62% yield)

LC-MS (ESI): [M+1]$^+$=471.18, $t_R$=4.21 min.

$^1$H NMR (400 MHz, CDCl$_3$) δ 8.49 (s, 1H), 8.19 (d, J=8.9 Hz, 1H), 7.49 (d, J=9.0 Hz, 1H), 7.33 (d, J=4.8 Hz, 1H), 7.07 (s, 1H), 7.02 (t, J=3.5 Hz, 1H), 5.84 (d, J=5.4 Hz, 2H), 3.89 (dd, J=9.8, 3.9 Hz, 1H), 3.75-3.51 (m, 4H), 2.75-2.64 (m, 4H), 2.28-1.86 (m, 2H), 0.83 (t, J=7.2 Hz, 3H).

$^{13}$C NMR (101 MHz, CDCl$_3$) δ 171.55, 157.97, 153.38, 141.84, 135.30, 130.93, 127.85, 127.47, 126.96, 122.61, 118.27, 117.29, 61.03, 48.56, 48.36, 46.13, 20.10, 11.21.

HPLC: 99% purity.

HRMS (ESI): calculated for $C_{20}H_{22}N_8O_2S_2Na$ [M+1]$^+$= 493.1205; found 493.1206.

6-amino-2-(4-(1-(1-(thiophen-2-ylmethyl)-1H-tetrazol-5-yl)propyl)piperazin-1-yl) benzothiazole

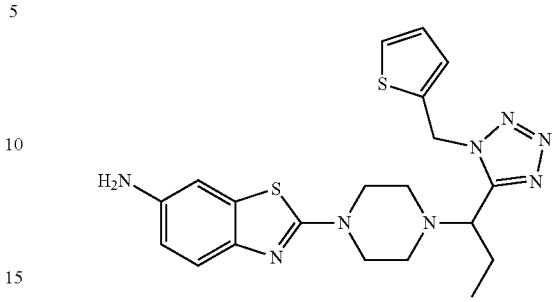

10% Pd/C wetted by MeOH (5 mL) was added by 6-nitro-2-(4-(1-(1-(thiophen-2-ylmethyl)-1H-tetrazol-5-yl)propyl)piperazin-1-yl) benzothiazole (600 mg, 1.28 mmol) and HOAc (5 mL). The flask was evacuated and flushed with hydrogen three times. The mixture was stirred at 40° C. for 7 hours. After completion, Pd/C was filtered and the filtrate was diluted with DCM and neutralized by saturated Na$_2$CO$_3$. The organic layer was collected, concentrated and purified by flash column to obtain light brown foam. (450 mg, 80% yield)

LC-MS (ESI): [M+1]$^+$=441.22, $t_R$=3.34 min.

$^1$H NMR (400 MHz, CDCl$_3$) δ 7.35 (d, J=8.0 Hz, 1H), 7.29 (d, J=13.2 Hz, 1H), 7.06 (s, 1H), 6.99 (s, 1H), 6.93 (s, 1H), 6.68 (d, J=8.0 Hz, 1H), 3.84 (d, J=9.4 Hz, 1H), 3.63 (s, 2H), 3.47 (s, 4H), 2.64 (d, J=17.5 Hz, 4H), 2.02 (d, J=26.0 Hz, 3H), 0.81 (t, J=7.2 Hz, 3H).

$^{13}$C NMR (101 MHz, CDCl$_3$) δ 166.36, 153.58, 145.45, 141.55, 135.35, 132.05, 127.87, 127.39, 126.94, 119.69, 114.80, 106.73, 61.20, 48.44, 48.39, 46.11, 19.73, 11.32.

HPLC: 99% purity.

HRMS (ESI): calculated for $C_{20}H_{25}N_8S_2$ [M+1]$^+$= 441.1644; found 441.1642.

5-((3aS,4S,6aR)-2-oxohexahydro-1H-thieno[3,4-d]imidazol-4-yl)-N-(2-(4-(1-(1-(thiophen-2-ylmethyl)-1H-tetrazol-5-yl)propyl)piperazin-1-yl)benzothiazol-6-yl)pentanamide

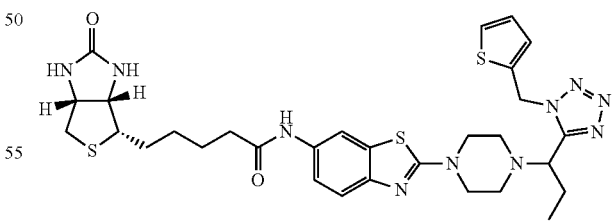

Biotin (213 mg, 0.87 mmol) was added to an anhydrous DMF (5 mL) solution of 6-amino-2-(4-(1-(1-(thiophen-2-ylmethyl)-1H-tetrazol-5-yl)propyl)piperazin-1-yl) benzothiazole (350 mg, 0.79 mmol), followed by addition of HATU (332 mg, 0.87 mmol) portionwise under N$_2$ at 0° C. Then TEA (167 μL, 1.19 mmol) was added. The mixture was stirred at rt overnight. Water (20 mL) was added and the resulting solid was collected, washed firstly with 10% citric acid and then water, and dried over high vacuum. (400 mg, 76% yield, off-white solid)

LC-MS (ESI): [M+1]⁺=667.51, $t_R$=3.63 min.

¹H NMR (400 MHz, MeOD) δ 8.05 (d, J=1.8 Hz, 1H), 7.42 (d, J=4.3 Hz, 1H), 7.38 (d, J=8.7 Hz, 1H), 7.29 (dd, J=8.7, 1.9 Hz, 1H), 7.18 (d, J=2.8 Hz, 1H), 7.01 (dd, J=5.0, 3.6 Hz, 1H), 5.96 (d, J=8.0 Hz, 2H), 4.47 (dd, J=7.6, 4.9 Hz, 1H), 4.29 (dd, J=7.8, 4.4 Hz, 1H), 4.17-4.01 (m, 2H), 3.59-3.38 (m, 4H), 3.27-3.12 (m, 1H), 2.91 (dd, J=12.7, 4.9 Hz, 1H), 2.69 (d, J=12.8 Hz, 1H), 2.64 (dd, J=10.0, 5.7 Hz, 4H), 2.38 (t, J=7.3 Hz, 2H), 2.15-1.92 (m, 31-1), 1.77-1.72 (m, 3H), 1.62 (dd, J=13.6, 7.6 Hz, 1H), 1.50 (dd, J=14.9, 7.4 Hz, 2H), 0.80 (t, J=7.3 Hz, 3H).

¹³C NMR (101 MHz, MeOD) δ 174.28, 170.24, 166.14, 155.34, 150.05, 137.66, 134.37, 131.94, 129.22, 128.22, 128.11, 120.29, 119.46, 113.98, 63.37, 61.65, 61.50, 56.99, 49.60, 49.40, 47.12, 41.08, 37.62, 29.83, 29.53, 26.82, 21.33, 11.35.

HPLC: 99% purity.

HRMS (ESI): calculated for $C_{30}H_{39}N_{10}O_2S_3$ [M+1]⁺= 667.2420; found 667.2450.

6-fluoro-2-(4-(1-(1-(thiophen-2-ylmethyl)-1H-tetrazol-5-yl)propyl)piperazin-1-yl)benzothiazole

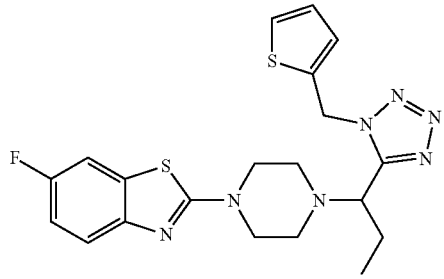 [SMILES: CCC(c1nnnn1Cc1cccs1)N1CCN(c2nc3ccc(F)cc3s2)CC1]

The title compound was prepared according to GP4-3. The crude was firstly purified by flash collumn with DCM/MeOH=300/1 and then by preparative TLC to give the white solid. (300 mg, 34% yield)

LC-MS (ESI): [M+1]⁺=444.33, $t_R$=4.24 min.

¹H NMR (400 MHz, CDCl₃) δ 7.45 (dd, J=11.8, 5.9 Hz, 1H), 7.34-7.25 (m, 2H), 7.07 (d, J=8.7 Hz, 1H), 7.04-6.95 (m, 2H), 3.87 (dd, J=10.2, 4.4 Hz, 1H), 3.62-3.40 (m, 4H), 2.85-2.53 (m, 4H), 2.12-1.95 (m, 2H), 0.82 (t, J=7.3 Hz, 3H).

¹³C NMR (101 MHz, CDCl₃) δ 168.13 (d, J=1.7 Hz), 158.15 (d, J=240.3 Hz), 153.53, 148.99 (d, J=1.6 Hz), 135.36, 131.44 (d, J=10.8 Hz), 127.85, 127.40, 126.94, 119.62 (d, J=8.7 Hz), 113.72 (d, J=23.8 Hz), 107.49 (d, J=27.0 Hz), 61.12, 48.39, 48.36, 46.12, 19.89, 11.26.

HPLC: 99% purity.

HRMS (ESI): calculated for $C_{20}H_{22}N_7FS_2Na$ [M+1]⁺= 466.1260; found 466.1258.

6-methoxy-2-(4-(1-(1-(thiophen-2-ylmethyl)-1H-tetrazol-5-yl)propyl)piperazin-1-yl)benzothiazole

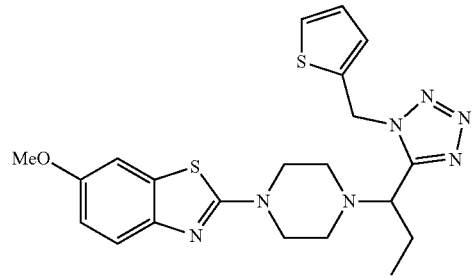 [SMILES: CCC(c1nnnn1Cc1cccs1)N1CCN(c2nc3ccc(OC)cc3s2)CC1]

The title compound was prepared according to GP4-3 as white solid. (109 mg, 24% yield)

LC-MS (ESI): [M+1]⁺=456.25, $t_R$=4.10 min.

¹H NMR (400 MHz, CDCl₃) δ 7.45 (d, J=8.7 Hz, 1H), 7.31 (d, J=4.7 Hz, 1H), 7.14 (s, 1H), 7.06 (s, 1H), 6.99 (t, J=3.9 Hz, 1H), 6.90 (d, J=8.6 Hz, 1H), 5.85 (d, J=4.6 Hz, 2H), 3.85 (dd, J=10.4, 4.1 Hz, 1H), 3.81 (s, 3H), 3.56-3.44 (m, 4H), 2.72-2.59 (m, 4H), 2.12-1.96 (m, 2H), 0.82 (t, J=7.1 Hz, 3H).

¹³C NMR (101 MHz, CDCl₃) δ 167.19, 155.15, 153.56, 146.69, 135.37, 131.75, 127.85, 127.39, 126.92, 119.65, 113.72, 105.19, 61.20, 55.87, 48.44, 48.39, 46.11, 19.80, 11.30.

HPLC: 95% purity.

HRMS (ESI): calculated for $C_{21}H_{26}N_7OS_2$ [M+1]⁺= 456.1640; found 456.1619.

6-chloro-2-(4-(1-(1-(thiophen-2-ylmethyl)-1H-tetrazol-5-yl)propyl)piperazin-1-yl)benzothiazole

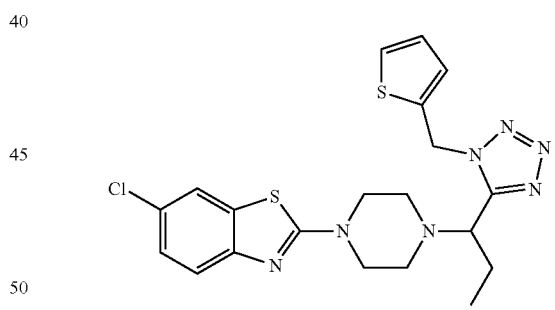

The title compound was prepared according to GP4-3 as white solid. (190 mg, 41% yield)

LC-MS (ESI): [M+1]⁺=460.25, $t_R$=4.44 min.

¹H NMR (400 MHz, CDCl₃) δ 7.55 (d, J=2.1 Hz, 1H), 7.43 (d, J=8.6 Hz, 1H), 7.31 (dd, J=5.1, 0.9 Hz, 1H), 7.24 (dd, J=8.6, 2.1 Hz, 1H), 5.84 (d, J=5.5 Hz, 2H), 3.86 (dd, J=10.2, 4.4 Hz, 1H), 3.62-3.25 (m, 4H), 2.91-2.43 (m, 4H), 2.24-1.91 (m, 2H), 0.82 (t, J=7.3 Hz, 2H).

¹³C NMR (101 MHz, CDCl₃) δ 168.58, 153.49, 151.24, 135.34, 131.94, 127.85, 127.42, 126.94, 126.65, 126.53, 120.42, 119.81, 61.13, 48.40, 48.36, 46.12, 19.89, 11.27.

HPLC: 99% purity.

HRMS (ESI): calculated for $C_{20}H_{22}N_7S_2ClNa$ [M+Na]⁺= 482.0964; found 482.0953.

6-methyl-2-(4-(1-(1-(thiophen-2-ylmethyl)-1H-tetrazol-5-yl)propyl)piperazin-1-yl)benzothiazole

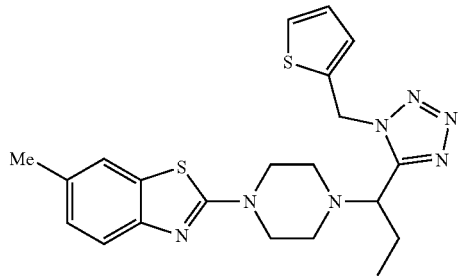 [SMILES: CCC(c1nnnn1Cc1cccs1)N1CCN(c2nc3ccc(C)cc3s2)CC1]

The title compound was prepared according to GP4-3 as white solid. (280 mg, 42% yield)

LC-MS (ESI): [M+1]$^+$=440.28, $t_R$=4.37 min.

$^1$H NMR (400 MHz, CDCl$_3$) δ 7.43 (d, J=8.2 Hz, 1H), 7.40 (s, 1H), 7.31 (dd, J=5.1, 1.0 Hz, 1H), 7.10 (dd, J=8.2, 1.1 Hz, 1H), 7.06 (d, J=3.1 Hz, 1H), 6.99 (dd, J=5.0, 3.6 Hz, 1H), 5.85 (d, J=4.8 Hz, 2H), 3.85 (dd, J=10.3, 4.4 Hz, 1H), 3.62-3.43 (m, 4H), 2.82-2.54 (m, 4H), 2.38 (s, 3H), 2.20-1.92 (m, 2H), 0.82 (t, J=7.3 Hz, 3H).

$^{13}$C NMR (101 MHz, CDCl$_3$) δ 168.03, 153.55, 150.38, 135.37, 131.41, 130.81, 127.84, 127.40, 127.26, 126.92, 120.82, 118.82, 61.22, 48.46, 48.37, 46.12, 21.25, 19.79, 11.30.

HPLC: 99% purity.

HRMS (ESI): calculated for C$_{21}$H$_{25}$N$_7$S$_2$Na [M+Na]$^+$=462.1511; found 462.1511.

6-phenyl-2-(4-(1-(1-(thiophen-2-ylmethyl)-1H-1-tetrazol-5-yl)propyl)piperazin-1-yl)benzothiazole

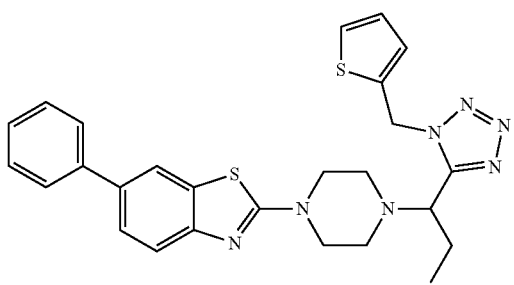 [SMILES: CCC(c1nnnn1Cc1cccs1)N1CCN(c2nc3ccc(-c4ccccc4)cc3s2)CC1]

The title compound was prepared according to GP4-3 as white solid. (218 mg, 56% yield)

LC-MS (ESI): [M+1]$^+$=502.28, $t_R$=4.60 min.

$^1$H NMR (400 MHz, CDCl$_3$) δ 7.81 (s, 1H), 7.59 (d, J=8.1 Hz, 3H), 7.54 (d, J=8.4 Hz, 1H), 7.42 (t, J=7.6 Hz, 2H), 7.33-7.30 (m, 2H), 7.07 (d, J=2.7 Hz, 1H), 7.03-6.96 (m, 1H), 5.85 (d, J=5.0 Hz, 2H), 3.86 (dd, J=10.1, 4.3 Hz, 1H), 3.68-3.45 (m, 4H), 2.80-2.56 (m, 4H), 2.13-1.95 (m, 2H), 0.83 (t, J=7.3 Hz, 3H).

$^{13}$C NMR (101 MHz, CDCl$_3$) δ 168.69, 153.53, 152.01, 140.98, 135.36, 135.07, 131.54, 128.79, 127.83, 127.42, 127.00, 126.91, 126.90, 125.51, 119.27, 119.19, 61.23, 48.48, 48.44, 46.13, 19.87, 11.28.

HPLC: 99% purity.

HRMS (ESI): calculated for C$_{26}$H$_{28}$N$_7$S$_2$ [M+H]$^+$=502.1848; found 502.1864.

2-chloro-N-(2-(4-(1-(1-(thiophen-2-ylmethyl)-1H-tetrazol-5-yl)propyl)piperazin-1-yl)benzothiazol-6-yl)benzamide

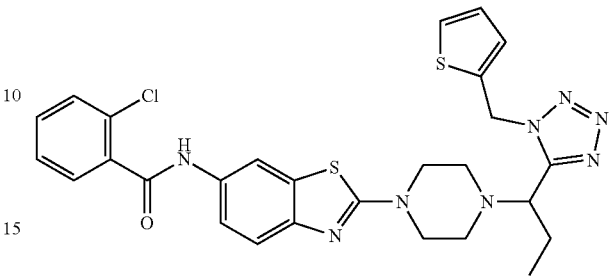

2-chlorobenzoic acid was added to a solution of 6-amino-2-(4-(1-(1-(thiophen-2-ylmethyl)-1H-tetrazol-5-yl)propyl) piperazin-1-yl) benzothiazole (100 mg, 0.227 mmol) in anhydrous DMF (2 mL), followed by addition of HATU (95 mg, 0.250 mmol) portionwise under N$_2$. Then TEA (45 µL, 0.340 mmol) was added. The mixture was stirred at rt overnight. The reaction was poured into water, extracted by EA, dried over Na$_2$SO$_4$, concentrated under reduced pressure and purified by preparative TLC (DCM/Acetone=10/1) to give the product as white powder. (108 mg, 82% yield)

LC-MS (ESI): [M+1]$^+$=579.39, $t_R$=4.13 mm.

$^1$H NMR (400 MHz, CDCl$_3$) δ 8.23 (d, J=1.6 Hz, 1H), 8.11 (s, 1H), 7.65-7.58 (m, 1H), 7.40 (d, J=8.6 Hz, 1H), 7.37-7.10 (m, 5H), 6.99 (d, J=2.9 Hz, 1H), 6.94-6.90 (m, 1H), 5.77 (d, J=4.9 Hz, 2H), 3.78 (dd, J=10.2, 4.2 Hz, 1H), 3.55-3.27 (m, 4H), 2.63-2.53 (m, 4H), 2.02-1.87 (m, 2H), 0.74 (t, J=7.3 Hz, 3H).

$^{13}$C NMR (101 MHz, CDCl$_3$) δ 167.51, 163.46, 152.49, 148.71, 134.29, 134.18, 130.76, 130.59, 110.47, 129.61, 129.30, 129.13, 126.83, 126.37, 126.22, 125.91, 117.99, 117.84, 111.96, 60.11, 47.38, 47.29, 45.09, 18.78, 10.25.

HPLC: 99% purity.

HRMS (ESI): calculated for C$_{27}$H$_{27}$N$_8$OS$_2$ClNa [M+Na]$^+$=601.1335; found 601.1344.

2-methyl-N-(2-(4-(1-(1-(thiophen-2-ylmethyl)-1H-tetrazol-5-yl)propyl)piperazin-1-yl)benzothiazol-6-yl)benzamide

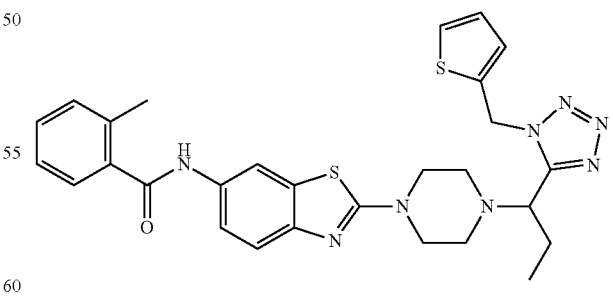

The title compound was prepared according to the procedure above, giving the product as light pink powder. (92 mg, 73% yield)

LC-MS (ESI): [M+1]$^+$=559.36, $t_R$=4.15 min.

$^1$H NMR (400 MHz, CDCl$_3$) δ 8.23 (s, 1H), 7.75 (s, 1H), 7.39-7.37 (m, 2H), 7.28-7.26 (m, 2H), 7.20 (s, 1H), 7.18-

7.11 (m, 3H), 6.99 (d, J=2.8 Hz, 1H), 6.96-6.86 (m, 1H), 5.77 (d, J=4.9 Hz, 2H), 3.78 (dd, J=10.2, 4.2 Hz, 1H), 3.49-3.40 (m, 4H), 2.61-2.51 (m, 4H), 2.41 (s, 3H), 2.06-1.84 (m, 2H), 0.74 (t, J=7.3 Hz, 3H).

$^{13}$C NMR (101 MHz, CDCl$_3$) δ 168.47, 168.06, 153.54, 149.50, 136.44, 135.34, 132.29, 131.51, 131.25, 130.26, 127.87, 127.42, 126.96, 126.65, 125.88, 119.02, 118.68, 112.73, 61.16, 48.42, 48.33, 46.13, 19.89, 19.82, 11.29.

HPLC: 100% purity.

HRMS (ESI): calculated for $C_{28}H_{31}N_8OS_2$ [M+1]$^+$= 559.2062; found 559.2070.

tert-butyl 4-(1-(1-(thiophen-2-ylmethyl)-1H-tetrazol-5-yl)propyl)piperazine-1-carboxylate

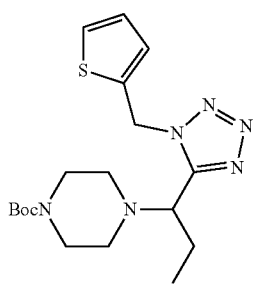 [SMILES: CCC(c1nnnn1Cc1cccs1)N1CCN(C(=O)OC(C)(C)C)CC1]

The title compound was prepared according to GP4-3 using N-Boc piperazine (373 mg, 2.0 mmol) in 2.5 mL of DCM, propionaldehyde (146 μL, 2.0 mmol), TMSN$_3$ (240 μL, 2.0 mmol) and 2-(isocyanomethyl)thiophene (246 mg, 2.0 mmol), as colorless oil (755 mg, 96% yield).

LC-MS (ESI): [M+1]$^+$=393.05, $t_R$=4.07 min.

$^1$H NMR (400 MHz, CDCl$_3$) δ 7.32 (d, J=5.1 Hz, 1H), 7.29 (s, 1H), 7.06 (d, J=3.4 Hz, 1H), 7.02-6.98 (m, 1H), 5.85 (d, J=9.3 Hz, 2H), 3.81 (dd, J=10.2, 4.4 Hz, 1H), 3.46-3.23 (m, 4H), 2.55-2.38 (m, 4H), 2.10-1.90 (m, 2H), 1.44 (s, 9H), 0.80 (t, J=7.3 Hz, 3H).

$^{13}$C NMR (101 MHz, CDCl$_3$) δ 154.54, 153.64, 135.39, 127.83, 127.33, 126.88, 79.88, 61.23, 46.04, 28.37, 19.76, 11.30.

1-(1-(1-(thiophen-2-ylmethyl)-1H-tetrazol-5-yl)propyl)piperazine trihydrochloride

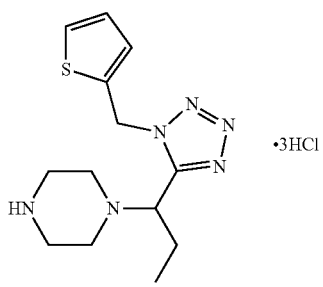 [SMILES: CCC(c1nnnn1Cc1cccs1)N1CCNCC1]

The removal of Boc protection group from tert-butyl 4-(1-(1-(thiophen-2-ylmethyl)-1H-tetrazol-5-yl)propyl)piperazine-1-carboxylate using TFA/DCM combination gave the prominent impurity that was detrimental to the quality of the product, while the protocol below gave the pure product: tert-butyl 4-(1-(1-(thiophen-2-ylmethyl)-1H-tetrazol-5-yl)propyl)piperazine-1-carboxylate (755 mg, 1.92 mmol) in ether (6 mL) 3 mL of 5 M HCl/MeOH was added. The mixture was stirred at rt overnight. The resulting solid was filtered, rinsed by ether and dried to give the white powder (586 mg, 89% yield). The free amine was obtained by neutralization of the salt above by saturated Na$_2$CO$_3$ solution, as off-white solid.

LC-MS (ESI): [M+1]$^+$=293.02, $t_R$=2.87 min.

$^1$H NMR (400 MHz, D$_2$O) δ 7.19 (d, J=5.0 Hz, 1H), 6.93 (d, J=3.2 Hz, 1H), 6.81-6.76 (m, 1H), 5.71 (s, 2H), 4.17 (dd, J=9.9, 4.8 Hz, 1H), 3.02-2.86 (m, 4H), 2.81-2.60 (m, 4H), 1.89-1.67 (m, 2H), 0.44 (t, J=7.3 Hz, 3H).

$^{13}$C NMR (101 MHz, D$_2$O) δ 152.97, 135.13, 128.59, 127.65, 127.45, 59.39, 46.36, 45.59, 42.65, 20.73, 9.33.

HPLC: 95% purity.

HRMS (ESI): calculated for $C_{13}H_{20}N_6SNa$ [M+1]$^+$= 315.1368; found 315.1373.

5,6,7-trimethoxy-2-(4-(1-(1-(thiophen-2-ylmethyl)-1H-tetrazol-5-yl)propyl)piperazin-1-yl)benzothiazole

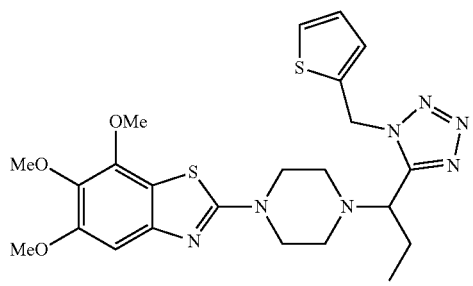 [SMILES: CCC(c1nnnn1Cc1cccs1)N1CCN(c2nc3cc(OC)c(OC)c(OC)c3s2)CC1]

The title compound was prepared according to GP4-3, and preparative TLC purification (DCM/EA=5/1 as eluent) gave the white solid. (192 mg, 37% yield)

LC-MS (ESI): [M+1]$^+$=516.32, $t_R$=4.17 min.

$^1$H NMR (400 MHz, CDCl$_3$) δ 7.32 (d, J=5.0 Hz, 1H), 7.07 (d, J=3.2 Hz, 1H), 7.00 (dd, J=4.9, 3.7 Hz, 1H), 6.91 (s, 1H), 5.85 (d, J=5.1 Hz, 2H), 4.01 (s, 3H), 3.87 (s, 3H), 3.86(s, 3H), 3.59-3.42 (m, 4H), 2.75-2.58 (m, 4H), 2.14-1.94 (m, 2H), 0.82 (t, J=7.3 Hz, 3H).

$^{13}$C NMR (101 MHz, CDCl$_3$) δ 169.05, 153.53, 153.43, 148.73, 146.67, 136.81, 135.36, 127.83, 127.39, 126.91, 114.53, 98.33, 61.46, 61.16, 60.43, 56.20, 48.39, 48.36, 46.10, 19.83, 11.27.

HPLC: 98% purity.

HRMS (ESI): calculated for $C_{23}H_{30}N_7O_3S_2$ [M+1]$^+$= 516.1852; found 516.1836.

7-fluoro-2-(4-(1-(1-(thiophen-2-ylmethyl)-1H-tetrazol-5-yl)propyl)piperazin-1-yl)benzothiazole

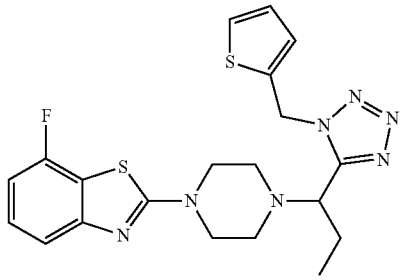

The title compound was prepared according to GP4-3. Preparative TLC purification (DCM/EA=5/1 as eluent) and then recrystallized from ether gave the white solid. (340 mg, 57% yield)

LC-MS (ESI): [M+1]$^+$=444.25, $t_R$=4.35 min.

$^1$H NMR (400 MHz, CDCl$_3$) δ 7.35-7.30 (m, 1H), 7.26-7.20 (m, 1H), 7.07 (d, J=2.7 Hz, 1H), 7.01 (dd, J=5.1, 3.6 Hz, 1H), 6.84-6.78 (m, 1H), 5.85 (d, J=5.4 Hz, 1H), 3.86 (dd, J=10.2, 4.5 Hz, 1H), 3.63-3.49 (m, 4H), 2.75-2.60 (m, 4H), 2.14-1.93 (m, 2H), 0.83 (t, J=7.4 Hz, 3H).

$^{13}$C NMR (101 MHz, CDCl$_3$) δ 169.00, 156.82 (d, J=247.0 Hz), 155.47 (d, J=3.0 Hz), 153.48, 135.33, 127.82, 127.42, 126.91, 126.91 (d, J=3.9 Hz), 117.10 (d, J=16.1 Hz), 114.98 (d, J=3.1 Hz), 107.59 (d, J=18.9 Hz).

HPLC: 99% purity.

HRMS (ESI): calculated for C$_{20}$H$_{22}$N$_7$FS$_2$Na [M+Na]$^+$=466.1260; found 466.1258.

Scheme for Synthesis of 4-amino-2-(4-(1-(1-(thiophen-2-ylmethyl)-1H-tetrazol-5-yl)propyl)piperazin-1-yl)benzothiazole

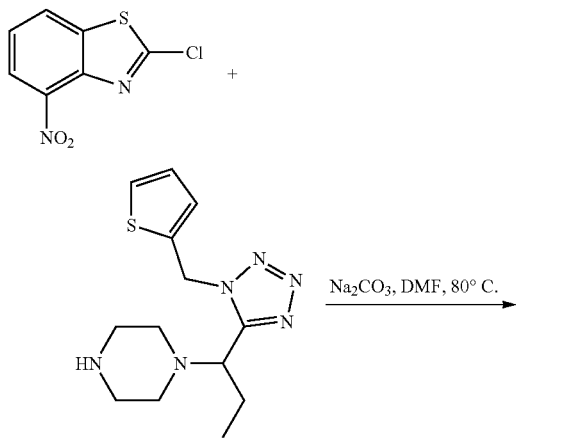

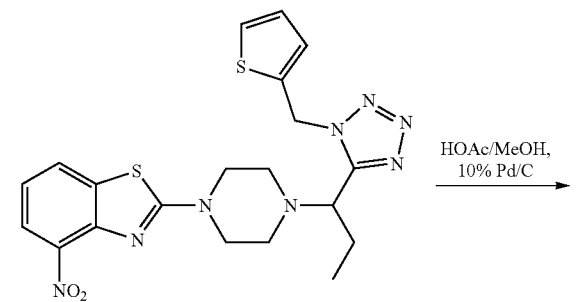

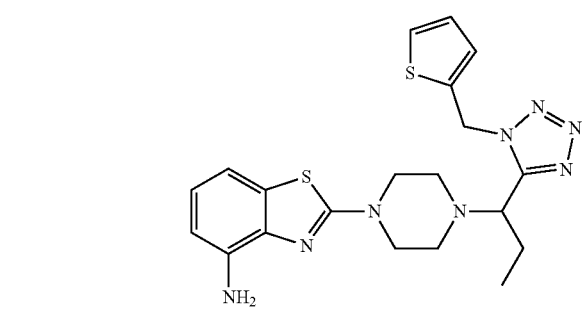

4-nitro-2-(4-(1-(1-(thiophen-2-ylmethyl)-1H-tetrazol-5-yl)propyl)piperazin-1-yl)benzothiazole

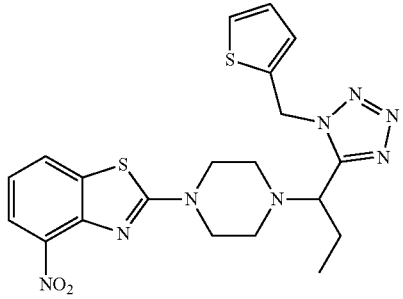 [SMILES: CCC(c1nnnn1Cc1cccs1)N1CCN(c2nc3c([N+](=O)[O-])cccc3s2)CC1]

To a tube 2-chloro-4-nitrobenzothiazole (86 mg, 0.4 mmol), 1-(1-(1-(thiophen-2-ylmethyl)-1H-tetrazol-5-yl)propyl)piperazine (153 mg, 0.5 mmol) and Na$_2$CO$_3$ (53 mg, 0.5 mmol) were added. After N$_2$ flushing, 2 mL of DMF was added, and the mixture was heated to 80° C. for 2 h. Aqueous workup and preparative TLC purification gave the product as brown oil. (52 mg, 28% yield)

LC-MS (ESI): [M+1]$^+$=471.20, $t_R$=4.15 min.

$^1$H NMR (400 MHz, CDCl$_3$) δ 7.98 (d, J=2.3 Hz, 1H), 7.64 (dd, J=8.8, 2.4 Hz, 1H), 7.32 (dd, J=4.8, 0.8 Hz, 1H), 7.11 (d, J=8.8 Hz, 1H), 7.06 (d, J=3.3 Hz, 1H), 7.01 (dd, J=5.0, 3.6 Hz, 1H), 5.85 (d, J=8.9 Hz, 2H), 3.86 (dd, J=10.1, 4.5 Hz, 1H), 3.15-2.97 (m, 4H), 2.77-2.57 (m, 4H), 2.17-1.92 (m, 2H), 0.82 (t, J=7.3 Hz, 3H).

$^{13}$C NMR (101 MHz, CDCl$_3$) δ 153.61, 146.76, 141.56, 136.57, 135.43, 129.94, 127.81, 127.40, 126.88, 122.32, 114.31, 110.10, 61.01, 51.04, 48.72, 46.13, 19.95, 11.26.

4-amino-2-(4-(1-(1-(thiophen-2-ylmethyl)-1H-tetrazol-5-yl)propyl)piperazin-1-yl)benzothiazole

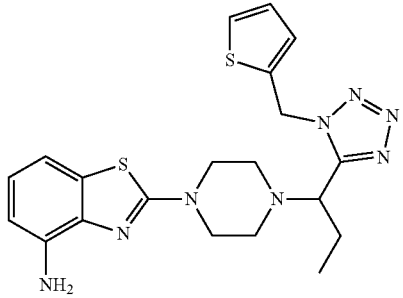

To a suspension of 10% Pd/C wetted by MeOH (1 mL), 4-nitro-2-(4-(1-(1-(thiophen-2-ylmethyl)-1H-tetrazol-5-yl)propyl)piperazin-1-yl)benzothiazole (52 mg, 0.11 mmol) was added, followed by addition of 2 mL of HOAc and 1 mL of MeOH. The reaction was evacuated, refilled back by hydrogen three times and kept stirring at 40° C. for 1.5 hour. After filtering, the volatile was removed. The residue was neutralized and purified by flash column to obtain the product as white foam. (36 mg, 74% yield)

LC-MS (ESI): [M+1]$^+$=441.29, $t_R$=4.17 min.

$^1$H NMR (400 MHz, CDCl$_3$) δ 7.32 (dd, J=5.1, 1.1 Hz, 1H), 7.07 (d, J=2.7 Hz, 1H), 7.01 (dd, J=5.1, 3.6 Hz, 1H), 6.92 (d, J=8.2 Hz, 1H), 6.88-6.82 (m, 2H), 5.88 (d, J=8.3 Hz,

2H), 4.09 (s, 2H), 3.87 (dd, J=9.6, 5.1 Hz, 1H), 2.92-2.55 (m, 8H), 2.17-1.93 (m, 2H), 0.83 (t, J=7.4 Hz, 3H).

$^{13}$C NMR (101 MHz, CDCl$_3$) δ 153.76, 143.06, 140.25, 135.52, 127.85, 127.36, 126.88, 121.05, 120.84, 118.67, 116.58, 111.45, 61.14, 50.74, 49.54, 46.13, 20.32, 11.34.

HPLC: 96% purity.

HRMS (ESI): calculated for C$_{20}$H$_{24}$N$_8$S$_2$Na [M+Na]$^+$= 463.1463; found 463.1449.

2-(4-(1-(1-(thiophen-2-ylmethyl)-1H-tetrazol-5-yl)propyl)piperazin-1-yl)thiazolo[5,4-N]pyridine

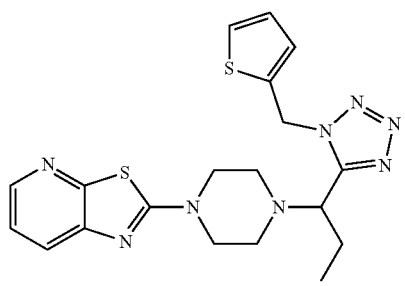 [SMILES: CCC(c1nnnn1Cc1cccs1)N1CCN(c2nc3cccnc3s2)CC1]

The title compound was prepared according to GP4-3. Preparative TLC purification (DCM/EA=5/1 as eluent) and then recrystallized from ether gave the white solid. (100 mg, 23% yield)

LC-MS (ESI). [M+1]$^+$=427.18, t$_R$=3.91 mm.

$^1$H NMR (400 MHz, CDCl$_3$) δ 8.19 (d, J=4.7 Hz, 1H), 7.69 (d, J=8.1 Hz, 1H), 7.32 (d, J=5.0 Hz, 1H), 7.21 (dd, J=8.0, 4.8 Hz, 1H), 7.07 (d, J=2.6 Hz, 1H), 7.01 (t, J=4.0 Hz, 1H), 5.85 (d, J=5.2 Hz, 2H), 3.87 (dd, J=10.1, 4.3 Hz, 1H), 3.66-3.48 (m, 4H), 2.76-2.56 (m, 4H), 2.16-1.92 (m, 2H), 0.83 (t, J=7.3 Hz, 3H).

$^{13}$C NMR (101 MHz, CDCl$_3$) δ 167.29, 155.44, 153.46, 146.79, 142.54, 135.34, 127.81, 127.42, 126.91, 124.89, 121.31, 61.15, 48.43, 48.00, 46.12, 19.94, 11.25.

HPLC: 95% purity.

HRMS (ESI): calculated for C$_{19}$H$_{23}$N$_8$S$_2$ [M+1]$^+$= 427.1487; found 427.1468.

5-fluoro-2-(4-(1-(1-(thiophen-2-ylmethyl)-1H-tetrazol-5-yl)propyl)piperazin-1-yl)benzothiazole

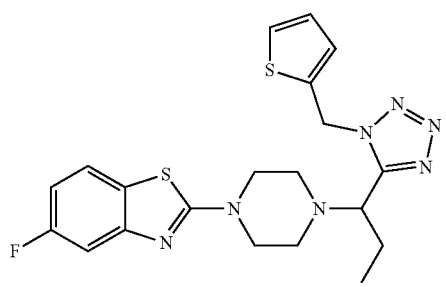 [SMILES: CCC(c1nnnn1Cc1cccs1)N1CCN(c2nc3cc(F)ccc3s2)CC1]

The title compound was prepared according to GP4-3. Preparative TLC purification (DCM/EA=10/1 as eluent) and then recrystallized from ether gave the white solid. (190 mg, 29% yield)

LC-MS (ESI): [M+1]$^+$=444.19, t$_R$=4.31 min.

$^1$H NMR (400 MHz, CDCl$_3$) δ 7.48 (dd, J=8.3, 5.4 Hz, 1H), 7.32 (d, J=5.0 Hz, 1H), 7.23 (d, J=10.1 Hz, 1H), 7.06 (s, 1H), 7.00 (t, J=4.0 Hz, 1H), 6.82 (t, J=8.8 Hz, 1H), 5.84 (d, J=5.6 Hz, 2H), 3.86 (dd, J=10.1, 4.2 Hz, 1H), 3.70-3.45 (m, 4H), 2.79-2.56 (m, 4H), 2.18-1.89 (m, 2H), 0.83 (t, J=7.3 Hz, 3H).

$^{13}$C NMR (101 MHz, CDCl$_3$) δ 170.17, 162.14 (d, J=241.1 Hz), 153.82 (d, J=12.3 Hz), 153.49, 135.35, 127.82, 127.41, 126.91, 125.90 (d, J=2.1 Hz), 121.13 (d, J=10.1 Hz), 109.29 (d, J=24.6 Hz), 106.02 (d, J=24.4 Hz), 61.18, 48.43, 48.32, 46.11, 19.91, 11.25.

HPLC: 95% purity.

HRMS (ESI): calculated for C$_{20}$H$_{23}$N$_7$FS$_2$ [M+1]$^+$= 444.1440; found 444.1442.

2-(4-(1-(1-(thiophen-2-ylmethyl)-1H-tetrazol-5-yl)propyl)piperazin-1-yl)-7-(trifluoromethyObenzothiazole

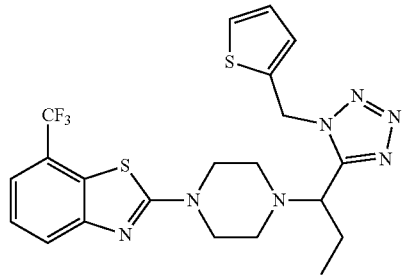

The title compound was prepared according to GP4-3. Preparative TLC purification (DCM/EA=10/1 as eluent) and then recrystallized from ether gave the white solid. (106 mg, 21% yield)

LC-MS (ESI): [M+1]$^+$=494.23, t$_R$=4.56 min.

$^1$H NMR (400 MHz, CDCl$_3$) δ 7.67 (d, J=7.4 Hz, 1H), 7.41-7.29 (m, 3H), 7.07 (d, J=3.0 Hz, 1H), 7.00 (dd, J=5.0, 3.6 Hz, 1H), 5.85 (d, J=4.3 Hz, 2H), 3.88 (dd, J=10.2, 4.5 Hz, 1H), 3.65-3.51 (m, 4H), 2.76-2.60 (m, 4H), 2.15-1.93 (m, 2H), 0.83 (t, J=7.3 Hz, 3H).

$^{13}$C NMR (101 MHz, CDCl$_3$) δ 169.18, 154.10, 153.49, 135.37, 127.82, 127.41, 127.47 (q, J=3.3 Hz), 126.91, 126.02, 123.92 (q, J=271.5 Hz), 123.74 (q, J=25.4 Hz), 122.23, 118.75 (q, J=3.3 Hz), 61.13, 48.41, 48.38, 46.12, 19.95, 11.23.

HPLC: 100% purity.

HRMS (ESI): calculated for C$_{21}$H$_{22}$N$_7$NaS$_2$F$_3$ [M+Na]$^+$= 516.1228; found 516.1235.

N$^1$-(7-fluorobenzothiazol-2-yl)-N$^2$-(1-(1-(thiophen-2-ylmethyl)-1H-tetrazol-5-yl)propyl)ethane-1,2-diamine

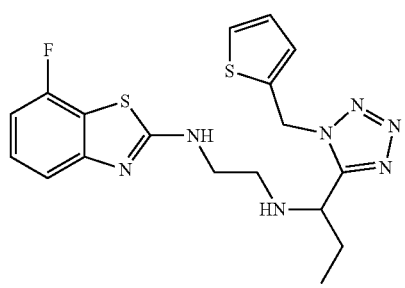 [SMILES: CCC(NCCNc1nc2cccc(F)c2s1)c1nnnn1Cc1cccs1]

The title compound was prepared according to GP4-3. Preparative TLC purification (DCM/EA=2/1 as eluent) gave the oil, which could form HCl salt, precipitating from HCl/ether, as white powder. (169 mg, 21% yield)

LC-MS (ESI): [M+1]$^+$=418.17, $t_R$=3.64 min.

$^1$H NMR (400 MHz, MeOD) δ 7.51 (td, J=8.1, 5.4 Hz, 1H), 7.45 (s, 1H), 7.44 (d, J=3.6 Hz, 1H), 7.35 (d, J=3.1 Hz, 1H), 7.14 (t, J=8.8 Hz, 1H), 6.99 (dd, J=4.9, 3.7 Hz, 1H), 6.15 (d, J=15.9 Hz, 1H), 6.03 (d, J=15.9 Hz, 1H), 5.21 (dd, J=7.7, 5.6 Hz, 1H), 3.98 (t, J=6.0 Hz, 2H), 3.51-3.33 (m, 2H), 2.22-2.09 (m, 2H), 0.69 (t, J=7.4 Hz, 3H).

$^{13}$C NMR (101 MHz, MeOD) δ 170.23, 158.06 (d, J=247.2 Hz), 152.16, 145.09 (d, J=5.5 Hz), 136.67, 130.73 (d, J=7.9 Hz), 130.3, 129.08, 128.2, 113.29 (d, J=20.4 Hz), 112.88 (d, J=3.5 Hz), 111.83 (d, J=18.6 Hz), 54.23, 47.50, 45.87, 43.45, 25.91, 8.99.

HPLC: 94% purity.

HRMS (ESI): calculated for $C_{18}H_{21}N_7S_2F$ [M+1]$^+$= 418.1284; found 418.1282.

5-nitro-2-(4-(1-(1-(thiophen-2-ylmethyl)-1H-tetrazol-5-yl)propyl)piperazin-1-yl)benzothiazole

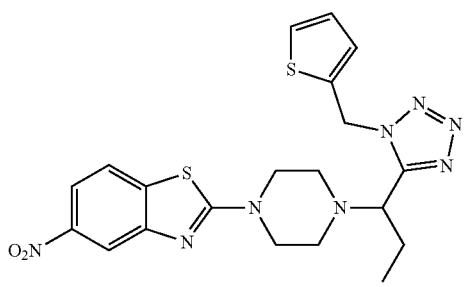 [SMILES: CCC(c1nnnn1Cc1cccs1)N1CCN(c2nc3cc([N+](=O)[O-])ccc3s2)CC1]

The title compound was prepared according to GP4-3, and flash column purification (DCM/EA=100/1 to 50/1 as eluent) gave the desired product as yellow solid. (430 mg, 44% yield)

LC-MS (ESI): [M+1]$^+$=471.23, $t_R$=4.18 min.

$^1$H NMR (400 MHz, CDCl$_3$) δ 8.32 (d, J=2.1 Hz, 1H), 7.95 (dd, J=8.6, 2.2 Hz, 1H), 7.67 (d, J=8.6 Hz, 1H), 7.33 (dd, J=5.1, 1.1 Hz, 1H), 7.07 (d, J=2.7 Hz, 1H), 7.01 (dd, J=5.0, 3.6 Hz, 1H), 5.84 (d, J=6.4 Hz, 2H), 3.88 (dd, J=10.1, 4.6 Hz, 1H), 3.67-3.49 (m, 4H), 2.78-2.60 (m, 4H), 2.25-1.86 (m, 2H), 0.83 (t, J=7.3 Hz, 3H).

$^{13}$C NMR (101 MHz, CDCl$_3$) δ 169.78, 153.41, 153.07, 146.99, 138.00, 135.32, 127.84, 127.45, 126.95, 120.70, 116.27, 113.92, 61.08, 48.48, 48.38, 46.12, 20.09, 11.22.

HPLC: 99% purity.

HRMS (ESI): calculated for $C_{20}H_{22}N_8O_2S_2Na$ [M+Na]$^+$= 493.1205; found 493.1216.

5-amino-2-(4-(1-(1-(thiophen-2-ylmethyl)-1H-tetrazol-5-yl)propyl)piperazin-1-yl)benzothiazole

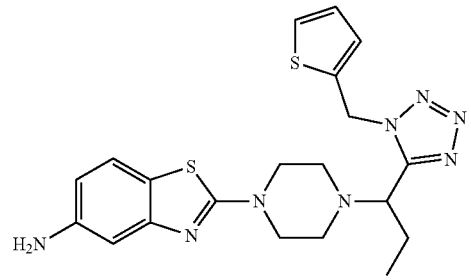

To a suspension of 10% Pd/C wetted by MeOH (2 mL), 5-nitro-2-(4-(1-(1-(thiophen-2-ylmethyl)-1H-tetrazol-5-yl)propyl)piperazin-1-yl)benzothiazole (200 mg, 0.45 mmol) was added, followed by addition of 4 mL of HOAc and 2 mL of MeOH. The reaction was evacuated, refilled back by hydrogen three times and kept stirring at 40° C. for 3.5 hour. The volatile was removed. The residue was neutralized by purified by flash column to obtain the product as yellow oil (57 mg, 29% yield), which was subject to HCl/ether to obtain the HCl salt as brown solid.

LC-MS (ESI): [M+1]$^+$=441.35, $t_R$=3.22 min.

$^1$H NMR (400 MHz, MeOD) δ 7.99 (d, J=8.5 Hz, 1H), 7.68 (d, J=1.7 Hz, 1H), 7.48 (d, J=5.0 Hz, 1H), 7.40 (d, J=3.1 Hz, 1H), 7.33 (dd, J=8.5, 1.7 Hz, 1H), 7.03 (dd, J=4.9, 3.7 Hz, 1H), 6.22 (d, J=15.9 Hz, 1H), 6.08 (d, J=15.9 Hz, 1H), 5.16 (dd, J=10.7, 3.5 Hz, 1H), 4.15 (s, 4H), 3.84-3.75 (m, 2H), 3.62-3.53 (m, 2H), 3.33-3.29 (m, 2H), 2.52-2.13 (m, 2H), 0.57 (t, J=7.2 Hz, 3H).

$^{13}$C NMR (101 MHz, MeOD) δ 171.21, 151.14, 147.59, 136.75, 131.50, 130.40, 129.44, 129.11, 128.33, 124.95, 119.54, 112.88, 60.65, 49.80, 47.70, 47.61, 23.41, 9.63.

HPLC: 95% purity.

HRMS (ESI): calculated for $C_{20}H_{24}N_8S_2Na$ [M+Na]$^+$= 463.1463; found 463.1447.

4-fluoro-2-(4-(1-(1-(thiophen-2-ylmethyl)-1H-tetrazol-5-yl)propyl)piperazin-1-yl)benzothiazole

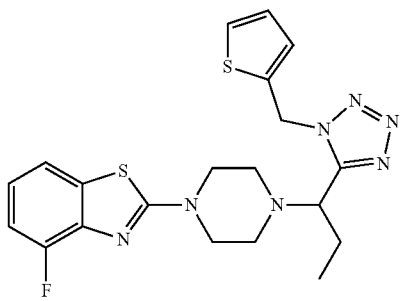 [SMILES: CCC(c1nnnn1Cc1cccs1)N1CCN(c2nc3c(F)cccc3s2)CC1]

The title compound was prepared according to GP4-3, and preparative TLC purification (DCM/EA=10/1 as eluent) gave the desired product as off-white solid. (265 mg, 47% yield)

LC-MS (ESI): [M+1]$^+$=444.22, $t_R$=4.30 min.

$^1$H NMR (400 MHz, CDCl$_3$) δ 7.38-7.34 (m, 1H), 7.32 (dd, J=5.1, 1.0 Hz, 1H), 7.08-6.98 (m, 4H), 5.85 (d, J=5.0

Hz, 1H), 3.86 (dd, J=10.2, 4.5 Hz, 1H), 3.57 (t, J=5.0 Hz, 4H), 2.76-2.57 (m, 4H), 2.18-1.91 (m, 1H), 0.82 (t, J=7.3 Hz, 3H).

$^{13}$C NMR (101 MHz, CDCl$_3$) δ 168.47, 153.51, 153.37 (d, J=250.4 Hz), 140.97 (d, J=13.2 Hz), 135.36, 133.28 (d, J=4.7 Hz), 127.83, 127.41, 126.92, 121.89 (d, J=7.0 Hz), 116.43 (d, J=3.8 Hz), 112.17 (d, J=18.4 Hz), 61.15, 48.44, 48.42, 46.13, 19.94, 11.25.

HPLC: 96% purity.

HRMS (ESI): calculated for C$_{20}$H$_{23}$N$_7$S$_2$F [M+1]$^+$= 444.1440; found 444.1456.

methyl 2-(4-(1-(1-(thiophen-2-ylmethyl)-1H-tetrazol-5-yl)propyl)piperazin-1-yl)benzothiazole-6-carboxylate

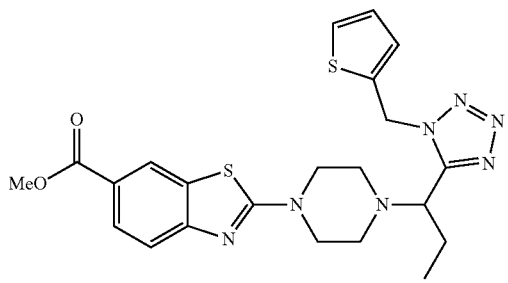 [SMILES: CCC(c1nnnn1Cc1cccs1)N1CCN(c2nc3ccc(C(=O)OC)cc3s2)CC1]

The title compound was prepared according to GP4-3, and preparative TLC purification (DCM/EA=5/1 as eluent) gave the desired product as off-white solid. (200 mg, 24% yield)

LC-MS (ESI): [M+1]$^+$=484.26, t$_R$=4.21 min.

$^1$H NMR (400 MHz, CDCl$_3$) δ 8.30 (s, 1H), 7.99 (d, J=8.5 Hz, 1H), 7.51 (d, J=8.5 Hz, 1H), 7.32 (d, J=5.0 Hz, 1H), 7.07 (d, J=3.1 Hz, 1H), 7.03-6.99 (m, 1H), 5.85 (d, J=5.5 Hz, 2H), 3.66-3.53 (m, 4H), 2.78-2.59 (m, 4H), 2.16-1.93 (m, 2H), 0.83 (t, J=7.3 Hz, 3H).

$^{13}$C NMR (101 MHz, CDCl$_3$) δ 170.58, 166.93, 156.45, 153.45, 135.30, 130.64, 128.01, 127.85, 127.45, 126.96, 123.19, 122.81, 118.43, 61.13, 52.07, 48.41, 46.13, 19.89, 11.27.

HPLC: 100% purity.

HRMS (ESI): calculated for C$_{22}$H$_{25}$N$_7$O$_2$S$_2$Na [M+Na]$^+$= 506.1409; found 506.1431.

2-(4-(1-(1-(thiophen-2-ylmethyl)-1H-tetrazol-5-yl) propyl)piperazin-1-yl)benzothiazole-6-carboxylic acid

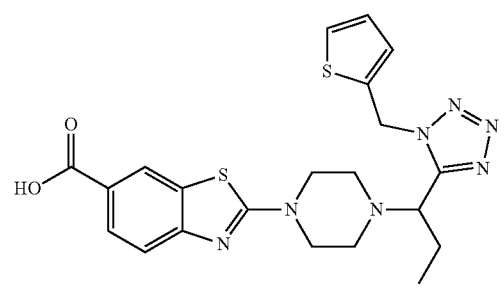 [SMILES: CCC(c1nnnn1Cc1cccs1)N1CCN(c2nc3ccc(C(=O)O)cc3s2)CC1]

Methyl 2-(4-(1-(1-(thiophen-2-ylmethyl)-1H-tetrazol-5-yl)propyl)piperazin-1-yl)benzothiazole-6-carboxylate (120 mg, 0.25 mmol) in 1.5 mL of THF and 1.5 mL MeOH, was added by 0.7 mL of 2 M of LiOH solution and the mixture was heated to 40° C. for 4 h, which was monitored by LC-MS. After completion, the reaction was neutralized by 1 M HCl and the resulting white solid was collected and dried over high vacuum. (105 mg, 89% yield)

LC-MS (ESI): [M+1]$^+$=470.10, t$_R$=3.80 min.

$^1$H NMR (400 MHz, d6-DMSO) δ 12.70 (s, 1H), 8.36 (d, J=1.2 Hz, 1H), 7.85 (dd, J=8.5, 1.5 Hz, 1H), 7.56 (d, J=5.0 Hz, 1H), 7.45 (d, J=8.5 Hz, 1H), 7.25 (d, J=3.0 Hz, 1H), 7.04 (dd, J=4.9, 3.7 Hz, 1H), 5.99 (d, J=9.6 Hz, 2H), 4.27 (dd, J=9.2, 5.4 Hz, 1H), 3.60-3.45 (m, 4H), 2.67-2.57 (m, 4H), 2.04-1.83 (m, 2H), 0.76 (t, J=7.3 Hz, 3H).

$^{13}$C NMR (101 MHz, d6-DMSO) δ 170.21, 167.04, 156.07, 153.50, 136.62, 130.39, 128.25, 127.61, 127.42, 127.04, 123.22, 123.02, 117.78, 58.54, 48.10, 47.54, 45.17, 20.30, 10.79.

HPLC: 100% purity.

HRMS (ESI): calculated for C$_{21}$H$_{23}$N$_7$O$_2$S$_2$Na [M+Na]$^+$= 492.1252; found 492.1264.

Scheme for Synthesis of (4-(7-fluorobenzothiazol-2-yl)piperazin-1-yl)(1-(thiophen-2-ylmethyl)-1H-tetrazol-5-yl)methanone{Demko, 2002 #619}

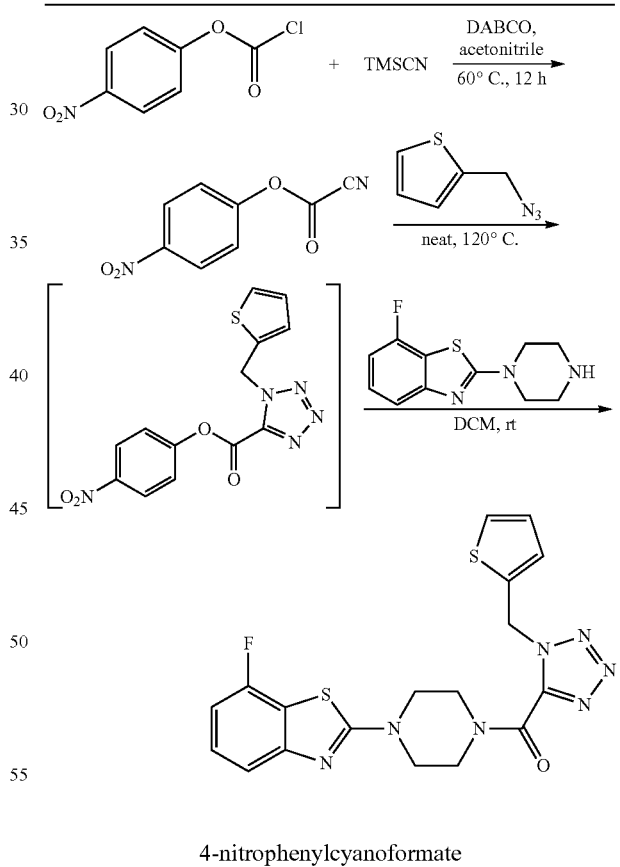

4-nitrophenylcyanoformate

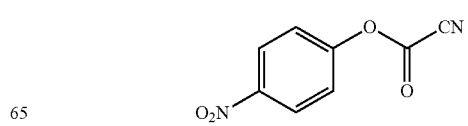

A flask was charged with p-nitrophenyl chloroformate (10.2 g, 50.0 mmol), trimethylsilyl cyanide (6.9 g, 70.0 mmol), DABCO (28 mg, 0.5 mol %) and $CH_3CN$ (20 mL). The mixture was stirred at 60° C. under $N_2$ atmosphere for 12 h. After that, the volatile was evaporated under reduced pressure. The solid was dissolved in 100 mL of chloroform and filtered through a pad of Celite, evaporated the solvent to 30 mL. The resulting solid was collected, washed by minimum of chloroform, and dried over high vacuum to give the product as off-white solid. (4.5 g, 47% yield)

$^1$H NMR (400 MHz, $CDCl_3$) δ 8.37 (d, J=9.1 Hz, 2H), 7.45 (d, J=9.1 Hz, 2H).

$^{13}$C NMR (101 MHz, $CDCl_3$) δ 152.93, 146.63, 141.46, 125.82, 121.79, 108.54.

(4-(7-fluorobenzothiazol-2-yl)piperazin-1-yl)(1-(thiophen-2-ylmethyl)-1H-tetrazol-5-yl)methanone

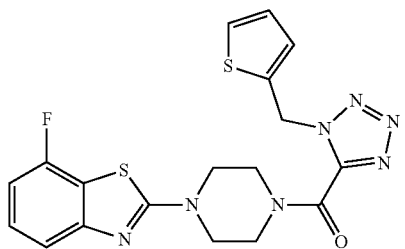 [SMILES: O=C(c1nnnn1Cc1cccs1)N1CCN(c2nc3cccc(F)c3s2)CC1]

A tube was charged with 4-nitrophenylcyanoformate (634 mg, 3.3 mmol) and 2-(azidomethyl)thiophene (418 mg, 3.0 mmol) and heated at 120° C. under $N_2$ for 16 h.

Then the reaction was cooled and dissolved in 10 mL of DCM, which was added to 7-fluoro-2-(piperazin-1-yl)benzothiazole (854 mg, 3.6 mmol) in 5 mL of DCM. The mixture was stirred at rt for 2 h. The organic layer was washed by 1 M NaOH, evaporated, purified by column chromatography (PE/EA=5/1 to 3/1) and triturated by acetone in ether (1/2) to get the product as white powder. (512 mg, 40% yield)

LC-MS (ESI): [M+1]$^+$=429.96, $t_R$=4.18 min.

$^1$H NMR (400 MHz, $CDCl_3$) δ 7.37 (d, J=8.0 Hz, 1H), 7.34-7.26 (m, 2H), 7.20 (d, J=3.1 Hz, 1H), 6.97 (t, J=4.2 Hz, 1H), 6.86 (t, J=8.7 Hz, 1H), 6.04 (s, 2H), 4.01-3.95 (m, 4H), 3.76 (t, J=5.0 Hz, 2H), 3.55 (t, J=5.0 Hz, 2H).

HPLC: 98% purity.

HRMS (ESI): calculated for $C_{18}H_{16}N_7OS_2FNa$ [M+Na]$^+$= 452.0739; found 452.0734.

7-bromo-2-(4-(1-(1-(thiophen-2-ylmethyl)-1H-tetrazol-5-yl)propyl)piperazin-1-yl)benzothiazole

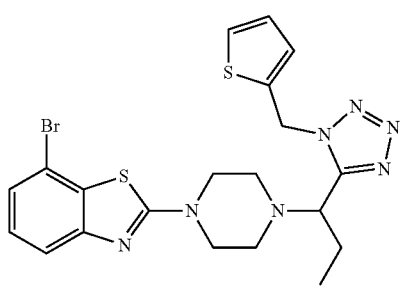 [SMILES: CCC(c1nnnn1Cc1cccs1)N1CCN(c2nc3cccc(Br)c3s2)CC1]

To a tube 2-chloro-7-bromobenzothiazole (95 mg, 0.39 mmol), 1-(1-(1-(thiophen-2-ylmethyl)-1H-tetrazol-5-yl)propyl)piperazine (102 mg, 0.35 mmol) and $Na_2CO_3$ (55 mg, 0.52 mmol) were added. After $N_2$ flushing, 2 mL of DMF was added, and the mixture was heated to 80° C. for 5 h. Aqueous workup and preparative flash column purification gave the product as white powder. (60 mg, 34% yield)

LC-MS (ESI): [M+1]$^+$=504.20, $t_R$=4.56 min.

$^1$H NMR (400 MHz, $CDCl_3$) δ 7.44 (dd, J=7.3, 1.5 Hz, 1H), 7.31 (d, J=5.1 Hz, 1H), 7.21-7.12 (m, 2H), 7.06 (d, J=2.8 Hz, 1H), 7.00 (dd, J=4.9, 3.7 Hz, 1H), 5.84 (d, J=4.6 Hz, 2H), 5.84 (d, J=4.6 Hz, 2H), 3.87 (dd, J=10.2, 4.4 Hz, 1H), 3.61-3.43 (m, 4H), 2.76-2.54 (m, 4H), 2.16-1.93 (m, 2H), 0.82 (t, J=7.3 Hz, 3H).

$^{13}$C NMR (101 MHz, $CDCl_3$) δ 167.61, 153.50, 152.71, 135.37, 133.46, 127.83, 127.41, 127.27, 126.92, 124.25, 117.76, 113.08, 61.13, 48.40, 48.29, 46.13, 19.93, 11.26.

HPLC: 99% purity.

HRMS (ESI): calculated for $C_{20}H_{23}N_7S_2Br$ [M+1]$^+$= 504.0640; found 504.0622.

Methyl 2-(4-(1-(1-(thiophen-2-ylmethyl)-1H-tetrazol-5-yl)propyl)piperazin-1-yl)benzothiazole-7-carboxylate

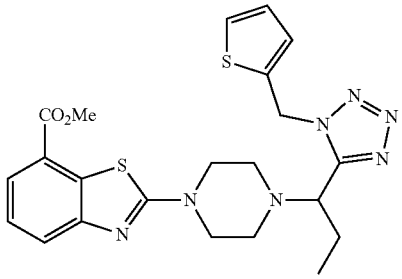 [SMILES: CCC(c1nnnn1Cc1cccs1)N1CCN(c2nc3cccc(C(=O)OC)c3s2)CC1]

The title compound was prepared according to GP4-3, and preparative TLC purification (DCM/EA=5/1 as eluent) gave the desired product as off-white solid. (240 mg, 19% yield)

LC-MS (ESI): [M+1]$^+$=484.28, $t_R$=4.25 min.

$^1$H NMR (400 MHz, $CDCl_3$) δ 7.78 (d, J=7.7 Hz, 1H), 7.71 (d, J=8.0 Hz, 1H), 7.37 (t, J=7.8 Hz, 1H), 7.32 (d, J=5.1 Hz, 1H), 7.07 (d, J=3.2 Hz, 1H), 7.00 (t, J=4.2 Hz, 1H), 5.85 (d, J=4.4 Hz, 2H), 3.98 (s, 3H), 3.86 (dd, J=10.2, 4.3 Hz, 1H), 3.70-3.52 (m, 4H), 2.78-2.58 (m, 4H), 2.19-1.92 (m, 2H), 0.83 (t, J=7.3 Hz, 3H).

$^{13}$C NMR (101 MHz, $CDCl_3$) δ 170.80, 166.73, 153.82, 153.51, 135.36, 132.29, 127.82, 127.41, 126.91, 125.81, 123.33, 123.19, 122.91, 77.34, 77.02, 76.71, 61.24, 52.47, 48.50, 48.17, 46.12, 19.88, 11.27.

HPLC: 98% purity.

HRMS (ESI): calculated for $C_{22}H_{23}N_7O_2S_2Na$ [M+Na]$^+$= 506.1409; found 506.1411.

2-(4-(1-(1-(thiophen-2-ylmethyl)-1H-tetrazol-5-yl)propyl)piperazin-1-yl)benzothiazole-7-carboxylic acid

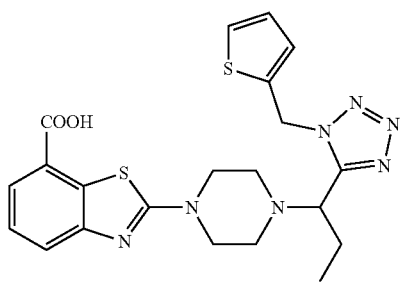 [SMILES: CCC(c1nnnn1Cc1cccs1)N1CCN(c2nc3cccc(C(=O)O)c3s2)CC1]

Methyl 2-(4-(1-(1-(thiophen-2-ylmethyl)-1H-tetrazol-5-yl)propyl)piperazin-1-yl)benzothiazole-7-carboxylate (180 mg, 0.37 mmol) in 2 mL of THF and 2 mL MeOH, was added by 1 mL of 2 M of LiOH solution and the mixture was heated to 40° C. overnight. The reaction was neutralized by 1 M HCl and the resulting white solid was collected and dried over high vacuum. (150 mg, 86% yield)

LC-MS (ESI): [M+1]$^+$=470.29, $t_R$=3.82 min.

$^1$H NMR (400 MHz, DMSO) δ 7.71-7.63 (m, 2H), 7.55 (d, J=5.0 Hz, 1H), 7.40 (t, J=7.8 Hz, 1H), 7.26 (d, J=2.7 Hz, 1H), 7.08-7.01 (m, 1H), 6.00 (d, J=8.4 Hz, 2H), 4.28 (dd, J=8.6, 5.1 Hz, 1H), 3.64-3.51 (m, 4H), 2.68-2.57 (m, 4H), 2.05-1.83 (m, 21-1), 0.75 (t, J=7.2 Hz, 3H).

$^{13}$C NMR (101 MHz, DMSO) δ 170.18, 166.99, 153.54, 153.47, 136.58, 131.45, 128.27, 127.41, 127.04, 125.94, 123.88, 122.58, 122.46, 58.36, 47.81, 47.61, 45.20, 20.30, 10.75.

HPLC: 96% purity.

HRMS (ESI): calculated for $C_{21}H_{23}N_7O_2S_2Na$ [M+Na]$^+$= 492.1252; found 492.1271.

7-hydroxyl-2-(4-(1-(1-(thiophen-2-ylmethyl)-1H-tetrazol-5-yl)propyl)piperazin-1-yl)benzothiazole

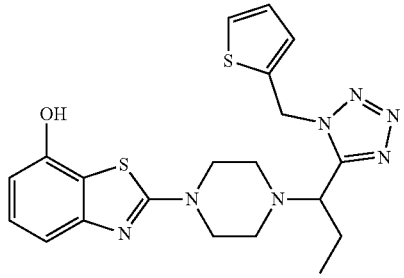 [SMILES: CCC(c1nnnn1Cc1cccs1)N1CCN(c2nc3cccc(O)c3s2)CC1]

The title compound was prepared according to GP4-3. After the consumption of the starting material, TBAF (180 mg) was added and stirring was kept at rt until the trimethylsilylated intermediate was totally transformed into the desired product. Flash column purification (DCM/EA=5/1 as eluent) gave the pure product as off-white solid. (50 mg, 25% yield)

LC-MS (ESI): [M+1]$^+$=442.59, $t_R$=3.71 min.

$^1$H NMR (400 MHz, d6-acetone) δ 9.09 (s, 1H), 7.47 (d, J=5.0 Hz, 1H), 7.25 (d, J=3.0 Hz, 1H), 7.10 (t, J=7.9 Hz, 1H), 7.03 (t, J=7.1 Hz, 2H), 6.60 (d, J=7.8 Hz, 2H), 4.21-4.16 (t, J=7.4 Hz, 1H), 3.65-3.47 (m, 4H), 2.71 (m, 4H), 2.07-1.99 (m, 2H), 0.83 (t, J=7.2 Hz, 3H).

$^{13}$C NMR (101 MHz, d6-acetone) δ 169.50, 155.85, 154.62, 152.31, 137.72, 128.92, 127.95, 127.83, 127.51, 118.22, 111.93, 107.89, 61.12, 49.27, 48.97, 46.57, 20.76, 11.51.

HPLC: 96% purity.

HRMS (ESI): calculated for $C_{20}H_{24}N_7OS_2$ [M+1]$^+$= 442.1484; found 442.1494.

Scheme for Synthesis of 2-(4-(1-(1-(thiophen-2-ylmethyl)-1H-tetrazol-5-yl)propyl)phenyl)benzothiazole

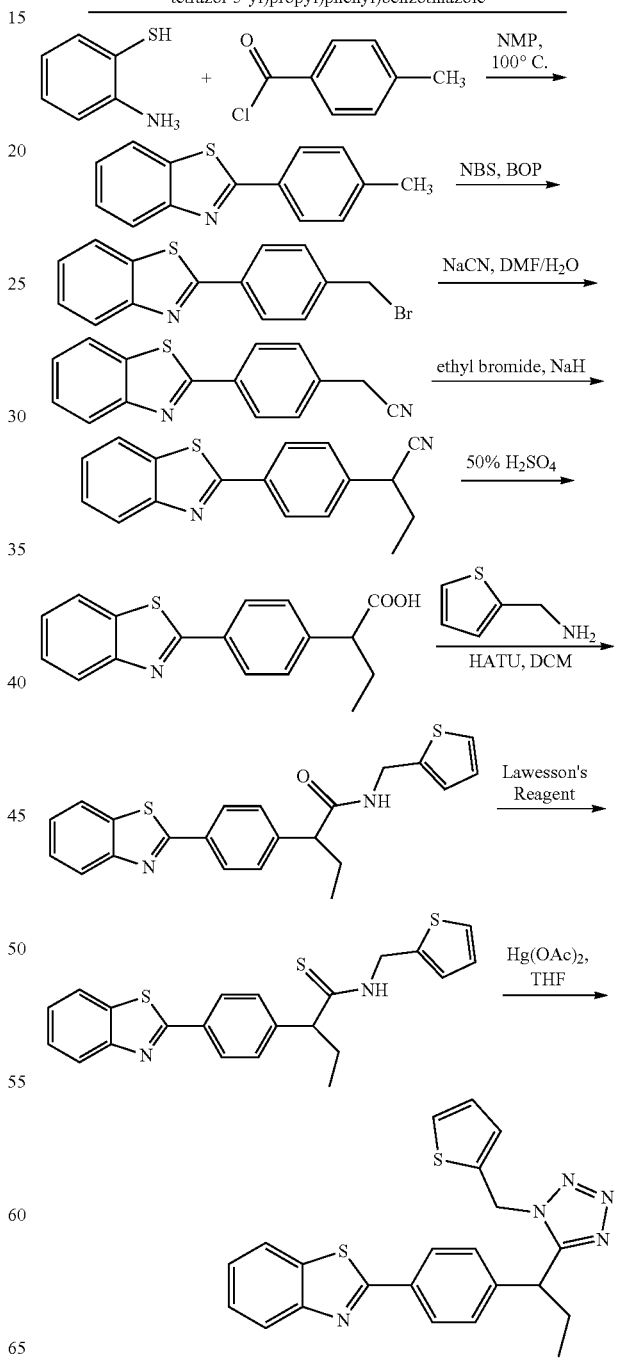

2-(p-tolyl)benzothiazole

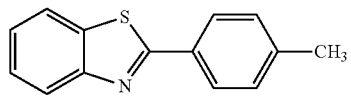 [SMILES: Cc1ccc(-c2nc3ccccc3s2)cc1]

To a solution of 4-methylbenzyl chloride (3.1 g, 20.0 mmol) in 50 mL of NMP, 2-aminobenzenethiol (3.1 g, 20.0 mmol) was added. The mixture was heated to 100° C. for 2 hours. The mixture was cooled down to rt, and saturated $Na_2CO_3$ solution was added, followed by 20 mL of water. The resulting white solid was filtered, washed by water and dried over high vacuum. (3.6 g, 55% yield)

LC-MS (ESI): $[M+1]^+$=226.13, $t_R$=4.59 min.
$^1$H NMR (400 MHz, $CDCl_3$) δ 8.05 (d, J=8.1 Hz, 1H), 7.97 (d, J=8.1 Hz, 2H), 7.87 (d, J=7.9 Hz, 1H), 7.47 (t, J=7.5 Hz, 1H), 7.35 (t, J=7.5 Hz, 1H), 7.28 (d, J=7.9 Hz, 2H), 2.41 (s, 3H).
$^{13}$C NMR (101 MHz, $CDCl_3$) δ 168.27, 154.18, 141.45, 134.96, 130.96, 129.75, 127.50, 126.27, 125.02, 123.06, 121.60, 21.56.

2-(4-(bromomethyl)phenyl)benzothiazole

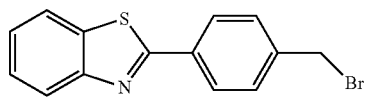 [SMILES: BrCc1ccc(-c2nc3ccccc3s2)cc1]

2-(p-tolyl)benzothiazole (3.4 g, 15.0 mmol), NBS (2.7 g, 15.0 mmol) and catalytic amount of benzoyl peroxide (36 mg, 1 mol %) were dissolved in $CCl_4$ (50 mL). The mixture was heated to reflux for 9 hours. The reaction was quenched by $Na_2SO_3$ solution and extracted by $CCl_4$ twice. Collected organic layers were washed by brine, dried over $Na_2SO_4$ and concentrated to give the crude, which was recrystallized from hot EtOH to give the light purple solid. NMR showed mono-brominated and dibrominated products were in a molar ratio of 6:1. (3.2 g, 70% yield)

LC-MS (ESI): $[M+1]^+$=304.00, $t_R$=3.50 min.
$^1$H NMR (400 MHz, $CDCl_3$) δ 8.10-8.04 (m, 3H), 7.92-7.88 (m, 1H), 7.53-7.47 (m, 3H), 7.43-7.35 (m, 1H), 4.52 (s, 1H).

2-(4-(benzothiazol-2-yl)phenyl)acetonitrile

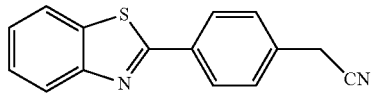

To a solution of 2-(4-(bromomethyl)phenyl)benzothiazole (2.8 g, 9.2 mmol) dissolved in 30 mL of DMF were added by NaCN (540 mg, 11.0 mmol) and water (3 mL). The mixture was stirred at rt for 1 h. The mixture was diluted with EA (50 mL), washed by 1 M of NaOH, 1 M of HCl and brine, extracted by EA (50 mL). Collected organic layers were dried over $Na_2SO_4$, concentrated and purified by silica gel (PE/EA=2/1 to 1/2) to get off-white powder. (1.3 g, 50% yield)

LC-MS (ESI): $[M+1]^+$=251.22, $t_R$=4.05 min.
$^1$H NMR (400 MHz, $CDCl_3$) δ 8.11-8.05 (m, 3H), 7.90 (d, J=8.0 Hz, 1H), 7.50 (t, J=7.7 Hz, 1H), 7.44 (d, J=8.1 Hz, 2H), 7.39 (t, J=7.6 Hz, 1H), 3.80 (s, 2H).
$^{13}$C NMR (101 MHz, $CDCl_3$) δ 166.89, 154.08, 135.07, 133.55, 132.65, 128.59, 128.22, 126.50, 125.47, 123.36, 121.69, 117.30, 23.57.

2-(4-(benzothiazol-2-yl)phenyl)butanenitrile

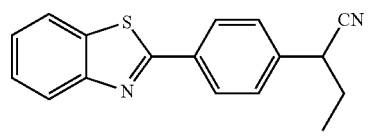 [SMILES: CCC(C#N)c1ccc(-c2nc3ccccc3s2)cc1]

2-(4-(benzothiazol-2-yl)phenyl)acetonitrile dissolved in THF (1.14 g, 4.55 mmol), was added by 60% of NaH in mineral oil (182 mg, 4.55 mmol). The suspension was stirred at for 10 min, and then ethyl bromide (560 mg, 4.55 mmol) was added. Stirring was kept for 4 hours before the reaction was quenched by 1 M of HCl. After extraction by EA (50 mL), the combined organic layers were dried over $Na_2SO_4$. Purification of the crude (PE/EA=20/1 to 10/1) gave the off-white solid. (765 mg, 60% yield)

LC-MS (ESI): $[M+1]^+$=279.13, $t_R$=4.36 min.

2-(4-(benzothiazol-2-yl)phenyl)butanoic acid

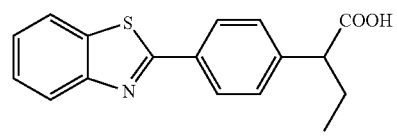 [SMILES: CCC(C(=O)O)c1ccc(-c2nc3ccccc3s2)cc1]

2-(4-(benzothiazol-2-yl)phenyl)butanenitrile (765 mg, 2.75 mmol) in 50% of $H_2SO_4$ solution was heated at 90° C. for 12 hours. Neutralized carefully by 10% NaOH under ice-cooled condition, the resulting off-white solid was collected, washed by water and dried over high vacuum. (776 mg, 95% yield)

LC-MS (ESI): $[M+1]^+$=298.28, $t_R$=4.10 min.
$^1$H NMR (400 MHz, $CDCl_3$) δ 8.08 (d, J=8.1 Hz, 1H), 8.03 (d, J=8.2 Hz, 2H), 7.88 (d, J=7.9 Hz, 1H), 7.49 (t, J=7.3 Hz, 1H), 7.45 (d, J=8.2 Hz, 2H), 7.38 (t, J=7.5 Hz, 1H), 3.55 (t, J=7.6 Hz, 1H), 2.24-2.09 (m, 1H), 1.94-1.79 (m, 1H), 0.95 (t, J=7.4 Hz, 3H).
$^{13}$C NMR (101 MHz, $CDCl_3$) δ 178.43, 167.96, 153.89, 141.75, 134.92, 132.62, 128.84, 127.90, 126.42, 125.28, 123.13, 121.63, 53.21, 26.34, 12.08.

2-(4-(benzothiazol-2-yl)phenyl)-N-(thiophen-2-ylmethyl)butanamide

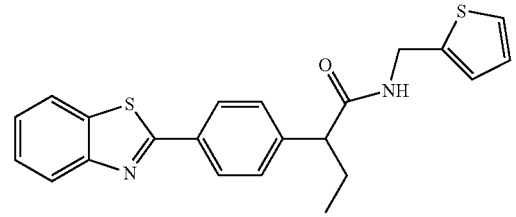

2-(4-(benzothiazol-2-yl)phenyl)butanoic acid (762 mg, 2.56 mmol), HATU (1.02 g, 2.69 mmol) and Et₃N (0.7 mL, 5.12 mmol) were dissolved in DCM (12 mL) and 2-thiophenemethylamine (305 mg, 2.69 mmol) was added to the solution. The mixture was stirred at rt overnight, washed by 1 M of HCl, saturated Na₂CO₃ and brine. After extracting by DCM, collected organic layers were dried over Na₂SO₄ and concentrated to get the crude, which was triturated by 10% ether in PE to give the product as white solid. (910 mg, 91%)

LC-MS (ESI): [M+1]⁺=393.45, $t_R$=4.30 min.

¹H NMR (400 MHz, CDCl₃) δ 8.04 (t, J=8.5 Hz, 3H), 7.90 (d, J=7.9 Hz, 1H), 7.49 (t, J=7.6 Hz, 1H), 7.43 (d, J=8.2 Hz, 2H), 7.38 (t, J=7.6 Hz, 1H), 7.18 (d, J=4.9 Hz, 1H), 6.89 (dd, J=9.1, 4.2 Hz, 2H), 5.94 (s, 1H), 4.58 (qd, J=15.3, 5.7 Hz, 2H), 3.30 (t, J=7.5 Hz, 1H), 2.31-2.15 (m, 1H), 1.94-1.79 (m, 1H), 0.92 (t, J=7.3 Hz, 3H).

¹³C NMR (101 MHz, CDCl₃) δ 172.51, 167.66, 154.14, 142.91, 140.96, 135.04, 132.67, 128.70, 127.95, 126.83, 126.37, 125.80, 125.23, 125.19, 123.19, 121.64, 55.07, 38.51, 26.59, 12.30.

2-(4-(benzothiazol-2-yl)phenyl)-N-(thiophen-2-ylmethyl)butanethioamide

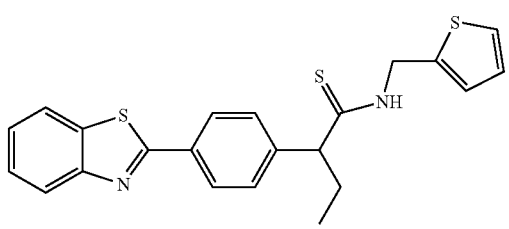 [SMILES: CCC(C(=O)NCc1cccs1)c1ccc(-c2nc3ccccc3s2)cc1]

A suspension of 2-(4-(benzothiazol-2-yl)phenyl)-N-(thiophen-2-ylmethyl)butanamide in toluene (20 mL) was treated with Lawesson's reagent. The mixture was heated to 80° C. After 15 min, the mixture became clear and stirred at temperature for additional 1 hour. Purification of the crude (PE/EA=5/1) gave the product as light greenish foam. (894 mg, 94% yield)

LC-MS (ESI): [M+1]⁺=409.60, $t_R$=4.65 min.

¹H NMR (400 MHz, CDCl₃) δ 8.20-7.97 (m, 3H), 7.89 (d, J=7.9 Hz, 1H), 7.69 (s, 1H), 7.51 (d, J=5.7 Hz, 2H), 7.41 (t, J=7.5 Hz, 1H), 7.20 (d, J=4.9 Hz, 1H), 6.92 (dd, J=10.5, 6.1 Hz, 2H), 6.17 (brs, 1H), 4.98 (qd, J=15.4, 4.7 Hz, 1H), 3.89-3.80 (m, 1H), 2.48-2.31 (m, 1H), 2.06-1.88 (m, 1H), 0.90 (t, J=7.2 Hz, 3H).

¹³C NMR (101 MHz, CDCl₃) δ 205.48, 168.82, 151.85, 144.13, 138.20, 133.92, 131.24, 128.95, 128.29, 127.11, 127.03, 126.94, 125.85, 125.83, 122.63, 121.76, 62.44, 44.56, 28.64, 12.25.

2-(4-(1-(1-(thiophen-2-ylmethyl)-1H-tetrazol-5-yl)propyl)phenyl)benzothiazole {Panday, 2000 #847}

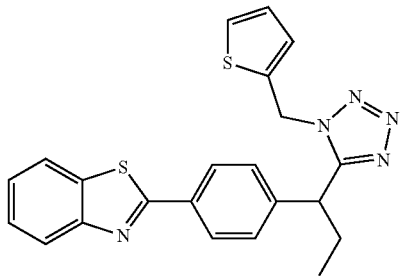 [SMILES: CCC(c1ccc(-c2nc3ccccc3s2)cc1)c1nnnn1Cc1cccs1]

A solution of 2-(4-(benzothiazol-2-yl)phenyl)-N-(thiophen-2-ylmethyl)butanethioamide (409 mg, 1.00 mmol) and Hg(OAc)₂ (335 mg, 1.05 mmol) in THF (5 mL) was treated with TMSN₃ (138 μL, 1.05 mmol) and stirred at rt overnight. The mixture was quenched by saturated Na₂CO₃ and filtered through a pad of Celite. The filtrate dried and concentrate to give the crude, which was purified by preparative TLC then recrystallized from methanol to give the product as white solid. (55 mg, 13% yield)

LC-MS (ESI): [M+1]⁺=418.61, $t_R$=4.45 min.

¹H NMR (400 MHz, CDCl₃) δ 8.07 (d, J=8.1 Hz, 1H), 8.02 (d, J=7.7 Hz, 2H), 7.90 (d, J=7.8 Hz, 1H), 7.50 (t, J=7.5 Hz, 1H), 7.39 (t, J=7.4 Hz, 1H), 7.28 (d, J=8.0 Hz, 2H), 7.25 (d, J=5.2 Hz, 1H), 6.88 (d, J=17.7 Hz, 2H), 5.63 (d, J=15.8 Hz, 1H), 5.34 (d, J=15.8 Hz, 1H), 4.00 (t, J=7.3 Hz, 1H), 2.45-2.35 (m, 1H), 2.20-2.10 (m, 1H), 0.90 (t, J=7.1 Hz, 3H).

¹³C NMR (101 MHz, CDCl₃) δ 167.08, 155.89, 154.11, 141.67, 135.06, 134.84, 133.20, 128.56, 128.21, 127.77, 127.31, 127.07, 126.47, 125.41, 123.30, 121.69, 45.71, 42.95, 28.78, 12.10.

HPLC: 94% purity.

HRMS (ESI): calculated for C₂₂H₂₀N₅S₂ [M+1]⁺= 418.1160; found 418.1151.

7-fluoro-2-(4-(1-(1-(2-(thiophen-2-yl)ethyl)-1H-tetrazol-5-yl)propyl)piperazin-1-yl)benzothiazole

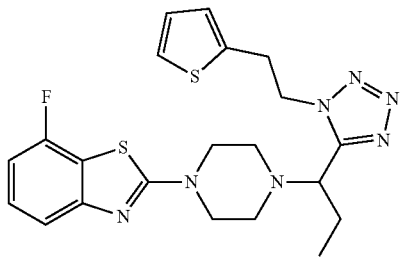 [SMILES: CCC(c1nnnn1CCc1cccs1)N1CCN(c2nc3cccc(F)c3s2)CC1]

The title compound was prepared according to GP4-3 using propionaldehyde (80 μL, 1.1 mmol), 7-fluoro-2-(piperazin-1-yl)benzothiazole (237 mg, 1.0 mmol), TMSN₃ (145 μL, 1.1 mmol), 2-(2-isocyanoethyl)thiophene (137 mg, 1.0 mmol) and DCM (2 mL) used as solvent. The crude was purified by preparative TLC (DCM/EA=5/1) and triturated by ether to give the product as white solid. (71 mg, 16% yield)

LC-MS (ESI): [M+1]⁺=458.50, $t_R$=4.45 min.

$^1$H NMR (400 MHz, CDCl$_3$) δ 7.32 (d, J=8.0 Hz, 1H), 7.26-7.20 (m, 1H), 7.18 (d, J=5.0 Hz, 1H), 6.93-6.88 (m, 1H), 6.81 (t, J=8.6 Hz, 1H), 6.66 (d, J=2.9 Hz, 1H), 4.75-4.58 (m, 2H), 3.60-3.50 (m, 4H), 3.46 (dd, J=9.7, 4.8 Hz, 1H), 2.72-2.53 (m, 4H), 2.05-1.84 (m, 2H), 0.78 (t, J=7.3 Hz, 3H).

$^{13}$C NMR (101 MHz, CDCl$_3$) δ 168.95, 156.80 (d, J=247.0 Hz), 155.48 (d, J=2.9 Hz), 154.04, 138.28, 127.59, 126.90 (d, J=7.8 Hz), 126.62, 124.89, 117.09 (d, J=16.0 Hz), 114.97 (d, J=3.0 Hz), 107.56 (d, J=18.8 Hz), 60.73, 49.05, 48.62, 48.21, 30.17, 19.54, 11.31.

HPLC: 100% purity.

HRMS (ESI): calculated for C$_{21}$H$_{24}$N$_7$S$_2$FNa [M+Na]$^+$= 480.1416; found 480.1427.

7-fluoro-2-(4-(1-(1-(thiazol-5-ylmethyl)-1H-tetrazol-5-yl)propyl)piperazin-1-yl)benzothiazole

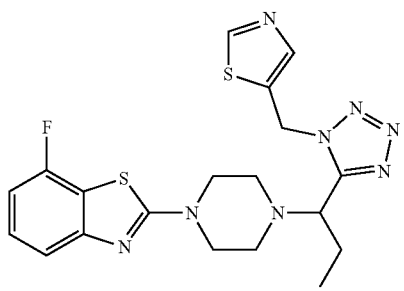 [SMILES: CCC(c1nnnn1Cc1cncs1)N1CCN(c2nc3cccc(F)c3s2)CC1]

The title compound was prepared according to GP4-3. The crude was purified by preparative TLC (DCM/EA=5/1) to give the product as white solid. (44 mg, 12% yield)

LC-MS (ESI): [M+1]$^+$445.51, t$_R$=4.15 min.

$^1$H NMR (400 MHz, DMSO) δ 7.81 (dd, J=8.0, 2.7 Hz, 2H), 7.41-7.30 (m, 2H), 7.01 (t, J=7.7 Hz, 1H), 6.48 (d, J=16.4 Hz, 1H), 6.31 (d, J=16.4 Hz, 1H), 5.22 (d, J=8.5 Hz, 1H), 4.02-3.95 (m, 4H), 3.62-3.36 (m, 4H), 2.43-2.07 (m, 2H), 0.58 (t, J=7.1 Hz, 3H).

$^{13}$C NMR (101 MHz, DMSO) δ 167.69, 161.55, 156.01 (d, J=245.1 Hz), 154.59 (d, J=2.9 Hz), 150.63, 142.65, 127.52 (d, J=8.2 Hz), 122.40, 116.42 (d, J=16.1 Hz), 115.12, 107.78 (d, J=18.8 Hz), 57.37, 47.74, 47.67, 45.25, 20.93, 9.54.

HPLC: 99% purity.

HRMS (ESI): calculated for C$_{19}$H$_{21}$N$_8$S$_2$FNa [M+Na]$^+$= 467.1212; found 467.1201.

2-((4-(1-(1-(thiophen-2-ylmethyl)-1H-tetrazol-5-yl)propyl)piperazin-1-yl)methyl)benzothiazole

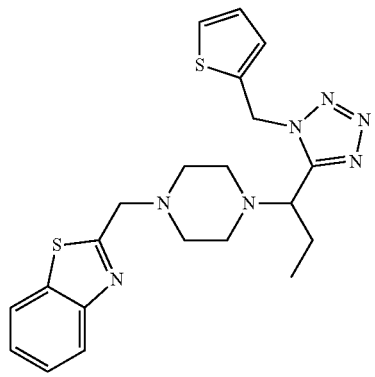 [SMILES: CCC(c1nnnn1Cc1cccs1)N1CCN(Cc2nc3ccccc3s2)CC1]

The title compound was prepared according to GP4-3. Preparative TLC purification (DCM/EA=5/1) gave the product as light yellow foam. (260 mg, 28% yield)

LC-MS (ESI): [M+1]$^+$=440.60, t$_R$=3.77 min.

$^1$H NMR (400 MHz, MeOD) δ 8.11-8.06 (m, 2H), 7.63-7.58 (m, 1H), 7.56-7.51 (m, 1H), 7.38 (dd, J=5.1, 1.2 Hz, 1H), 7.26 (d, J=3.5 Hz, 1H), 6.99 (dd, J=5.1, 3.5 Hz, 1H), 6.01 (s, 2H), 4.86 (s, 2H), 4.53 (dd, J=9.7, 5.2 Hz, 1H), 3.58-3.48 (m, 4H), 3.29-3.07 (m, 4H), 2.19-1.99 (m, 2H), 0.75 (t, J=7.3 Hz, 3H).

$^{13}$C NMR (101 MHz, MeOD) δ 161.29, 153.66, 150.08, 137.42, 136.79, 129.61, 128.48, 128.29, 128.21, 127.72, 124.30, 123.36, 60.40, 56.90, 53.04, 47.32, 47.23, 22.37, 10.63.

HPLC: 99% purity.

HRMS (ESI): calculated for C$_{21}$H$_{25}$N$_7$S$_2$Na [M+Na]$^+$= 462.1511; found 462.1505.

4,6-difluoro-2-(4-(1-(1-(thiophen-2-ylmethyl)-1H-tetrazol-5-yl)propyl)piperazin-1-yl)benzothiazole

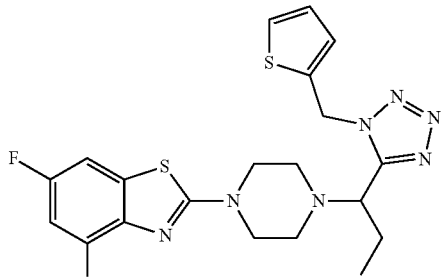

The title compound was prepared according to GP4-3. Preparative TLC purification (DCM/MeOH=50/1) and trituration by ether gave the product as off-white solid. (225 mg, 25% yield)

LC-MS (ESI): [M+1]$^+$=462.60, t$_R$=4.49 min.

$^1$H NMR (400 MHz, CDCl$_3$) δ 7.32 (dd, J=5.1, 1.1 Hz, 1H), 7.14-7.09 (ddd, J=7.6, 2.2, 1.2 Hz, 1H), 7.08-7.05 (m, 1H), 7.00 (dd, J=5.0, 3.6 Hz, 1H), 6.83 (ddd, J=10.7, 9.5, 2.4 Hz, 1H), 5.84 (d, J=5.2 Hz, 2H), 3.87 (dd, J=10.1, 4.5 Hz, 1H), 3.54 (t, J=4.8 Hz, 4H), 2.80-2.57 (m, 4H), 2.18-1.91 (m, 2H), 0.83 (t, J=7.3 Hz, 3H).

$^{13}$C NMR (101 MHz, CDCl$_3$) δ 167.84, 157.46 (dd, J=242.5, 10.4 Hz), 153.48, 152.50 (dd, J=253.5, 12.9 Hz), 137.57 (dd, J=13.0, 2.5 Hz), 135.35, 133.16 (dd, J=12.3, 6.1 Hz), 127.83, 127.41, 126.93, 103.29 (dd, J=26.6, 4.2 Hz), 101.71 (dd, J=27.5, 22.4 Hz), 61.12, 48.44, 48.37, 46.12, 19.99, 11.23.

HPLC: 98% purity.

HRMS (ESI): calculated for C$_{20}$H$_{22}$N$_7$S$_2$F$_2$ [M+1]$^+$= 462.1346; found 462.1366.

7-fluoro-5-nitro-2-(4-(1-(1-(thiophen-2-ylmethyl)-1H-tetrazol-5-yl)propyl)piperazin-1-yl)benzothiazole

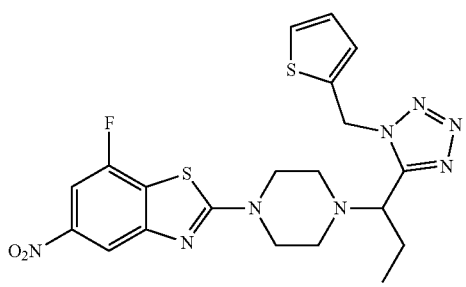

2-chloro-7-fluoro-5-nitrobenzothiazole (400 mg, 1.72 mmol), 1-(1-(1-(thiophen-2-ylmethyl)-1H-tetrazol-5-yl)propyl)piperazine (528 mg, 1.81 mmol) and Na$_2$CO$_3$ (219 mg, 2.06 mmol) were added to a 25 mL of flask with 10 mL of DMF, which was heated at 90° C. for 3 h. Aqueous workup and trituration by EtOH gave the product as yellow solid. (657 mg, 78% yield)

LC-MS (ESI): [M+1]$^+$=489.30, $t_R$=4.47 min.

$^1$H NMR (400 MHz, d6-DMSO) δ 8.04 (d, J=1.6 Hz, 1H), 7.85 (dd, J=9.3, 1.7 Hz, 1H), 7.55 (d, J=4.4 Hz, 1H), 7.25 (d, J=2.8 Hz, 1H), 7.04 (dd, J=4.9, 3.6 Hz, 1H), 5.99 (d, J=9.2 Hz, 2H), 4.29 (dd, J=9.1, 5.5 Hz, 1H), 3.64-3.51 (m, 4H), 2.69-2.58 (m, 4H), 2.07-1.82 (m, 2H), 0.76 (t, J=7.2 Hz, 3H).

$^{13}$C NMR (101 MHz, d6-DMSO) δ 169.58, 154.84 (dd, J=126.0, 122.2 Hz), 154.76 (d, J=3.8 Hz), 153.46, 146.91 (d, J=9.5 Hz), 136.61, 128.25, 127.43, 127.05, 123.94 (d, J=15.9 Hz), 109.36 (d, J=2.9 Hz), 102.78 (d, J=24.7 Hz), 58.47, 48.50, 47.45, 45.17, 20.38, 10.77.

HPLC: 99% purity.

HRMS (ESI): calculated for C$_{20}$H$_{21}$N$_8$O$_2$S$_2$FNa [M+Na]$^+$=511.1111; found 511.1125.

5-amino-7-fluoro-2-(4-(1-(1-(thiophen-2-ylmethyl)-1H-tetrazol-5-yl)propyl)piperazin-1-yl)Benzothiazole Also refer to as Mannan-007

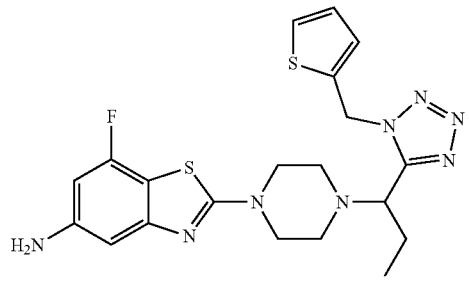 [SMILES: CCC(c1nnnn1Cc1cccs1)N1CCN(c2nc3cc([N+](=O)[O-])cc(F)c3s2)CC1]

To a suspension of 10% Pd/C (60 mg) wetted by MeOH (3 mL), 7-fluoro-5-nitro-2-(4-(1-(1-(thiophen-2-ylmethyl)-1H-tetrazol-5-yl)propyl)piperazin-1-yl)benzothiazole (600 mg, 1.23 mmol) was added, followed by addition of 6 mL of HOAc and 3 mL of MeOH. The reaction was evacuated, refilled back by hydrogen three times and kept stirring at 40° C. 2 hours. After filtering, the volatile was removed. The residue was neutralized and purified by flash column (DCM/EA=5/1) to obtain the product as light yellow foam. (180 mg, 33% yield)

LC-MS (ESI): [M+1]$^+$=459.32, $t_R$=3.98 min.

$^1$H NMR (400 MHz, CDCl$_3$) δ 7.31 (dd, J=5.1, 1.1 Hz, 1H), 7.05 (d, J=3.2 Hz, 1H), 6.99 (dd, J=5.0, 3.6 Hz, 1H), 6.66 (d, J=1.9 Hz, 1H), 6.23 (dd, J=10.9, 1.8 Hz, 1H), 5.84 (d, J=5.2 Hz, 2H), 3.85 (dd, J=10.2, 4.4 Hz, 1H), 3.80 (brs, 2H), 3.60-3.43 (m, 4H), 2.74-2.54 (m, 4H), 2.15-1.86 (m, 2H), 0.82 (t, J=7.3 Hz, 3H).

$^{13}$C NMR (101 MHz, CDCl$_3$) δ 169.75, 157.16 (d, J=224.1 Hz), 156.00, 155.85, 153.53, 146.60 (d, J=10.6 Hz), 135.37, 127.83, 127.39, 126.91, 106.24 (d, J=16.9 Hz), 101.25 (d, J=2.6 Hz), 96.88 (d, J=22.3 Hz), 61.16, 48.40, 48.38, 46.11, 19.86, 11.26.

HPLC: 96% purity.

HRMS (ESI): calculated for C$_{20}$H$_{24}$N$_8$S$_2$F [M+1]$^+$= 459.1549; found 459.1529.

The activities of the selected synthesized compounds in the present invention are listed in table-1 below, which are classified based on their activities as examined with the cell-based assays in vitro. They are measured by and divided based on the effective concentration 1.5 (EC1.5), which is the concentration of the compound is required to enhance the FOG of α-DG by 50% over the controls. H, EC1.5<5 µM; M, EC1.5-20 µM; L, EC1.5 20-50 µM; VL, EC1.5>50 µM.

TABLE 1

Compounds and their bioactivity

| Name of the compound | Activity (EC1.5) |
|---|---|
| 1. 2-(4-((1-(thiophen-2-ylmethyl)-1H-1,2,3-triazol-5-yl)methyl)piperazin-1-yl)benzothiazole | L |
| 2. 2-(4-((1-(thiophen-2-ylmethyl)-1H-tetrazol-5-yl)methyl)piperazin-1-yl)benzothiazole | M |
| 3. 2-(4-(1-(1-(thiophen-2-ylmethyl)-1H-tetrazol-5-yl)ethyl)piperazin-1-yl)benzothiazole | M |
| 4. 2-(1-(1-(furan-2-ylmethyl)-1H-tetrazol-5-yl)propyl)piperidin-4-yl)benzothiazole | M |
| 5. 2-(4-(1-(1-(furan-2-ylmethyl)-1H-tetrazol-5-yl)propyl)piperazin-1-yl)benzothiazole | M |
| 6. 2-(4-(1-(1-(thiophen-2-ylmethyl)-1H-tetrazol-5-yl)propyl)piperazin-1-yl)benzothiazole | M |
| 7. 2-(4-(1-(1-(thiophen-2-ylmethyl)-1H-tetrazol-5-yl)propyl)piperazin-1-yl)benzoxazole | M |
| 8. 2-(1-(1-(thiophen-2-ylmethyl)-1H-tetrazol-5-yl)propyl)piperidin-4-yl)benzothiazole | M |
| 9. 2-(4-(1-(1-(thiophen-2-ylmethyl)-1H-tetrazol-5-yl)propyl)piperazin-1-yl)-1H-benzimidazole | L |

TABLE 1-continued

Compounds and their bioactivity

| Name of the compound | Activity (EC1.5) |
|---|---|
| 10. 6-nitro-2-(4-(1-(1-(thiophen-2-ylmethyl)-1H-tetrazol-5-yl)propyl)piperazin-1-yl)benzothiazole | VL |
| 11. 6-amino-2-(4-(1-(1-(thiophen-2-ylmethyl)-1H-tetrazol-5-yl)propyl)piperazin-1-yl)benzothiazole | M |
| 12. 5-((3aS,4S,6aR)-2-oxohexahydro-1H-thieno[3,4-d]imidazol-4-yl)-N-(2-(4-(1-(1-(thiophen-2-ylmethyl)-1H-tetrazol-5-yl)propyl)piperazin-1-yl)benzothiazol-6-yl)pentanamide | H |
| 13. 6-fluoro-2-(4-(1-(1-(thiophen-2-ylmethyl)-1H-tetrazol-5-yl)propyl)piperazin-1-yl)benzothiazole | L |
| 14. 6-methoxy-2-(4-(1-(1-(thiophen-2-ylmethyl)-1H-tetrazol-5-yl)propyl)piperazin-1-yl)benzothiazole | M |
| 15. 6-chloro-2-(4-(1-(1-(thiophen-2-ylmethyl)-1H-tetrazol-5-yl)propyl)piperazin-1-yl)benzothiazole | M |
| 16. 6-methyl-2-(4-(1-(1-(thiophen-2-ylmethyl)-1H-tetrazol-5-yl)propyl)piperazin-1-yl)benzothiazole | L |
| 17. 6-phenyl-2-(4-(1-(1-(thiophen-2-ylmethyl)-1H-tetrazol-5-yl)propyl)piperazin-1-yl)benzothiazole | VL |
| 18. 2-chloro-N-(2-(4-(1-(1-(thiophen-2-ylmethyl)-1H-tetrazol-5-yl)propyl)piperazin-1-yl)benzothiazol-6-yl)benzamide | VL |
| 19. 2-methyl-N-(2-(4-(1-(1-(thiophen-2-ylmethyl)-1H-tetrazol-5-yl)propyl)piperazin-1-yl)benzothiazol-6-yl)benzamide | VL |
| 20. 5,6,7-trimethaxy-2-(4-(1-(1-(thiophen-2-ylmethyl)-1H-tetrazol-5-yl)propyl)piperazin-1-yl)benzothiazole | M |
| 21. 7-fluoro-2-(4-(1-(1-(thiophen-2-ylmethyl)-1H-tetrazol-5-yl)propyl)piperazin-1-yl)benzothiazole | H |
| 22. 4-nitro-2-(4-(1-(1-(thiophen-2-ylmethyl)-1H-tetrazol-5-yl)propyl)piperazin-1-yl)benzothiazole | L |
| 23. 4-aminn-2-(4-(1-(1-(thiophen-2-ylmethyl) 1H-tetrazol-5-yl)propyl)piperazin-1-yl)benzothiazole | M |
| 24. 2-(4-(1-(1-(thiophen-2-ylmethyl)-1H-tetrazol-5-yl)propyl)piperazin-1-yl)thiazolo[5,4-b]pyridine | M |
| 25. 5-fluoro-2-(4-(1-(1-(thiophen-2-ylmethyl)-1H-tetrazol-5-yl)propyl)piperazin-1-yl)benzothiazole | L |
| 26. 2-(4-(1-(1-(thiophen-2-ylmethyl)-1H-tetrazol-5-yl)propyl)piperazin-1-yl)-7-(trifluoramethyl)benzothiazole | L |
| 27. $N^1$-(7-fluorobenzothiazol-2-yl)-$N^2$-(1-(1-(thiophen-2-ylmethyl)-1H-tetrazol-5-yl)propyl)ethane-1,2-diamine | M |
| 28. 5-nitro-2-(4-(1-(1-(thiophen-2-ylmethyl)-1H-tetrazol-5-yl)propyl)piperazin-1-yl)benzothiazole | M |
| 29. 5-amino-2-(4-(1-(1-(thiophen-2-ylmpthyl)-1H-tetrazol-5-yl)propyl)piperazin-1-yl)benzothiazole | H |
| 30. 4-fluoro-2-(4-(1-(1-(thiophen-2-ylmethyl)-1H-tetrazol-5-yl)propyl)piperazin-1-yl)benzothiazole | H |
| 31. methyl 2-(4-(1-(1-(thiophen-2-ylmethyl)-1H-tetrazol-5-yl)propyl)piperazin-1-yl)benzothiazole-6-carboxylate | L |
| 32. 2-(4-(1-(1-(thiophen-2-ylmethyl)-1H-tetrazol-5-yl)propyl)piperazin-1-yl)benzothiazole-6-carboxylic acid | L |
| 33. (4-(7-fluorobenzothiazol-2-yl)piperazin-1-yl)(1-(thiophen-2-ylmethyl)-1H-tetrazol-5-yl)methanone | L |
| 34. 7-bromo-2-(4-(1-(1-(thiophen-2-ylmethyl)-1H-tetrazol-5-yl)propyl)piperazin-1-yl)benzothiazole | L |
| 35. Methyl 2-(4-(1-(1-(thiophen-2-ylmethyl)-1H-tetrazol-5-yl)propyl)piperazin-1-yl)benzothiazole-7-carboxylate | L |
| 36. 2-(4-(1-(1-(thiophen-2-ylmethyl)-1H-tetrazol-5-yl)propyl)piperazin-1-yl)benzothiazole-7-carboxylic acid | L |
| 37. 7-hydroxyl-2-(4-(1-(1-(thiophen-2-ylmethyl)-1H-tetrazol-5-yl)propyl)piperazin-1-yl)benzothiazole | L |
| 38. 2-(4-(benzothiazol-2yl)phenyl)-N-(thiophen-2-ylmethyl)butanamide | M |
| 39. 2-(4-(benzothiazol-2-yl)phenyl)-N-(thiophen-2-ylmethyl)butanethioamide | M |
| 40. 2-(4-(1-(1-(thiophen-2-ylmethyl)-1H-tetrazol-5-yl)propyl)phenyl)benzothiazole | M |
| 41. 7-fluoro-2-(4-(1-(2-(thiophen-2-yl)ethyl)-1H-tetrazol-5-yl)propyl)piperazin-1-yl)benzothiazole | L |
| 42. 7-fluoro-2-(4-(1-(1-(thiazol-5-ylmethyl)-1H-tetrazol-5-yl)propyl)piperazin-1-yl)benzothiazole | L |
| 43. 2-((4-(1-(1-(thiophen-2-ylmethyl)-1H-tetrazol-5-yl)propyl)piperazin-1-yl)methyl)benzothiazole | L |
| 44. 4,6-difluoro-2-(4-(1-(1-(thiophen-2-ylmethyl)-1H-tetrazol-5-yl)propyl)piperazin-1-yl)benzothiazole | M |
| 45. 7-fluoro-5-nitro-2-(4-(1-(1-(thiophen-2-ylmethyl)-1H-tetrazol-5-yl)propyl)piperazin-1-yl)benzothiazole | L |
| 46. 5-amino-7-fluoro-2-(4-(1-(1-(thiophen-2-ylmethyl)-1H-tetrazol-5-yl)propyl)piperazin-1-yl)benzothiazole | H |
| 47. 5-amino-4-fluoro-2-(4-(1-(1-(thiophen-2-ylmethyl)-1H-tetrazol-5-yl)propyl)piperazin-1-yl)benzothiazole | H |
| 48. 5-amino-4,7-difluoro-2-(4-(1-(1-(thiophen-2-ylmethyl)-1H-tetrazol-5-yl)propyl)piperazin-1-yl)benzothiazole | H |
| 49. 6-amino-7-fluoro-2-(4-(1-(1-(thiophen-2-ylmethyl)-1H-tetrazol-5-yl)propyl)piperazin-1-yl)benzothiazole | H |
| 50. 6-amino-4-fluoro-2-(4-(1-(1-(thiophen-2-ylmethyl)-1H-tetrazol-5-yl)propyl)piperazin-1-yl)benzothiazole | H |
| 51. 6-amino-4,7-difluoro-2-(4-(1-(1-(thiophen-2-ylmethyl)-1H-tetrazol-5-yl)propyl)piperazin-1-yl)benzothiazole | H |
| 52 5,6-diamino-4,7-difluoro-2-(4-(1-(1-(thiophen-2-ylmethyl)-1H-tetrazol-5-yl)propyl)piperazin-1-yl)benzothiazole | H |
| 53 5,6-diamino-2-(4-(1-(1-(thiophen-2-ylethyl)-1H-tetrazol-5-yl)propyl)piperazin-1-yl)benzothiazole | H |
| 54 5,6-diamino-2-(4-(1-(1-(thiophen-2-ylmethyl)-1H-tetrazol-5-yl)propyl)piperazin-1-yl)benzothiazole | H |
| 55 5-amino-7-fluoro-2-(4-(1-(1-(thiophen-2-ylethyl)-1H-tetrazol-5-yl)propyl)piperazin-1-yl)benzothiazole | H |
| 56 5-amino-7-fluoro-2-(4-(1-(1-(5-methyl-thiophen-2-ylmethyl)-1H-tetrazol-5-yl)propyl)piperazin-1-yl)benzothiazole | H |
| 57 5-amino-7-fluoro-2-(4-(1-(1-(5-fluoro-thiophen-2-ylmethyl)-1H-tetrazol-5-yl)propyl)piperazin-1-yl)benzothiazole | H |
| 58 5-amino-7-fluoro-2-(4-(1-(1-(5-nitro-thiophen-2-ylmethyl)-1H-tetrazol-5-yl)propyl)piperazin-1-yl)benzothiazole | H |
| 59 5-amino-7-fluoro-2-(4-(1-(1-(5-fluoro-thiophen-2-ylmethyl)-1H-tetrazol-5-yl)propyl)-2-methyl-piperazin-1-yl)benzothiazole | H |
| 60 5-amino-7-fluoro-2-(4-(1-(1-(5-fluoro-thiophen-2-ylethyl)-1H-tetrazol-5-yl)propyl)-2-methyl-piperazin-1-yl)benzothiazole | H |
| 61 5-amino-7-fluoro-3-amino-2-(4-(1-(1-(thiophen-2-ylethyl)-1H-tetrazol-5-yl)propyl)piperazin-1-yl)benzothiazole | H |
| 62 5-amino-7-fluoro-3-nitro-2-(4-(1-(1-(thiophen-2-ylethyl)-1H-tetrazol-5-yl)propyl)piperazin-1-yl)benzothiazole | H |
| 63 5-amino-7-fluoro-3-methyl-2-(4-(1-(1-(thiophen-2-ylethyl)-1H-tetrazol-5-yl)propyl)piperazin-1-yl)benzothiazole | H |
| 64 5-amino-7-fluoro-2-(4-(1-(1-(thiophen-2-ylethyl))-1H-tetrazol-5-yl)propyl)-3-nitro-piperazin-1-yl)benzothiazole | H |
| 65 5-amino-7-fluoro-2-(4-(1-(1-(thiophen-2-ylethyl))-1H-tetrazol-5-yl)propyl)-5-nitro-piperazin-1-yl)benzothiazole | H |
| 66 5-amino-7-fluoro-2-(4-(1-(1-(thiophen-2-ylethyl))-1H-tetrazol-5-yl)propyl)-2-amino-piperazin-1-yl)benzothiazole | H |
| 67 5-amino-7-fluoro-2-(4-(1-(1-(thiophen-2-ylethyl)-1H.tetrazol-5-yl)propyl)-2-nitro-piperazin-1-yl)benzothiazole | H |
| 68 5-amino-7-fluoro-2-(4-(1-(1-(thiophen-2-ylmethyl)-1H-tetrazol-5-yl)propyl)cycloheptyl)benzothiazole | H |
| 69 5-amino-7-fluoro-2-(4-(1-(1-(thiophen-2-ylmethyl)-1H-tetrazol-5-yl)propyl)pyrrolidine-1-yl)benzothiazole | H |
| 70 5 amino-7-fluoro-2-(4-(1-(1-(thiophen-2-ylmethyl)-1H-tetrazol-5-yl)propyl)azepane-1-yl)benzothiazole | H |
| 71 5-amino-7-fluoro-2-(4-(1-(1-(thiophen-2-ylmethyl)-1H-tetrazol-5-yl)propyl)1,4-diazepane-1-yl)benzothiazole | H |
| 72 5-amino-7-fluoro-2-(5-(1-(1-(thiophen-2-ylmethyl)-1H-tetrazol-5-yl)propyl)1,5-diazocane-1-yl)benzothiazole | H |
| 73 5-amino-7-fluoro-2-(4-(1-(1-(isothiazol-5-ylmethyl)-1H-tetrazol-5-yl)propyl)piperazin-1-yl)benzothiazole | H |
| 74 5-amino-7-fluoro-2-(4-(1-(1-(isothiazol-5-ylethyl)-1H-tetrazol-5-yl)propyl)piperazin-1-yl)benzothiazole | H |
| 75 5-amino-7-fluoro-2-(4-(1-(1-(thiophen-2-ylethyl)-1H-tetrazol-5-yl)propyl)1,4-diazepane-1-yl)benzothiazole | H |
| 76 5-amino-7-fluoro-2-(4-(1-(1-(thiophen-2-ylethyl)-1H-tetrazol-5-yl)propyl)1,4-diazepane-1-yl)benzothiazole | H |

Pharmaceutically Acceptable Salts and Prodrugs

In cases where compounds are sufficiently basic or acidic to form stable nontoxic acid or base salts, administration of the compound as a pharmaceutically acceptable salt may be appropriate. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. In particular, examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Pharmaceutical Compositions

The present invention is formulated preferably in a mixture with a pharmaceutically acceptable carrier. In general, it is preferable to administer the pharmaceutical composition in orally administrable form, but formulations may be administered via parenteral, intravenous, intramuscular, transdermal, buccal, subcutaneous, suppository or other route. Intravenous and intramuscular formulations are preferably administered in sterile saline. One of ordinary skill in the art may modify the formulation within the teachings of the specification to provide numerous formulations for a particular route of administration without rendering the compositions of the present invention unstable or compromising its therapeutic activity. In particular, a modification of a desired compound to render it more soluble in water or other vehicle, for example, may be easily accomplished by routine modification (salt formulation, esterification, etc.).

In certain pharmaceutical dosage forms, the prodrug form of the compound, especially including acylated (acetylated or other) and ether derivatives, phosphate esters and various salt forms of the present compounds, is preferred. One of ordinary skill in the art will recognize how to readily modify the present compound to a prodrug form to facilitate delivery of active compound to a targeted site within the patient.

The amount of compound included within therapeutically active formulations, according to the present invention, is an effective amount for treating the various muscular dystrophies. In general, a therapeutically effective amount of the present compound in pharmaceutical dosage form usually ranges from about 100 mg to about 2,000 mg or more, depending upon the compound used, the condition or muscular dystrophy treated and the route of administration. For purposes of the present invention, a prophylactically or preventively effective amount of the compositions, according to the present invention, falls within the same concentration range as set forth above for therapeutically effective amount and is usually the same as a therapeutically effective amount.

Administration of the active compound may range from continuous (intravenous drip) to several oral administrations per day (for example, T.I.D., B.I.D., etc.) and may include oral, topical, parenteral, intramuscular, intravenous, subcutaneous, transdermal (which may include a penetration enhancement agent), buccal and suppository administration, among other routes of administration. Enteric-coated oral tablets may also be used to enhance bioavailability and stability of the compounds from an oral route of administration. The most effective dosage form will depend upon the pharmacokinetics of the particular agent chosen, as well as the severity of disease in the patient. Oral dosage forms are particularly preferred, because of ease of administration and prospective favorable patient compliance.

To prepare the pharmaceutical compositions according to the present invention, a therapeutically effective amount of one or more of the compounds according to the present invention is preferably mixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavoring agents, preservatives, coloring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated for sustained release by standard techniques. The use of these dosage forms may significantly impact the bioavailability of the compounds in the patient.

For parenteral formulations, the carrier will usually comprise sterile water or aqueous sodium chloride solution, though other ingredients, including those that aid dispersion, also may be included. Where sterile water is to be used and maintained as sterile, the compositions and carriers must also be sterilized. Injectable suspensions may also be prepared, in which case appropriate liquid carriers, suspending agents and the like may be employed.

Stereoisomerism and Polymorphism

It is appreciated that compounds of the present invention have several chiral centers and may exist in and be isolated in optically active and racemic forms. Some compounds may exhibit polymorphism. It is to be understood that the present invention encompasses any racemic, optically active, diastereomeric, polymorphic, or stereoisomeric form, or mixtures thereof, of a compound of the invention, which possess the useful properties described herein. It being well known in the art how to prepare optically active forms such as by resolution of the racemic form by recrystallization techniques, by synthesis from optically-active starting materials, by chiral synthesis, or by chromatographic separation using a chiral stationary phase.

REFERENCES CITED

Ackroyd, M. R., L. Skordis, et al. (2009). "Reduced expression of fukutin related protein in mice results in a model for fukutin related protein associated muscular dystrophies." *Brain* 132(Pt 2): 439-451.

Acsadi, G., S. A. Moore, et al. (2012). "Novel mutation in spectrin-like repeat 1 of dystrophin central domain causes protein misfolding and mild Becker muscular dystrophy." *J Biol Chem* 287(22): 18153-18162.

Akasaka-Manya, K., H. Manya, et al. (2004). "Mutations of the POMT1 gene found in patients with Walker-Warburg syndrome lead to a defect of protein O-mannosylation." *Biochem Biophys Res Commun* 325(1): 75-79.

Alhamidi, M., E. Kjeldsen Buvang, et al. (2011). "Fukutin-related protein resides in the Golgi cisternae of skeletal muscle fibres and forms disulfide-linked homodimers via an N-terminal interaction." *PLoS One* 6(8): e22968.

Baenziger, J. U. (2013). "O-mannosylation of cadherins." Proc Natl Acad Sci USA 110(52): 20858-20859.

Bao, X., M. Kobayashi, et al. (2009). "Tumor suppressor function of laminin-binding alpha-dystroglycan requires a distinct beta3-N-acetylglucosaminyltransferase." Proc Natl Acad Sci USA 106(29): 12109-12114.

Barone, R., C. Aiello, et al. (2012). "DPM2-CDG: a muscular dystrophy-dystroglycanopathy syndrome with severe epilepsy." Ann Neurol 72(4): 550-558.

Barresi, R. and K. P. Campbell (2006). "Dystroglycan: from biosynthesis to pathogenesis of human disease." J Cell Sci 119(Pt 2): 199-207.

Beltran-Valero de Bernabe, D., S. Currier, et al. (2002). "Mutations in the O-mannosyltransferase gene POMT1 give rise to the severe neuronal migration disorder Walker-Warburg syndrome." Am J Hum Genet 71(5): 1033-1043.

Biancheri, R., E. Bertini, et al. (2006). "POMGnT1 mutations in congenital muscular dystrophy: genotype-phenotype correlation and expanded clinical spectrum." Arch Neurol 63(10): 1491-1495.

Bleckmann, C., H. Geyer, et al. (2009). "O-glycosylation pattern of CD24 from mouse brain." Biol Chem 390(7): 627-645.

Bowe, M. A., K. A. Deyst, et al. (1994). "Identification and purification of an agrin receptor from Torpedo postsynaptic membranes: a heteromeric complex related to the dystroglycans." Neuron 12(5): 1173-1180.

Brockington, M., Y. Yuva, et al. (2001). "Mutations in the fukutin-related protein gene (FKRP) identify limb girdle muscular dystrophy 2I as a milder allelic variant of congenital muscular dystrophy MDC1C." Hum Mol Genet 10(25): 2851-2859.

Buysse, K., M. Riemersma, et al. (2013). "Missense mutations in beta-1,3-N-acetylglucosaminyltransferase 1 (B3GNT1) cause Walker-Warburg syndrome." Hum Mol Genet 22(9): 1746-1754.

Camacho Vanegas, O., E. Bertini, et al. (2001). "Ullrich scleroatonic muscular dystrophy is caused by recessive mutations in collagen type VI." Proc Natl Acad Sci USA 98(13): 7516-7521.

Carss, K. J., E. Stevens, et al. (2013). "Mutations in GDP-Mannose Pyrophosphorylase B Cause Congenital and Limb-Girdle Muscular Dystrophies Associated with Hypoglycosylation of alpha-Dystroglycan." Am J Hum Genet 93(1): 29-41.

de Bernabe, D. B., K. Inamori, et al. (2009). "Loss of alpha-dystroglycan laminin binding in epithelium-derived cancers is caused by silencing of LARGE." J Biol Chem 284(17): 11279-11284.

Dobson, C. M., S. J. Hempel, et al. (2012). "O-Mannosylation and human disease." Cell Mol Life Sci.

Durbeej, M., E. Larsson, et al. (1995). "Non-muscle alpha-dystroglycan is involved in epithelial development." J Cell Biol 130(1): 79-91.

Dwyer, C. A., E. Baker, et al. (2012). "RPTPzeta/phosphacan is abnormally glycosylated in a model of muscle-eye-brain disease lacking functional POMGnT1." Neuroscience 220: 47-61.

Endo, T. (2003). "[Muscular dystrophies due to defective O-mannosylation of alpha-dystroglycan]." Tanpakushitsu Kakusan Koso 48(8 Suppl): 1133-1140.

Ervasti, J. M. and K. P. Campbell (1993). "Dystrophin-associated glycoproteins: their possible roles in the pathogenesis of Duchenne muscular dystrophy." Mol Cell Biol Hum Dis Ser 3: 139-166.

Ervasti, J. M., K. Ohlendieck, et al. (1990). "Deficiency of a glycoprotein component of the dystrophin complex in dystrophic muscle." Nature 345(6273): 315-319.

Esapa, C. T., M. A. Benson, et al. (2002). "Functional requirements for fukutin-related protein in the Golgi apparatus." Hum Mol Genet 11(26): 3319-3331.

Hara, Y., B. Balci-Hayta, et al. (2011). "A dystroglycan mutation associated with limb-girdle muscular dystrophy." N Engl J Med 364(10): 939-946.

Hoffman, E. P., R. H. Brown, Jr., et al. (1987). "Dystrophin: the protein product of the Duchenne muscular dystrophy locus." Cell 51(6): 919-928.

Hu, Y., Z. F. Li, et al. (2011). "Large induces functional glycans in an O-mannosylation dependent manner and targets GlcNAc terminals on alpha-dystroglycan." PLoS One 6(2): e16866.

Ibraghimov-Beskrovnaya, O., J. M. Ervasti, et al. (1992). "Primary structure of dystrophin-associated glycoproteins linking dystrophin to the extracellular matrix." Nature 355(6362): 696-702.

Jae, L. T., M. Raaben, et al. (2013). "Deciphering the glycosylome of dystroglycanopathies using haploid screens for lassa virus entry." Science 340(6131): 479-483.

Kobayashi, K., Y. Nakahori, et al. (1998). "An ancient retrotransposal insertion causes Fukuyama-type congenital muscular dystrophy." Nature 394(6691): 388-392.

Lefeber, D. J., J. Schonberger, et al. (2009). "Deficiency of Dol-P-Man synthase subunit DPM3 bridges the congenital disorders of glycosylation with the dystroglycanopathies." Am J Hum Genet 85(1): 76-86.

Lim, L. E. and K. P. Campbell (1998). "The sarcoglycan complex in limb-girdle muscular dystrophy." Curr Opin Neurol 11(5): 443-452.

Lommel, M. and S. Strahl (2009). "Protein O-mannosylation: conserved from bacteria to humans." Glycobiology 19(8): 816-828.

Manzini, M. C., D. E. Tambunan, et al. (2012). "Exome sequencing and functional validation in zebrafish identify GTDC2 mutations as a cause of Walker-Warburg syndrome." Am J Hum Genet 91(3): 541-547.

Mayer, U., G. Saher, et al. (1997). "Absence of integrin alpha 7 causes a novel form of muscular dystrophy." Nat Genet 17(3): 318-323.

Nguyen, H. H., V. Jayasinha, et al. (2002). "Overexpression of the cytotoxic T cell GalNAc transferase in skeletal muscle inhibits muscular dystrophy in mdx mice." Proc Natl Acad Sci USA 99(8): 5616-5621.

Pacharra, S., F. G. Hanisch, et al. (2012). "Neurofascin 186 is O-mannosylated within and outside of the mucin domain." J Proteome Res 11(8): 3955-3964.

Pacharra, S., F. G. Hanisch, et al. (2013). "The lecticans of mammalian brain perineural net are O-mannosylated." J Proteome Res 12(4): 1764-1771.

Rezniczek, G. A., P. Konieczny, et al. (2007). "Plectin 1f scaffolding at the sarcolemma of dystrophic (mdx) muscle fibers through multiple interactions with beta-dystroglycan." J Cell Biol 176(7): 965-977.

Saito, F., M. Kanagawa, et al. (2014). "Overexpression of LARGE suppresses muscle regeneration via down-regulation of insulin-like growth factor 1 and aggravates muscular dystrophy in mice." Hum Mol Genet 23(17): 4543-4558.

Schneider, M., A. A. Khalil, et al. (2006). "Perlecan and Dystroglycan act at the basal side of the Drosophila follicular epithelium to maintain epithelial organization." Development 133(19): 3805-3815.

Sgambato, A., A. Camerini, et al. (2007). "Expression of dystroglycan correlates with tumor grade and predicts survival in renal cell carcinoma." *Cancer Biol Ther* 6(12): 1840-1846.

Sgambato, A., B. De Paola, et al. (2007). "Dystroglycan expression is reduced during prostate tumorigenesis and is regulated by androgens in prostate cancer cells." *J Cell Physiol* 213(2): 528-539.

Sgambato, A., M. Migaldi, et al. (2003). "Dystroglycan expression is frequently reduced in human breast and colon cancers and is associated with tumor progression." *Am J Pathol* 162(3): 849-860.

Smalheiser, N. R. and N. B. Schwartz (1987). "Cranin: a laminin-binding protein of cell membranes." *Proc Natl Acad Sci USA* 84(18): 6457-6461.

Smith, F. J., R. A. Eady, et al. (1996). "Plectin deficiency results in muscular dystrophy with epidermolysis bullosa." *Nat Genet* 13(4): 450-457.

Strahl-Bolsinger, S., M. Gentzsch, et al. (1999). "Protein O-mannosylation." *Biochim Biophys Acta* 1426(2): 297-307.

Swiderski, K., S. A. Shaffer, et al. (2014). "Phosphorylation within the cysteine-rich region of dystrophin enhances its association with beta-dystroglycan and identifies a potential novel therapeutic target for skeletal muscle wasting." *Hum Mol Genet*.

van Reeuwijk, J., P. K. Grewal, et al. (2007). "Intragenic deletion in the LARGE gene causes Walker-Warburg syndrome." *Hum Genet* 121(6): 685-690.

van Reeuwijk, J., M. Janssen, et al. (2005). "POMT2 mutations cause alpha-dystroglycan hypoglycosylation and Walker-Warburg syndrome." *J Med Genet* 42(12): 907-912.

Vuillaumier-Barrot, S., C. Bouchet-Seraphin, et al. (2012). "Identification of mutations in TMEM5 and ISPD as a cause of severe cobblestone lissencephaly." *Am J Hum Genet* 91(6): 1135-1143.

Wells, L. (2013). "The o-mannosylation pathway: glycosyltransferases and proteins implicated in congenital muscular dystrophy." *J Biol Chem* 288(10): 6930-6935.

Whitmore, C., M. Fernandez-Fuente, et al. (2014). "The transgenic expression of LARGE exacerbates the muscle phenotype of dystroglycanopathy mice." *Hum Mol Genet* 23(7): 1842-1855.

Xiong, H., K. Kobayashi, et al. (2006). "Molecular interaction between fukutin and POMGnT1 in the glycosylation pathway of alpha-dystroglycan." *Biochem Biophys Res Commun* 350(4): 935-941.

Xu, H., X. R. Wu, et al. (1994). "Murine muscular dystrophy caused by a mutation in the laminin alpha 2 (Lama2) gene." *Nat Genet* 8(3): 297-302.

Xu, R., K. Chandrasekharan, et al. (2007). "Overexpression of the cytotoxic T cell (CT) carbohydrate inhibits muscular dystrophy in the dyW mouse model of congenital muscular dystrophy 1A." *Am J Pathol* 171(1): 181-199.

Xu, R., S. DeVries, et al. (2009). "Overexpression of Galgt2 reduces dystrophic pathology in the skeletal muscles of alpha sarcoglycan-deficient mice." *Am J Pathol* 175(1): 235-247.

Yang, A. C., B. G. Ng, et al. (2013). "Congenital disorder of glycosylation due to DPM1 mutations presenting with dystroglycanopathy-type congenital muscular dystrophy." *Mol Genet Metab*.

Yang, B., D. Jung, et al. (1995). "SH3 domain-mediated interaction of dystroglycan and Grb2." *J Biol Chem* 270(20): 11711-11714.

Yoshida-Moriguchi, T., T. Willer, et al. (2013). "SGK196 Is a Glycosylation-Specific O-Mannose Kinase Required for Dystroglycan Function." *Science*.

The invention claimed is:
1. A compound having the following formula I,

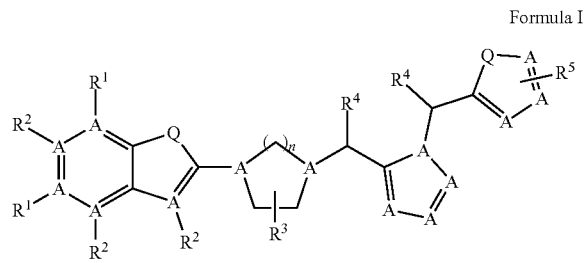

Formula I

Wherein:
A is independently Carbon or Nitrogen,
Q is independently O, S, NW, $CH_2$, CHW, or $C(W)_2$, wherein W is halogen (F, Cl, Br, I), OH, $NO_2$,
n is independently 1, 2, 3, 4, or 5,
$R^1$ independently, are Cl, Br, F, I, OH, $NO_2$, COOH, NW, $C_{1-6}H_nW_m$, wherein: W is halogen (F, Cl, Br, I), n=0-8, m=1-5, $C_{1-5}$acyl, $C_{1-5}$alkenyl, $C_{1-5}$ alkynyl, $N_3$, CN, $C(O)NH2$, $C(O)NH(C_{1-5}$acyl), $C(O)NH(C_{1-5}$ alkyl), $C(O)O(C_{1-5}$ alkyl), $C(O)O(C_{1-5}$ alkenyl), $C(O)O(C_{1-5}$ alkynyl), $O(C_{1-5}$ alkyl), $O(C_{1-5}$ alkenyl), $O(C_{1-5}$ alkynyl), $S(C_{1-5}$ alkyl), $S(C_{1-5}$ alkenyl), $S(C_{1-5}$ alkynyl), $SO(C_{1-5}$ alkyl), $SO(C_{1-5}$ alkenyl), $SO(C_{1-5}$ alkynyl), $SO_2(C_{1-5}$ alkyl), $SO_2(C_{1-5}$ alkenyl), $SO_2(C_{1-5}$ alkynyl), $O_3S(C_{1-5}$ acyl), $O_3S(C_{1-5}$ alkyl), $O_3S(C_{1-5}$ alkenyl), $O_3S$(alkynyl), $NH_2$, $NH(C_{1-5}$ alkyl), $NH(C_{1-5}$ alkenyl), $NH(C_{1-4}$ alkynyl), $NH(C_{1-4}$ acyl), amino acids, or biotin,
$R^2$ independently, are H, OH, COOH, $SO_2$, $SO_3$, $SO_4$, $PO_3$, $PO_4$, CN, Cl, Br, F, I, $NO_2$, $NH_2$, $NH(C_{1-8}$ alkyl), $NH(C_{1-8}$ alkenyl), $NH(C_{1-8}$ alkynyl), $NH(C_{1-8}$ acyl), $N(C_{1-8}$ alkyl$)_2$, $N(C_{1-8}$ acyl$)_2$, $O(C_{1-8}$ acyl), $O(C_{1-8}$ alkyl), $O(C_{1-8}$ alkenyl), $O(C_{1-8}$ alkynyl), $OC_{1-4}H_nW_m$, wherein: W is halogen (F, Cl, Br, I), n=0-8, m=1-5, $S(C_{1-8}$ acyl), $S(C_{1-8}$ alkyl), $S(C_{1-8}$ alkenyl), $S(C_{1-4}$ alkynyl), $C_{1-8}$ alkyl, $C_{1-8}$ acyl, $C_{1-8}$ alkenyl, $C_{1-8}$ alkynyl, $C_{1-6}H_nW_m$, wherein: W is halogen (F, Cl, Br, I), n=0-8, m=1-5;
$R^3$ and $R^5$ independently, are H, $N_3$, OH, $SO_2$, $SO_3$, $SO_4$, $PO_3$, $PO_4$, CN, Cl, Br, F, I, $NO_2$, $C_{1-4}$ alkyl, $C_{1-4}$ acyl, $C_{1-4}$ alkenyl, $C_{1-4}$ alkynyl, $NH_2$, $NH(C_{1-4}$ alkyl), $NH(C_{1-4}$ alkenyl), $NH(C_{1-4}$ alkynyl), $NH(C_{1-4}$ acyl), $N(C_{1-4}$ alkyl$)_2$, $N(C_{1-4}$ acyl$)_2$, $O(C_{1-4}$ acyl), $O(C_{1-4}$ alkyl), $O(C_{1-4}$ alkenyl), $O(C_{1-4}$ alkynyl), $S(C_{1-4}$ acyl), $S(C_{1-4}$ alkyl), $S(C_{1-4}$ alkenyl), $S(C_{1-4}$ alkynyl), or $C_{1-4}H_nW_m$, wherein: W is halogen (F, Cl, Br, I), n=1-8, m=1-5, or $OC_{1-4}H_nW_m$, wherein W is halogen (F, Cl, Br, I), n=1-8, m=1-5;
$R^4$ independently, are H, OH, COOH, $SO_2$, $SO_3$, $SO_4$, $PO_3$, $PO_4$, CN, Cl, Br, F, I, $NO_2$, $NH_2$, $NH(C_{1-8}$ alkyl), $NH(C_{1-8}$ alkenyl), $NH(C_{1-8}$ alkynyl), $NH(C_{1-8}$ acyl), $N(C_{1-8}$ alkyl$)_2$, $N(C_{1-8}$ acyl$)_2$, $O(C_{1-8}$ acyl), $O(C_{1-8}$ alkyl), $O(C_{1-8}$ alkenyl), $O(C_{1-8}$ alkynyl), $OC_{1-4}H_nW_m$, wherein: W is halogen (F, Cl, Br, I), n=0-8, m=1-5, $S(C_{1-8}$ acyl), $S(C_{1-8}$ alkyl), $S(C_{1-8}$ alkenyl), $S(C_{1-4}$ alkynyl), $C_{1-8}$ alkyl, $C_{1-8}$ acyl, $C_{1-8}$ alkenyl, $C_{1-8}$ alkynyl, $C_{1-6}H_nW_m$, wherein: W is halogen (F, Cl, Br, I), n=0-8, m=1-5.

2. A pharmaceutical composition comprising a compound of claim 1 or its stereoisomer, enantiomer, pharmaceutical acceptable salt, and ester in admixture with a pharmaceutically acceptable carrier.

3. The pharmaceutical composition of claim 2, wherein said composition is formulated for oral, intramuscular, intravenous, intranasal, intrapulmonary, subcutaneous, transdermal, or topical, administration.

4. A method for enhancing the functional O-mannosylation of α-DG in a cell comprising contacting a cell with a compound of claim 1 thereby increasing the functional O-mannosyl glycans of α-DG in the cell to more than 8% of the baseline of the functional O-mannosyl glycans in the cell.

5. The method of claim 4, wherein said method is carried out in vitro,
   compound of claim 1 contacting a cell in cell culture conditions to enhance the functional O-mannosylation of α-DG and its variants in the cell.

6. The method of claim 4, wherein the cell is a normal cell, cancer cell, cell with genetic defects, a cell with genetic modification, or cell with aberrant glycosylation.

7. A method for treating metastatic cancer that is associated with hypo glycosylation of α-DG, comprising administering to a subject in need of treatment an effective amount of the pharmaceutical composition of claim 2 thereby treating the subject suffering from metastatic cancer.

8. The method of claim 7, wherein the metastatic cancer is breast cancer, prostate cancer, small cell lung cancer, lung adenocarcinoma, liver cancer, bone cancer, osteosarcoma, esophagus cancer, kidney cancer, melanoma, bladder cancer, pancreatic cancer, basal cell carcinoma, cervical cancer, ovarian cancer, glioblastoma, neuroblastoma, retinoblastoma, meningioma, colon/rectum cancer, lymphoma, leukemia, medulloblastoma, skin cancer or sarcoma, brain cancer.

9. The method of claim 8, wherein the cancer has metastasized to one or more organs.

10. A method for treating muscular dystrophies comprising administering to a subject in need of treatment an effective amount of the pharmaceutical composition of claim 2 thereby treating the subject suffering from muscular dystrophies.

11. The method of claim 10, wherein the muscular dystrophies are dystroglycanopathies.

12. The method of claim 11, wherein the dystroglycanopathies are caused by the genetic defects in the genes: DAG1, DAG2, POMT1, POMT2, POMGNT1, LARGE, LARGE2, GTDC2, B4GAT1, B3GALNT2, DPM1, DPM2, DPM3, DOLK, POMK, GMPPB, FKTN, FKRP, ISPD, and TMEM5.

13. The method of claim 10, wherein the muscular dystrophies are Duchenne muscular dystrophy (DMD) and Becker muscular dystrophy (BMD).

14. The method of claim 10, wherein the muscular dystrophies are Limb-Girdle Muscular Dystrophies associated with the dystroglycanopathies caused by the genetic defects in the genes: DAG1, DAG2, POMT1, POMT2, POMGNT1, LARGE, LARGE2, GTDC2, B4GAT1, B3GALNT2, DPM1, DPM2, DPM3, DOLK, POMK, GMPPB, FKTN, FKRP, ISPD, and TMEM5.

15. The method of claim 10, wherein the muscular dystrophies are congenital muscular dystrophies (CMD) associated with dystroglycanopathies caused by the genetic defects in the genes: DAG1, DAG2, POMT1, POMT2, POMGNT1, LARGE, LARGE2, GTDC2, B4GAT1, B3GALNT2, DPM1, DPM2, DPM3, DOLK, POMK, GMPPB, FKTN, FKRP, ISPD, and TMEM.

16. The method of claim 10, wherein the muscular dystrophies are Bethlem myopathy and MDs associated with delayed motor milestones and skin blistering that are caused by genetic defects in the genes: α7 Integrin and Plectin-1.

17. A method for treating ocular disease, Muscle Eyes-Brain syndrome associated with dystroglycanopathies caused by the genetic defects in the genes: DAG1, DAG2, POMT1, POMT2, POMGNT1, LARGE, LARGE2, GTDC2, B4GAT1, B3GALNT2, DPM1, DPM2, DPM3, DOLK, POMK, GMPPB, FKTN, FKRP, ISPD, and TMEM5.

* * * * *